US006694977B1

(12) United States Patent
Federowicz et al.

(10) Patent No.: US 6,694,977 B1
(45) Date of Patent: Feb. 24, 2004

(54) MIXED-MODE LIQUID VENTILATION GAS AND HEAT EXCHANGE

(75) Inventors: Michael Federowicz, Riverside, CA (US); Sandra R. Russell, Solana Beach, CA (US); Steven B. Harris, Salt Lake City, UT (US)

(73) Assignee: Critical Care Research, Inc., Rancho Cucamonga, CA (US)

( * ) Notice: Subject to any disclaimer, the term of this patent is extended or adjusted under 35 U.S.C. 154(b) by 0 days.

(21) Appl. No.: 09/543,709

(22) Filed: Apr. 5, 2000

Related U.S. Application Data

(63) Continuation of application No. 09/410,814, filed on Oct. 1, 1999, now abandoned.

(51) Int. Cl.[7] .............. A61M 16/00; A62B 7/00
(52) U.S. Cl. ............. 128/204.18; 128/913; 128/201.13; 128/203.26; 128/207.14
(58) Field of Search ............ 128/203.26, 203.25, 128/204.17, 204.15, 202.26, 202.25, 201.21, 201.13, 913, 207.14, 204.18; 62/259.3

(56) References Cited

U.S. PATENT DOCUMENTS

| | | | | |
|---|---|---|---|---|
| 5,335,650 A | | 8/1994 | Shaffer et al. | |
| 5,407,426 A | * | 4/1995 | Spears | 128/898 |
| 5,437,272 A | * | 8/1995 | Fuhrman | 128/203.12 |
| 5,540,225 A | * | 7/1996 | Schutt | 128/207.15 |
| 5,653,685 A | * | 8/1997 | Klatz et al. | 128/201.21 |
| 5,927,273 A | * | 7/1999 | Federowicz et al. | 128/200.24 |
| 6,041,777 A | * | 3/2000 | Faithfull et al. | 128/200.24 |
| 6,105,572 A | * | 8/2000 | Shaffer et al. | 128/200.24 |
| 6,149,624 A | * | 11/2000 | McShane | 604/113 |
| 6,166,092 A | * | 12/2000 | Sekins et al. | 514/772 |
| 6,346,552 B1 | * | 2/2002 | Albrecht | 514/771 |

* cited by examiner

Primary Examiner—Weilun Lo
Assistant Examiner—Darwin P. Erezo

(57) ABSTRACT

A novel technique for ventilation and heat exchange is disclosed called Mixed-mode Liquid Ventilation (MMLV). This technique uses an endotracheal catheter to add and remove liquid from the lungs continuously and/or cyclically, and deliver gas at a rate independent of the delivery of liquid. This technique produces small-scale mixing of gas and liquid in the airways, allowing for efficient gas and heat exchange. Medical uses for the technique are disclosed. These uses include induction and reversal of hyperthermia, and hypothermia.

14 Claims, 29 Drawing Sheets

FIGURE 4

| Cycle | PFC Infusion Temp (deg. C) | PFC Suction Peak Temp (deg. C) | Cycle Start (sec) | Cycle Stop (sec) | Cycle Length (sec) | PFC Infusion Volume (mL) | Volume Suctioned (mL) | PFC Suction Temp Minus PFC Infusion Temp | Heat Removed (calculated) Using Suction Inf. Vol. Only | Heat Removed (calculated) Using Suction Vol. & Inf. Vol. |
|---|---|---|---|---|---|---|---|---|---|---|
| 1 | -1.3 | 27.3 | 0 | 240 | 240 | 624 | 325 | 29 | 8,929 | 4,845 |
| 2 | -0.4 | 31.3 | 570 | 775 | 205 | 533 | 525 | 32 | 8,464 | 8,339 |
| 3 | -0.4 | 30.7 | 1,020 | 1,268 | 248 | 645 | 670 | 31 | 10,014 | 10,401 |
| 4 | 0.0 | 28.7 | 1,472 | 1,680 | 208 | 541 | 490 | 29 | 7,760 | 7,031 |
| 5 | -0.2 | 29.7 | 1,862 | 2,102 | 240 | 624 | 540 | 30 | 9,338 | 8,090 |
| 6 | -0.1 | 29.1 | 2,282 | 2,520 | 238 | 619 | 620 | 29 | 9,038 | 9,055 |
| 7 | -0.6 | 29.4 | 2,700 | 2,935 | 235 | 611 | 600 | 30 | 9,156 | 8,994 |
| 8 | 0.0 | 28.8 | 3,122 | 3,360 | 238 | 619 | 620 | 29 | 8,923 | 8,940 |
| 9 | -0.1 | 28.9 | 3,542 | 3,780 | 238 | 619 | 640 | 29 | 8,976 | 9,282 |
| 10 | -0.3 | 27.9 | 3,934 | 4,170 | 236 | 614 | 600 | 28 | 8,630 | 8,441 |
| 11 | -0.2 | 27.4 | 4,292 | 4,540 | 248 | 645 | 610 | 28 | 8,882 | 8,406 |
| 12 | -0.1 | 29.7 | 4,652 | 4,890 | 238 | 619 | 640 | 30 | 9,208 | 9,522 |
| 13 | -0.3 | 26.1 | 4,984 | 5,220 | 236 | 614 | 640 | 26 | 8,109 | 8,453 |
| 14 | -0.4 | 25.6 | 5,314 | 5,542 | 228 | 593 | 640 | 26 | 7,700 | 8,305 |
| 15 | -0.7 | 25.1 | 5,654 | 5,881 | 227 | 590 | 620 | 26 | 7,637 | 8,012 |
| Column Totals | | | | | 3,503 | 9,108 | 8,455 | | 130,765 | 126,115 |

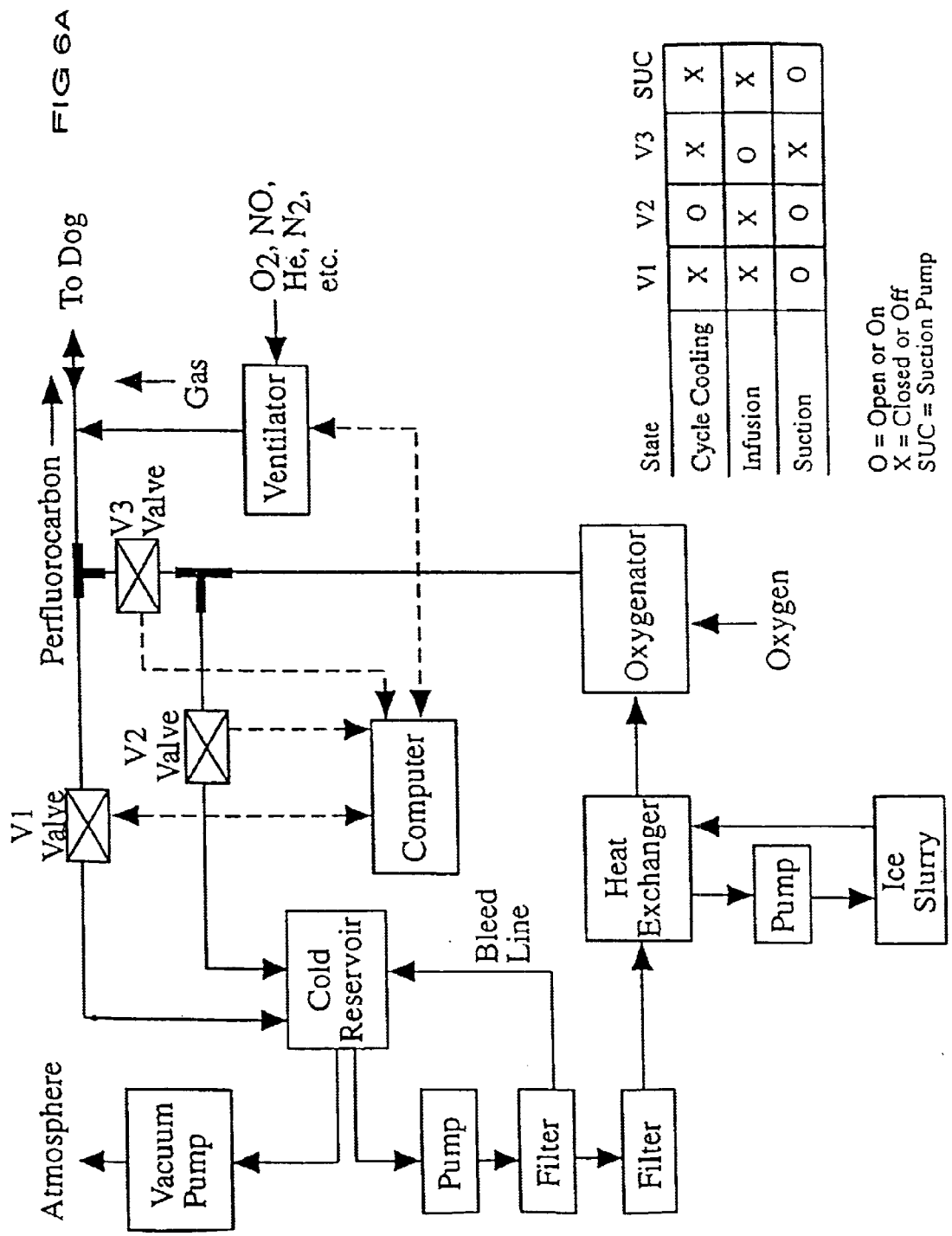

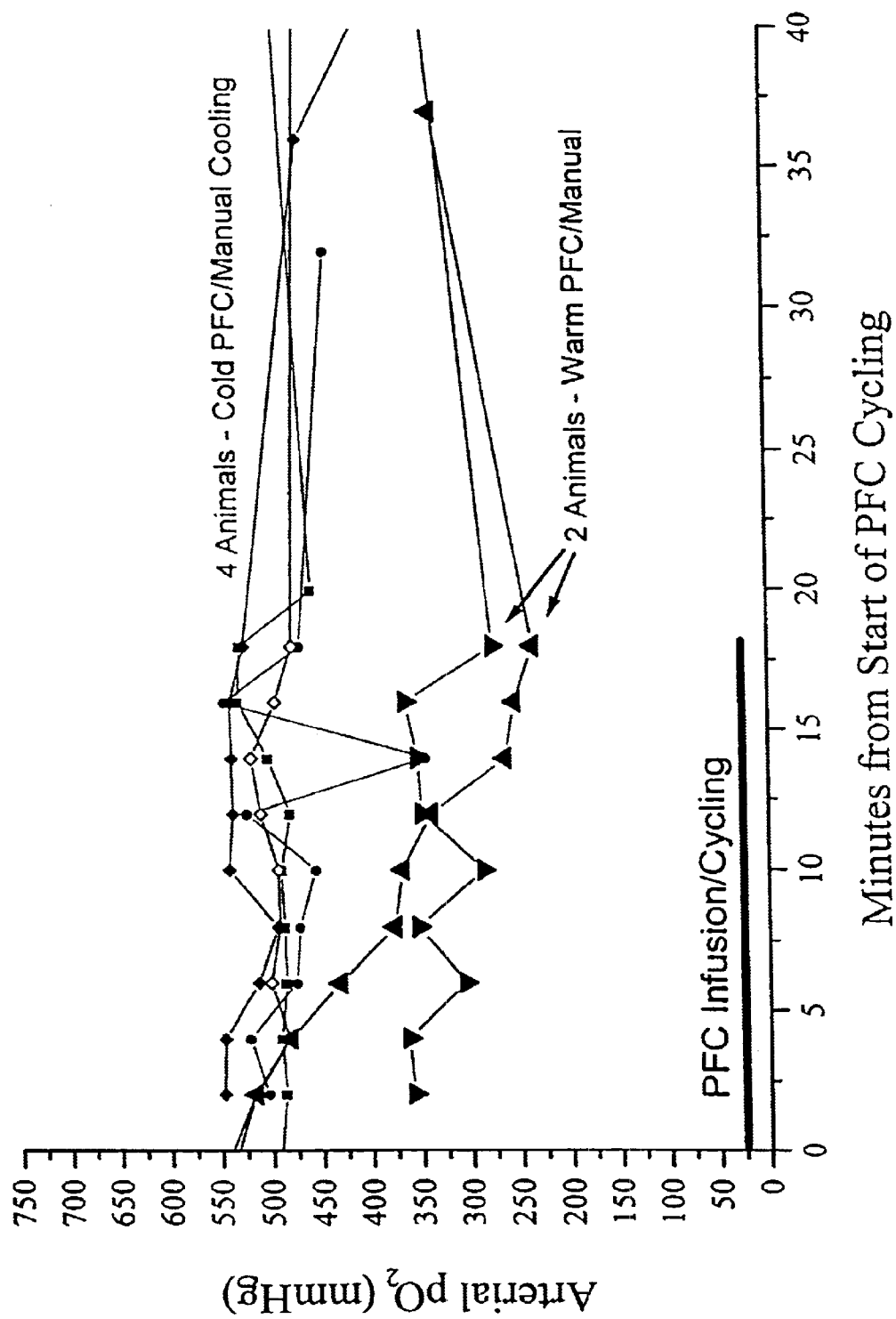

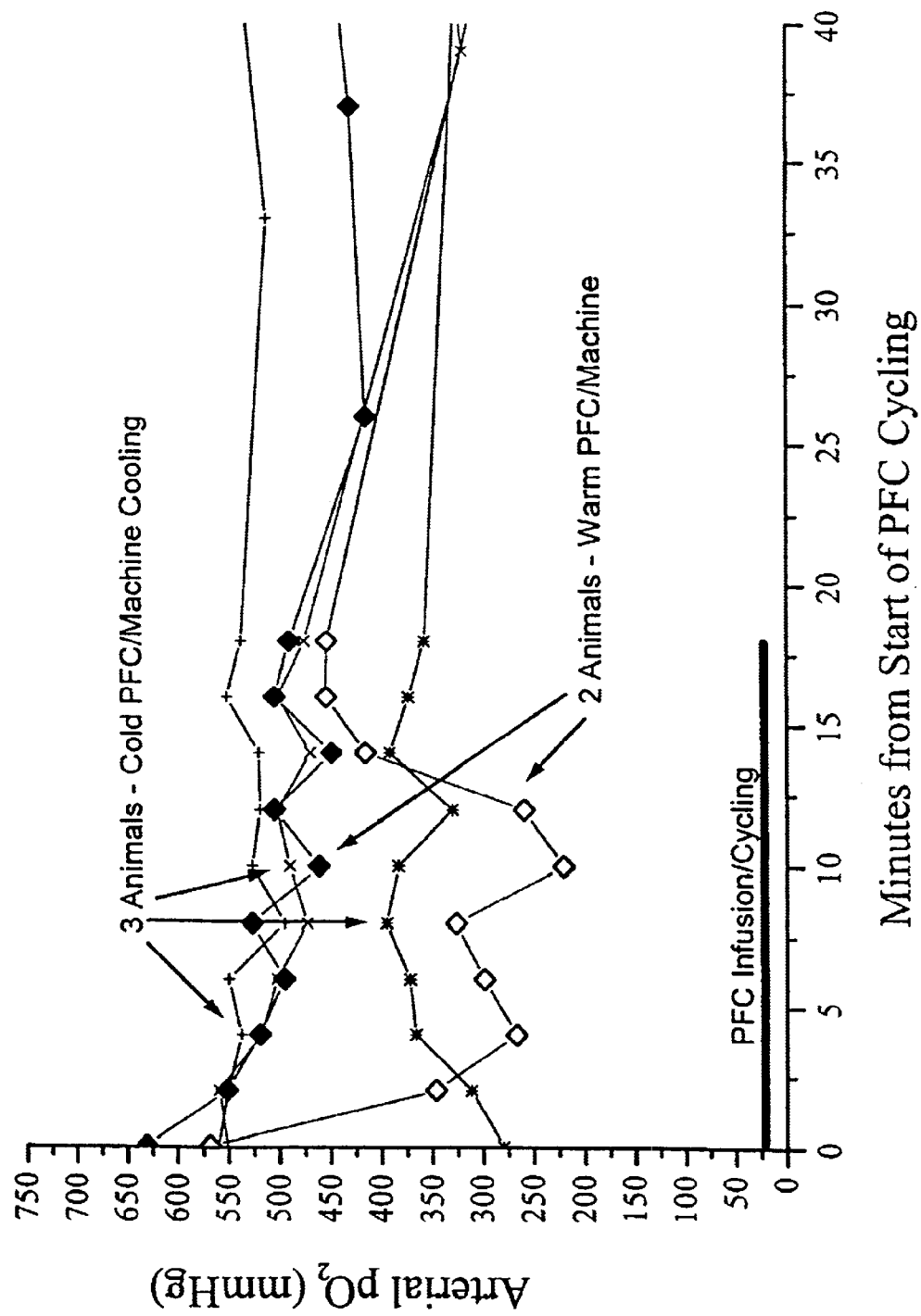

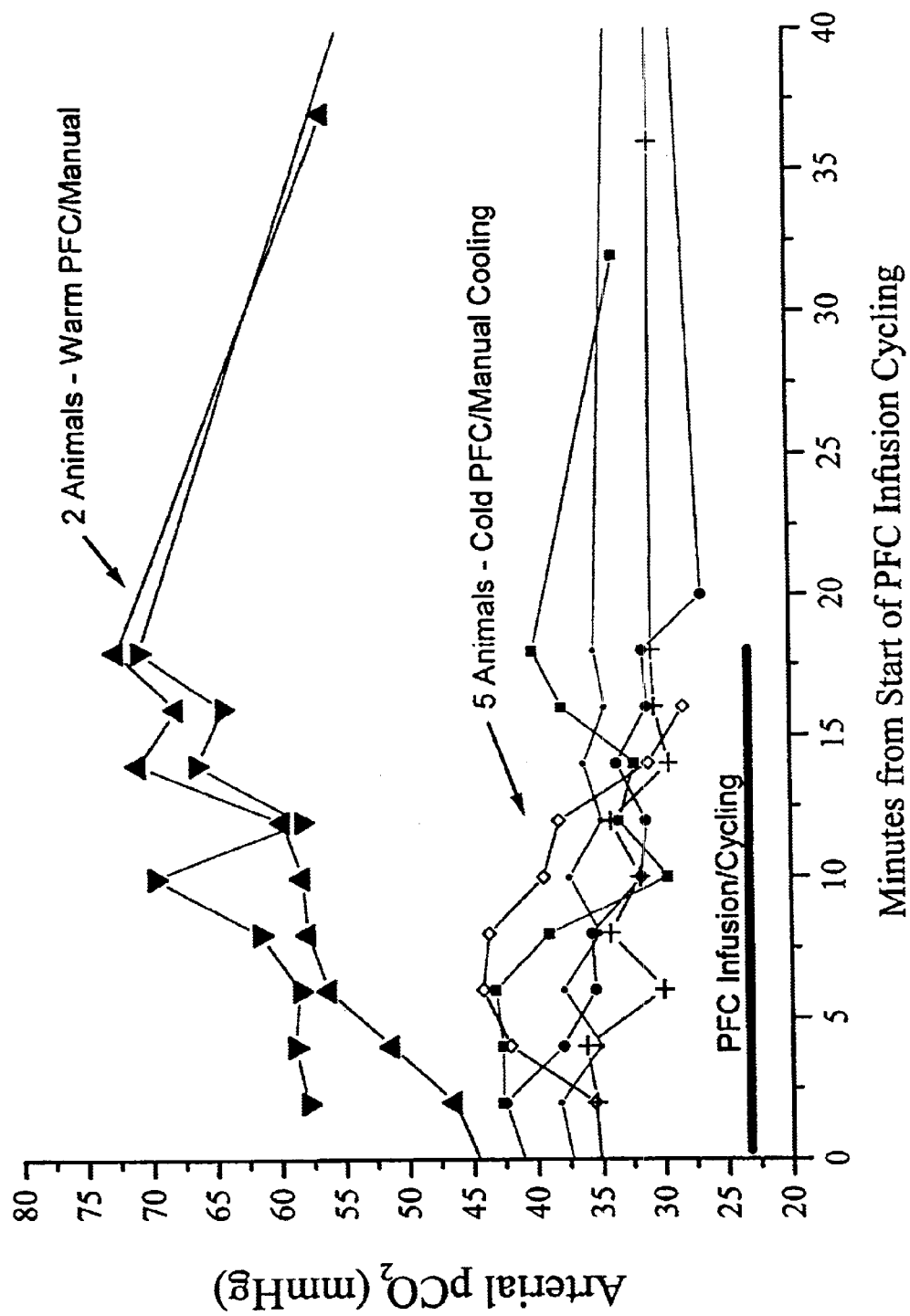

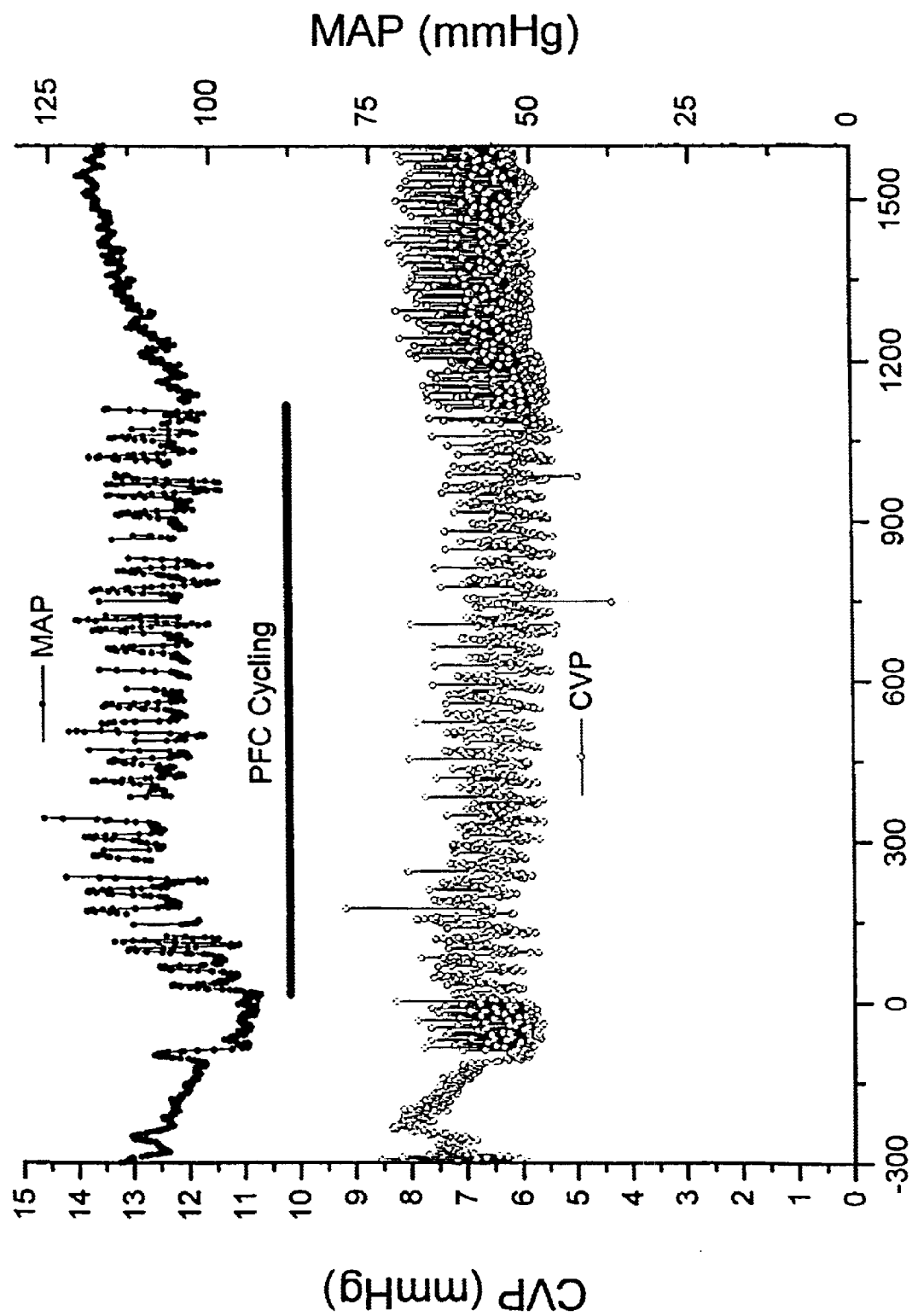

MIXED-MODE LIQUID VENTILATION GAS AND HEAT EXCHANGE

This application is a continuation of Ser. No. 09/410,814 filed Oct. 1, 1999 now abandoned.

RELATED APPLICATIONS

The present invention relates to ventilator and heat exchange systems and, more particularly, to a "mixed-mode" gas-plus-liquid ventilator system using an endotracheal catheter to add and remove liquid ventilation or heat-exchange medium from the lungs continuously and/or cyclically, with delivery of gas to the lungs at a rate and volume independent of addition and removal of liquid.

FIELD OF THE INVENTION

The present invention relates to ventilator and heat exchange systems and, more particularly, to a "mixed-mode" gas-plus-liquid ventilator system using an endotracheal catheter to add and remove liquid ventilation or heat-exchange medium from the lungs continuously and/or cyclically, with delivery of gas to the lungs at a rate and volume independent of addition and removal of liquid.

BACKGROUND OF THE INVENTION

There are many situations in both human and veterinary medicine where it is desirable to rapidly induce or reverse hypothermia. There are also many clinical situations where it is essential to be able to rapidly reduce dangerously elevated body temperatures to near normal, as in the case of hyperthermia from heat stroke, drug or surgical anesthetic reaction, and febrile illness secondary to stroke, infection or other illnesses. In fact, it has been demonstrated in a number of studies that patient mortality is directly dependent on high temperature exposure time, and inversely dependent on the rapidity with which core temperature-is normalized.

Heretofore, the only clinically available means of achieving very rapid reduction in body temperature (or conversely, of re-warming from hypothermic temperatures) has been the use of invasive methods of heat exchange, such as cardiopulmonary bypass (circulating blood over a heat exchanger), or peritoneal and/or pleural lavage. A third, slower alternative for changing body temperature involves immersing the patient in a bath of heated or chilled liquid or gas (e.g. helium). The problems with these approaches are many:

1) External means of chilling or re-warming are relatively slow (<0.01° C. to 0.20° C./min), and produce a host of undesirable and sometimes lethal complications. In the case of cooling, the chilling of external body tissues results in vasoconstriction which interferes with the delivery and removal of oxygen, nutrients, and wastes from the peripheral tissues.

2) Re-warming from hypothermia by external means can cause a peripheral vaso-relaxation, hypotension, and effective hypovolemia, for which the cold-impaired heart and autonomic nervous system cannot compensate. Profound hypotension may develop, causing cardiac arrest and death, sometimes paradoxically in people presenting for apparently non-critical conditions.

3) Peripheral tissues being re-warmed recover the need for oxygen and metabolic substrates before the circulatory system and other organs can deliver them (since these organs are still cold and functioning marginally). This resulting imbalance between metabolic supply and demand results in the generation of large amounts of anaerobic waste products, including carbon dioxide and lactate, which decrease blood and tissue pH and result in severely disturbed homeostasis.

4) If external re-warming proceeds without inducing cardiac arrest, a second phase of risk occurs when "after-drop" is experienced. After-drop is a reduction in body core temperature during slow external re-warming. After-drop occurs as a result of peripheral vasodilation during patient re-warming, thus allowing large amounts of blood to flow through deeply chilled peripheral tissues, resulting in a seemingly paradoxical drop in body core temperature. After-drop can result in cardiac arrest during patient re-warming if the heart is cooled below its critical threshold for fibrillation. Though some controversy exists about the relative importance of this process in humans, it still remains of great concern to specialists in the field.

5) The use of invasive temperature modifying techniques such as peritoneal and pleural lavage, extracorporeal perfusion, or central venous cooling, are either not very effective (e.g. lavage techniques), or can be performed only in a medical setting by highly skilled, licensed practitioners (e.g. physicians). Most importantly, these techniques cannot be safely or reliably performed in the field by paramedics or other non-physician emergency medical personnel. In the case of techniques which require vascular access, many medical facilities possess neither the complex and costly equipment required to carry out such procedures, nor the highly skilled personnel necessary to perform such procedures. A particular problem with these methods is the need for bulky, complicated, failure-prone equipment which may be difficult to store in states of readiness (e.g. cardiopulmonary bypass apparatus). Technical errors and mechanical failures associated with extracorporeal techniques carry a high risk of morbidity, with such errors frequently resulting in neurological damage or loss of life.

The Lungs as a Gas Exchanger and Heat Exchanger

An alternative to invasive temperature modifying techniques would be to use the large surface area of the lungs as a heat exchanger. Nearly all of the cardiac output (i.e., all blood flowing to the body) flows through the lungs, and since the lungs possess a surface area of at least 70 square meters, they form an ideal heat exchanger that would allow for rapid core cooling and re-warming of the patient without the problems associated with the techniques previously discussed. In addition, since the lungs are accessible via the trachea, the relatively benign maneuver of endotracheal intubation (a skill universally possessed by paramedics) allows for quick field access to this powerful heat exchanger. The potential utility of the lungs as a heat exchanger was first recognized by Clark and Gollan in the 1960's, when they used the perfluorochemical FX-80 to demonstrate the concept of total liquid breathing in mice. The concept of using the lungs as a heat exchanger for therapeutic purposes was first proposed by Shaffer et al. in 1984, using total liquid ventilation and the fluorocarbon "Rimar 101" (Rimar Chimica S.p.A., Vincenza, Italy).

Heat exchange in the lungs using liquid ventilation is superior to gas ventilation because at standard temperature and pressure, gases such as oxygen and air have only approximately a 2200th of the volumetric specific heat capacity of water. Thus, under ordinary circumstances the lungs serve as a relatively poor heat exchanger if only gaseous media are used. This includes the use of the highly conductive—low viscosity gas mixture of oxygen and helium (Heliox). The high conductivity of Heliox makes it far more efficacious as a heat exchange medium under high pressure conditions where its specific heat capacity is greater that at normal pressures; however these conditions are of little relevance to most clinical situations.

The Basics of Liquid Ventilation

Liquid ventilation involves the breathing of gas-carrying liquid as the medium of gas exchange within the lungs. Since the first liquid ventilation experiments (1950's) in mice using super-oxygenated saline, several liquid media for ventilation have been studied. The class of agents currently optimized to function as liquid breathing media are the fluorocarbons (containing only fluorine and carbon), and the organic perfluorochemicals. (PFCs). PFC compounds contain elements other than fluorine and carbon, with fluorine or other halogens comprising the majority of peripheral moieties. within the molecule. As a class, PFC compounds comprise molecules that are relatively insoluble in either water or lipid, and are more-or-less chemically and pharmacologically inert. PFCs do not dissolve native lung surfactants, and are far less injurious to the lungs than any known silicone or water-based solution.

Total Liquid Ventilation

Historically, the first mode of liquid ventilation studied was total liquid ventilation (TLV). In TLV all of the gas within an animal's lungs is replaced with liquid, and each breathing cycle (tidal volume) is composed entirely of liquid medium. While this modality holds promise in deep-sea diving research, it has not yet been used in humans.

In heat exchange, each TLV breathing cycle provides a certain volume that can be passed through the lung heat exchanger. As noted, the advantage of TLV (as opposed to gas exchange) for heat exchange, is that liquids such as PFCs have a specific heat capacity several thousand-fold that of gas at normal pressure. Despite this advantage, total liquid ventilation suffers from a number of drawbacks:

1) In TLV it is necessary to completely eliminate air from the animal's lungs and the ventilating circuit, because PFCs do not pump well in many systems due to "vaporlock". The maneuvers necessary to clear all gas from the system are problematic and time consuming.

2) Due to the increased viscosity of liquids (PFCs are 80 times more viscous than air), the number of liquid breaths attainable per minute is sharply constrained compared to air ventilation. Typically, no more than 5 to 7 liquid breaths per minute are possible (Shaffer T H, et al., 1984). This is approximately one forth the usual rate at which tidal gas volume ventilation occurs in animals of this size.

3) In addition, the maximal liquid ventilatory "minute volume" (dV/dt) is more tightly constrained in TLV making adequate gas exchange problematic in situations where oxygen demand is high, and the need to remove $CO_2$ is great. Carbon dioxide removal is a particular problem in TLV because PFCs have a lower carrying capacity for $CO_2$ at physiologic partial pressures (which cannot be changed much), than they have for $O_2$ (which is easily deliverable at artificially high partial pressures).

Miyamoto and Mikami in 1976 calculated that the resting man produces normally 192 mL/min of $CO_2$ (S.T.P.). This level of $CO_2$ production would require TLV (PFC) ventilation volumes of about 4 L/min (or about 70 mL/kg/min). Although this is only 70% of the normal gas ventilatory flow for a resting adult, it is near the upper limit of flows that can be accomplished at normal pressures in TLV (Kylstra, 1974). The higher peak and mean ventilating pressures necessary to move the amount of liquid required for $CO_2$ exchange in TLV would expose the lungs to an increased risk of barotrauma (pressure injury) and volu-trauma (over-distention injury).

During higher than normal $CO_2$ production rates (e.g. disease), TLV would clearly not be adequate for $CO_2$ removal. Examples of high $CO_2$ (hypercapnic) states are 1) increased metabolic states (e.g. cancer, infection, burns), 2) states of physiologic stress (e.g. hyperthermia, agitation), and 3) post-ischemic conditions where substantial metabolic debt has been incurred and the need to rapidly unload $CO_2$ and deliver large amounts of $O_2$ are essential. Such hypercapnic/hypercarbic states are also frequently present in shock due to sepsis or trauma, and thought to be due to both an increased production of $CO_2$, and a decreased elimination of $CO_2$ due to low blood flow or pulmonary edema.

In anesthetized, paralyzed, normothermic dogs, TLV is capable of maintaining steady-state gas exchange with adequate $O_2$ delivery and $CO_2$ removal. However, TLV is not adequate to steady-state $CO_2$ removal under basal metabolic conditions in smaller animals with higher specific metabolic rates, such as guinea pigs. As Matthews and co-workers document (1978), the parameters for maintaining normocapnia in anesthetized beagles are narrow, even under basal normothermic metabolic conditions. In this study, as liquid ventilation rates were increased from 2.8 to 5.6 liquid breaths per minute, and alveolar ventilation was increased from 574 to 600 mL/min/animal (increase of 4%), the $paCO_2$ continued to increase until dangerous hypercapnia occurred. The authors suggested that this increase was due to a 2% drop in liquid-alveolar ventilation, however using their own formulas and data, we have calculated that the dogs receiving higher ventilation rates actually have higher rates of alveolar ventilation (dVa/dt). These results would seem paradoxical until consideration is given to the inverse relationship of $paCO_2$ to alveolar ventilation, a relationship which holds only if equilibrium between blood and "alveolar" $CO_2$ (actually, alveolar and small airway $CO_2$) is reached for each breath. The fact that high TLV ventilatory rates resulted in rising $paCO_2$ in this paper despite increased "alveolar" ventilation (dVa/dt), indicates that the high ventilatory rate used was too rapid for blood/airway $CO_2$ equilibrium to be reached. This behavior is a limitation of the diffusion speed of $CO_2$ in PFC in the small airways, conduits that are constructed on a size scale for "gas-in-gas" diffusion, but not "gas-in-liquid" diffusion.

Diffusion limitations on $CO_2$ removal in TLV models have been noted by several research groups. This diffusion limited failure of $CO_2$ equilibrium acts to increase "diffusion dead space" and in practice places even more constrictive limits on usable ventilation rates with perfluorocarbon (PFC) liquids in TLV. These limits are in addition to those already imposed by the viscosity of the fluid itself. For example, Koen and Shaffer found that TLV in young cats showed maximal $CO_2$ elimination at a ventilatory rate of 3 to 3.5 breaths per minute. Decreasing $CO_2$ clearance occurred at lower rates, due to insufficient ventilation, whereas decreased $CO_2$ clearance occurred at higher rates due to $CO_2$ diffusion limitations with short liquid dwell times. In summary, at higher TLV ventilatory rates, equilibrium in $pCO_2$ between alveolar blood and freshly inspired liquid in the small airways is not reached. For this reason, liquid alveolar ventilation in TLV cannot be arbitrarily increased, for fundamental reasons involving pressures limits on high liquid flows, and also diminishing gas exchange at rapid liquid flow rates.

4) PFC viscosity (pressure/flow) also places a limit on the rate at which heat can be extracted from an animal or patient using TLV. In addition to the $CO_2$ diffusion limitation, there is indirect evidence suggesting that thermal equilibrium is not reached between blood and liquid in small airways at high TLV "alveolar ventilation" rates. Thus, there appears to be a heat-diffusion limitation to TLV that is analogous to the $CO_2$ diffusion limitation.

This phenomenon may explain why Shaffer's TLV cat studies failed to achieve concomitant increases in the rates of animal core cooling, when significantly greater PFC temperature gradients were used (Shaffer T H, et al., 1984). In Shaffer's report, it was found that decreasing PFC infusion temperature from approximately 20° C. to about 10° C. (from $\Delta T=15°$ C. to $\Delta T=24°$ C.), resulted in cooling rates increasing from 0.13° C./min (7.8° C./hr) to 0.15° C./min (9.0° C./hr), a change of only 15%. This 15% increase occurred despite an increase of $\Delta T$ equal to 60%. These results suggest a sharp decline in the efficiency of heat extraction with increased $\Delta T$ at higher TLV ventilation rates (in this experiment, rate was increased from 4.5 to 5.3 liquid breaths/min).

In Shaffer's study, the authors calculate from PFC inspiration and expiration temperature differences, a 96% increase in heat extraction per kg from their animals at the 10° C. PFC infusion temperature versus that calculated at 20° C. However, the fact is that this increase in heat extraction does not show up in the rate of body core cooling (15%), to which it should be proportional. This indicates that Shaffer's calculations of heat removal performed on the basis of integrated measurements of expired fluid temperatures must have been in error. As further evidence of this error, calculations of expected cooling rates of animals used in this study (using a reasonable 0.8 cal/g/° C., or kcal/kg/° C. average specific heat capacity for the body), indicate that up to half of the heat extraction calculated by PFC temperature differences in this experiment are unaccounted for even at the fastest cooling rates. For example, an animal with an average 0.8 kcal/kg/° C. specific heat capacity, cooling at the reported rate of 9.0° C./hr, could theoretically give up heat at a rate no faster than (0.8 kcal/kg/C)(4184 J/kcal)(9 C/hr)=30,124 J/kg/hr. However, Shaffer's experiment reports on the basis of temperature readings of PFC infused and expired, the extraction of 65,637 J/kg/hr. It is likely that the difficult integration of [expired fluid temperature] versus [fluid volume] curve for this experiment was in error by a factor of 2.0. For examples of experiments in which integrated cooling rates calculated from PFC temperature differences match actual animal body cooling, see the canine experiments using hand controlled infusion below. The authors of the present patent have found that at rapid (machine-controlled) liquid infusion and removal rates, peak fluid temperatures do not accurately reflect volume-averaged fluid temperatures, or fluid heats.

Partial Liquid Ventilation

The second mode of liquid ventilation to be studied was Partial Liquid Ventilation (PLV). In PLV, the subject's lungs are partially (usually to functional residual capacity (FRC) of 30 mL/kg of body weight or about ⅓rd of total lung capacity (assumed hereafter to be 90 mL/kg) loaded with PFC liquid. In PLV, PFC liquid loading is accompanied by conventional mechanical ventilation using a standard gas ventilator at normal gas rates and tidal volumes. Since the breaths are delivered as gas, PLV allows for the number of breaths per minute, and alveolar ventilation rates, to be set much closer to the physiologically acceptable and desirable rate. PLV can even be used with high frequency gas ventilators, and can accommodate a wide range of metabolic states in which the demand for $O_2$ delivery and $CO_2$ removal is greater than that of basal states. PLV is currently being tested in human clinical trials.

During PLV, gas exchange occurs across material boundaries at two locations: 1) between the PFC liquid and the circulating blood (across the alveolar membrane), and 2) between the PFC liquid and the ventilating gas in the airways, where a short-lived turbulent foam of PFC and ventilating gas is created. The low viscosity of this PFC foam allows it to reach briefly into the small airways of the bronchial tree with each breath and helps explain the complex and poorly understood mechanism of PLV gas exchange. The turbulent mixing of PFC foam may also explain the newly appreciated heat exchange properties of this modality (as well as those of Mixed-Mode Liquid Ventilation, discussed next). The mixing of air and gas in small airways, which will be discussed more fully later, appears to be key to improving the heat transfer limitations of TLV. We believe that the mixing of PFC and gas disrupts laminar liquid (PFC) flow in small airways by introducing turbulence to the fluid, thereby improving the small-scale (small airway) convection necessary for maximal heat transfer rates.

We introduce in this document the novel application of the unique mixing features of PLV to assist in core body-heat transfer. Specifically, the primary clinical utility of PLV has heretofore been in the treatment of adult and neonatal respiratory distress syndromes. In these pathological conditions, PFC (among other salutary effects) moves downward in the bronchial tree due to its high density (1.8 to 2.0 times that of water) opening alveoli which are closed as the result of pulmonary edema (fluid in the dependent portions of the lungs).

Significant heat transfer has not been documented using standard PLV because PFC has been historically loaded slowly into the lungs, and once in place, has not been retrieved (cycled). Using a single dose of ⅔rds or more of total lung capacity (TLC) of cold (slightly below 0° C.) PFC (60 mL/kg), it is possible in the dog to achieve a uniform core cooling of approximately 1.5° C. with only modest injury from baro- and volu-trauma (see Example I data in Part II below). Further cooling of the test subject does not occur unless a new load of cold PFC is instilled into the lungs. Thus, the use of PLV and single PFC loads, even to extreme volumes (i.e., those approaching TLC) is not a viable means for achieving even moderate, controllable, or lasting hypothermia.

Note on the Difficulty of Re-warming

Single loads of PFC are not sufficient to induce significant or lasting hypothermia. This problem is compounded more so when contemplating PLV for hypothermic subject re-warming. This is because there are two unavoidable limitations on how warm the delivered liquid can be. The first is that an absolute temperature limit of 42° C. exists beyond which hemolysis and acute thermal injury to tissue occurs. The second limit involves the temperature gradient ($\Delta T$) between the blood and the PFC liquid, which if significantly greater than 5° C., exposes the subject to the risk of gas bubble emboli. This risk occurs because the solubility of nitrogen and other gases in plasma is greater at cold temperatures. Upon re-warming chilled blood, the nitrogen (and other gases) come out of solution, forming gas bubbles which can then embolize both the arterial and venous circulation. This same phenomenon occurs in nitrogen saturated. tissues warmed at very rapid rates, and forms the pathological equivalent of the "bends" experienced by deep sea divers breathing nitrogen-containing gas as they decompress too rapidly.

These temperature gradient constraints on warm liquid delivery to hypothermic subjects sharply limits the maximal therapeutic rate of heat transfer achievable by PLV used for re-warming. For example, it is not possible to deliver liquid that is 35° C. above body temperature in a subject still warm enough to have a beating heart (typically 25° C. or above). In contrast, it is possible (see Part II) to safely deliver liquids that are 35° C. cooler than body temperature. Thus, the $\Delta T$ when re-warming from modest but life-threatening hypothermia (i.e., 27° C.) is less than 30% of that which can be achieved during the therapeutic induction of hypothermia.

SUMMARY OF THE INVENTION

One aspect of the present invention is a mixed-mode liquid ventilation (MMLV) method for gas and/or heat exchange in the lungs (human clinical and veterinary applications). The MMLV method allows mixing of gas and liquid in the small airways of the lungs, producing small-scale liquid mixing in a convection-like process, rapid return of fluid from the lung periphery, and more rapid and efficient transfer of heat, and dissolved gasses, during the practice of ventilation with liquids.

In one embodiment, nitric oxide or nitric oxide donors are administered to facilitate gas and heat exchange.

In another embodiment the gas is helium.

In a further embodiment the liquid ventilation medium is a perfluorocarbon or perfluorochemical.

A further aspect of the present invention is a method of inducing small-scale mixing of liquid heat exchange ventilation media, using other known ventilation methodologies, alone or in combination. These specifically include known types of gas ventilation, including high frequency oscillating ventilation.

Another aspect of the invention is the use of MMLV to treat hypothermic pathologies by heating said liquid ventilation medium, and thus increasing body temperature.

A further aspect of the invention is the use of MMLV to induce hypothermia for medical purposes, or to treat hyperthermic pathologies, by cooling said liquid ventilation medium, and thus decreasing body temperature. In this embodiment, liquid ventilation media may be infused at temperatures as low as –10 C. This is made possible by the presence of thermally buffering PFC already in the lung, as well as the fact that PFC may be a minor volumetric component of the ventilation mix in MMLV, and small infusions are warmed to temperatures above 0 C before freezing or chilling damage can be done to tissues.

Another aspect of the invention is a method of preserving biological material, for example beating-heart cadaveric preparations, using the rapid cooling available with MMLV.

A further aspect of the invention is a method for increasing the efficiency of CPR using MMLV.

A final aspect of the invention is an automatic apparatus for MMLV, which connects to the lungs via the bronchi and uses a computer to control loading and unloading of said oxygenated liquid and gas so that mixing occurs; and also makes use of the computer to insure that pressure limits are not exceeded, and gas ventilation proceeds in a way which most rapidly induces removal of fluid heat exchange media. In this embodiment, the computer controls liquid infusion in such a way as to maximize time integrated arterial/venous temperature differences, for best cooling rates, subject to ventilatory constraints.

In a typical embodiment said computer controls the liquid ventilatory volume delivered and removed (dV/dt) to be about 10% to 50% that typically necessary for gas ventilation.

In a further embodiment the apparatus has a cold reservoir where pre-cooled PFC may be stored.

In another embodiment the apparatus has a heat exchanger for PFC.

In another embodiment the apparatus has an active liquid ventilation system, which may employ a canula able to remove liquid at the same time gas breaths are delivered. Gas and liquid are typically infused and removed through separate concentric tubes in many of the most efficient implimentations of the invention, but may be removed through the same tube.

Further objects, features, and other aspects of the present invention become apparent from the ensuing detailed description, considered together with the appended figures.

BRIEF DESCRIPTION OF THE FIGURES

FIG. 3 shows canine tympanic, rectal, venous blood, and aortic blood temperature as a function of time from Example 2, showing multiple cycles of loading and unloading of chilled PFC at –1° C. from the lungs. This example illustrates PFC removal using a suction reservoir, illustrating the full principle of mixed-mode liquid ventilation (MMLV). A 25.7 kg anesthetised, intubated, and paralyzed dog was given infusions of PFC at a maximal rate of 6 mL/kg/min. Temperatures were measured as in FIG. 1a.

FIG. 4 is shows a table of PFC liquid infusion volumes, measured temperatures of these volumes, and the calculated difference in their heat contents, from example 2. This table illustrates the qualitative and quantitative heat transfers involved in the MMLV technique.

FIG. 5 shows a graph of canine tympanic, central venous, aortic, rectal, and PFC suction temperatures from Example 3 of a 24.5 kg dog when infusion and suction rates are increased to 16.7 mL/kg/min. Temperatures were measured as in FIG. 1a.

FIG. 6A is an illustration of a device for Mixed-mode Liquid Ventilation (MMLV). Its use is in manual mode (manual valve control) is illustrated in Examples 2 through 6. Its use in full computer-valve-control mode is illustrated in FIGS. 10a and 19.

FIG. 7 shows canine tympanic, rectal, venous, and aortic blood temperature as a function of time from Example 4. A 17.3 kg dog was used with an infusion rate of 45 mL/kg/min, increased by a factor of 2.6 from that shown in FIG. 3. Illustrated is a procedure which cooled the animal by 12 C over 30 minutes, for net cooling of 10 C after thermal equilibration. This animal survived long-term, without evidence of respiratory damage. Temperatures were measured as in FIG. 1a.

FIG. 8 shows canine rectal temperature as a function of time from Example 6 of a 30 kg dog (a much larger animal than illustrated in FIG. 7), when the infusion rate was maintained at 46 mL/kg/min, and suction rates were increased to accommodate larger absolute volumes. Temperatures were measured as in FIG. 1a.

FIG. 9 shows rectal, tympanic, venous, aortic, and suction temperature as a function of time from Example 6, using a 19.8 kg dog with PFC infusion rate of 46 mL/kg/min. This example illustrates temperature relationships during the fastest manual cooling cycle rates. Temperatures were measured as in FIG. 1a.

FIG. 11a shows PO2 results of arterial blood gases drawn every 2 mintues in 4 animals cooled by rapid manually controlled PFC lavage, vs 2 animals given the same manual lavage with body temperature PFC. Temperatures are measured as in FIG. 1a.

FIG. 11b shows pO2 results of arterial blood gases drawn every 2 mintues in 3 animals cooled by rapid machine controlled PFC lavage, vs 2 animals given the same maschine lavage with body temperature PFC. Temperatures are measured as in FIG. 1a.

FIG. 11c shows paCO2 results of arterial blood gases drawn every 2 mintues in 5 animals cooled by rapid manually controlled PFC lavage, vs 2 animals given the same manual lavage with body temperature PFC. Temperatures are measured as in FIG. 1a.

FIG. 11d shows paCO2 results of arterial blood gases drawn every 2 mintues in 3 animals cooled by rapid machine-controlled PFC lavage, vs 2 animals given the same lavage lavage with body temperature PFC. Temperatures are measured as in FIG. 1a.

FIG. 16a shows the same study and variables graphed for a different canine being lavaged in the same way with body temperature PFC, in order to eliminate the temperature variable.

DETAILED DESCRIPTION OF THE INVENTION

Figure 1:
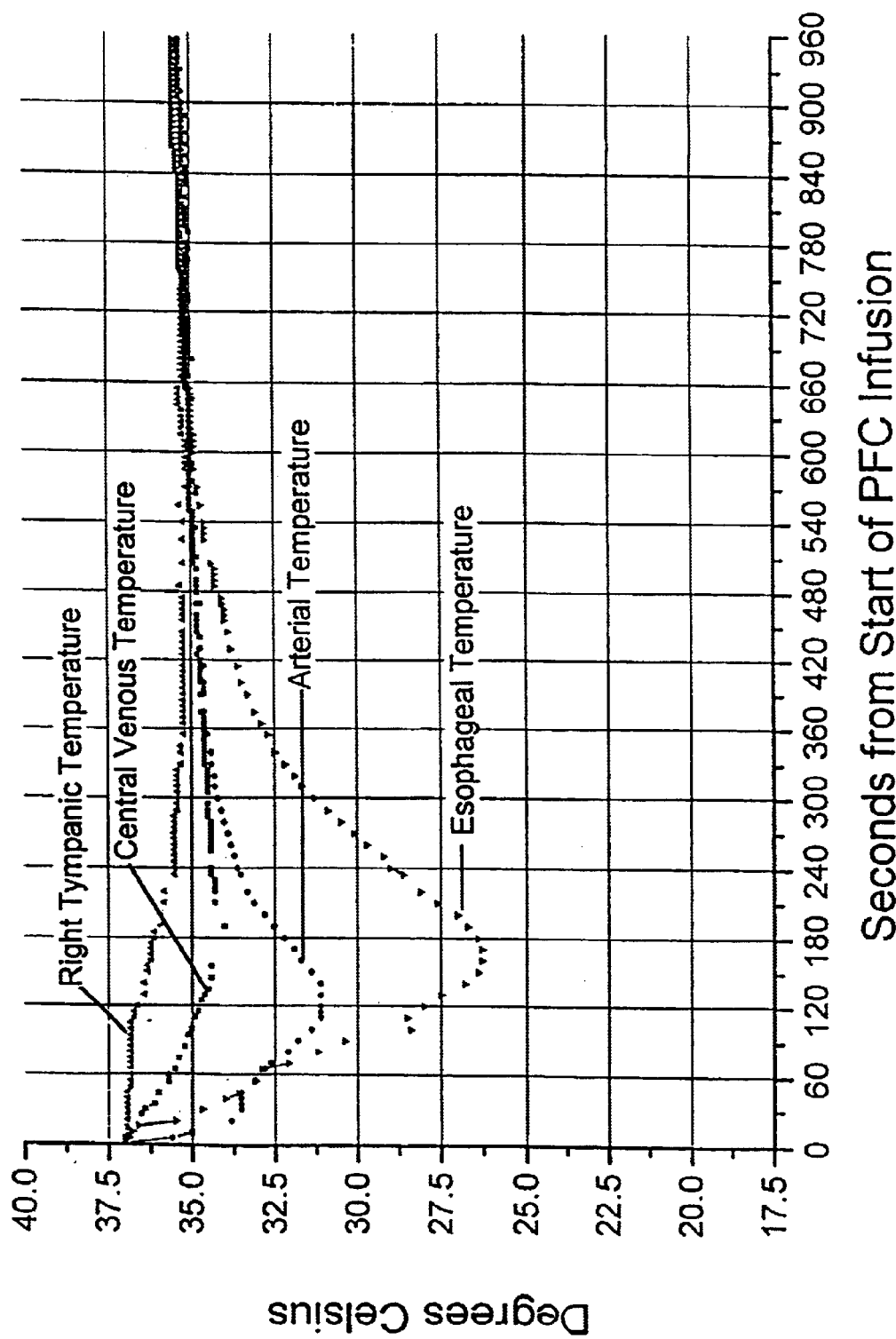
FIG. 1 shows a graph from Example 1 of canine tympanic, central venous blood, aortic arterial blood, and esophageal surface temperatures over time, during mixed gas and liquid ventilation, in which a single loading volume of liquid PFC is delivered into the endotracheal tube. PFC as a single load of 76 mL/kg of PFC at a temperature of 4.4° C. is loaded into the lungs over 145 seconds.

We have developed a new method for gas and heat exchange termed Mixed-Mode Liquid Ventilation. Additionally, we have developed an apparatus which allows for heating and cooling by lung lavage while causing the least damage during the process. The technique and apparatus also may be used with liquid ventilation to increase $CO_2$ removal from the body, when liquid media have been introduced to the lungs primarily for heat exchange purposes. The technique and apparatus also take advantage of our discovery that gas ventilation may be-used to facilitate recovery of liquid in perfluorocarbon lung lavage, as well as the novel discovery that the non-thermal convection (transport of dissolved gas by liquid mass flow not related to differential density) that occurs with mixing of liquid and gas in the lungs' small airways, allows for faster and more efficient heat and gas exchange.

Mixed-Mode Liquid Ventilation

A technique is needed to achieve better and more efficient cooling or re-warming using liquid ventilation. This technique must allow for the continuous addition and removal of PFC (as liquid or aerosol) from the lungs, while also allowing for the delivery of gas breaths via a mechanical ventilator or other means at a rate independent of the input and removal of PFC liquid from the lungs is required. The reason for this is that while liquid ventilation is performed to control addition or removal of heat, gas ventilation must also occur independently to allow for adequate oxygen delivery and carbon dioxide removal. Furthermore, the combination of these techniques affords a previously un-described synergism to occur (as set forth herein), in that gas ventilation assists liquid removal from the lungs, and that gas-induced mixing of fluids in the small airways is required to obtain optimum heat transfer efficiency during short liquid ventilation cycle times. In a new approach to PLV, our experiments suggest the possibility of utilizing some elements of PLV to facilitate heat exchange. We have discovered that when optimized, PLV by virtue of PFC-gas bubble induced liquid convection, possesses both excellent heat and gas exchange properties.

That gas-bubble-induced PFC mixing (small-scale convection, not necessarily thermally induced, also called "forced" convection) must occur in PLV in order to obtain maximal efficiency of heat transfer in liquid ventilation, is not obvious. It is also not obvious that independent control of gas ventilation is necessary for the most rapid return and cycling of liquid/gas mixtures. A novel method of optimized gas and heat exchange with gas plus PFC liquid ventilation is detailed below. Over four years of work was required to develop the mechanics involved in "Mixed-Mode Liquid Ventilation" (MMLV) and to describe the general principles by which both heat exchange and gas exchange can proceed both simultaneously and independently from each other.

Our solution to the shortcomings of TLV and PLV (detailed below), was to develop a modality whereby PFC (which is appropriately chilled or warmed) could be delivered to the lungs, either continuously or intermittently, while conventional mechanical ventilation proceeded in a variable, but coordinated fashion. In the following discussion, the specifics of combined gas/PFC liquid ventilation and heat exchange, termed "Mixed-Mode Liquid Ventilation" will be outlined, and key experiments will be used to illustrate the modality's power. Finally, a prototype system for "field" MMLV application will be revealed and differentiated from prior art.

The Special Importance of PFC/Gas Mixing in the Periphery of the Lung

Before Mixed-Mode Liquid Ventilation (MMLV) is explained, further attention should be drawn to a key phenomenon which is not taken advantage of in prior art in liquid breathing heat transfer (i.e., Total Liquid Ventilation/ TLV heat transfer). This phenomenon occurs because PLV induces air and gas mixing in not only large airways, but also in small and extremely small airways.

Ordinary models of gas and liquid foams, based on high surface-tension mixtures of water and air, do not suggest the fineness of the gas micro-bubbles which rapidly travel to the extreme periphery of the lung in PLV. The radiopacity of the clinically used brominated PFC perflubron (Liquivent™) has prevented this micro-bubble formation phenomenon from being viewed directly by fluoroscopy. However, this phenomenon may be viewed directly by fluoroscopy if a non-radiopaque PFC (one which uses no halogen other than fluorine) is used. In such circumstances, each breath of PLV shows a flash of micro-bubbles rapidly (<1 second) moving to the periphery of the lungs. Liquid/gas mixing and the resulting turbulence and disruption of insulating laminar flow from such a process is profound, and due to the unique fluid properties of PFCs, is somewhat outside ordinary experience. However, gas-induced "convective" mixing of PFC in small airways probably underlies not only the success of PLV in removing $CO_2$, but also the increased efficiency of PLV in heat transfer.

This relative efficiency has not been previously appreciated in PLV, partly because PLV, though now backed with significant clinical trial experience for respiratory disease, has not been used for heat transfer. As for TLV, it has not been used in humans at all (except briefly in a handful of test subjects), so that diffusion dead space limitations resulting from PFC in small airways is not yet encountered clinically. If expected on theoretical grounds in PLV, its absence may have been explained away in clinical trials on the grounds that many alveoli are not filled with PFC in this modality. However, radiographically the opposite appears to be the case, and especially in use of PLV with high frequency ventilation, it seems clear that essentially all peripheral airways are filled with PLV at all times, and yet TLV-type diffusion barriers still do not occur. Non-thermal, or "forced" convective small-scale liquid-mixing from high frequency oscillation induced by such ventilators may be the answer to a question which has not been asked.

The phenomenon of induced small-scale forced-convection cannot be fully utilized for heat transfer efficiently unless PLV is combined with certain techniques for rapid PFC liquid infusion and removal, as detailed below, in the novel technique referred to herein as Mixed-Mode Liquid Ventilation. Mixed-Mode Liquid Ventilation (MMLV) is different from TLV and PLV, in being optimized for heat transfer.

Exposition of Mechanics of Mixed-Mode Liquid Ventilation

In Mixed-Mode Liquid Ventilation (MMLV), conventional mechanical ventilation is initiated via endotracheal intubation or the use of other means to isolate the airway from the gastrointestinal system, and allow application of positive pressure to the lungs (i.e., the esophageal gastric tube obturator airway (EGTA), the Combitube airway, etc.). Then, chilled or warmed (relative to the subject's desired body temperature) PFC is progressively loaded and unloaded from the lungs using a mechanical pump(s). The PFC may be loaded in liquid or aerosol/spray form, and loading may be done continuously or intermittently (timed with inhalations). The technique works best when the PFC is recycled through a gas-exchanger as well as a heat exchanger, but extracorporeal PFC gas exchange is not an absolute requirement in many situations using MMLV.

If very rapid rates of heat exchange are desired, 10 to 20 mL/kg of PFC is loaded into lungs already filled to ~⅓ of total lung capacity (equal to ca. 30 mL/kg or ~FRC). This brings total PFC load to a maximum of less than ⅔rds of total lung capacity (⅔rds of 90 mL/kg=60 mL/kg), and typically less than 60% of total lung capacity. As soon as the liquid has been loaded, it is then unloaded again, as rapidly as possible, to FRC. Heat transfer from liquid is rapid enough with MMLV that use of deliberate liquid dwell times are usually not efficient. Liquid loading and removal rates will be discussed below, but for maximal heat transfer rates, liquid alveolar "minute volumes" (liquid alveolar ventilation) typically averages 25 to 33% of those for gas.

As liquid is loaded into the lungs, the volume of gas delivered with each mechanical breath is decreased, using a pre-determined peak inspiratory flow pressure as the cut-off point. Current experience with a canine model indicates that the maximum peak airway pressure which is tolerable without inducing significant volu- and barotrauma to the lungs is ~40 cm water (29 mmHg or Torr). These pressures occur at the ends of small (10 mL/kg) gas breaths, when the lungs already hold 40 to 50 mL/kg of PFC. The occurrence of higher positive airway peak pressures can be particularly avoided by use of small (<10 mL/kg) PFC infusions at rapid rates (>50 mL/kg/min), but these rapid techniques require machine control of infusion and suctioning (see examples below).

As liquid is suctioned from the lungs after the rapid phase of heat exchange has occurred, the tidal volume of gas delivered to the lungs should be increased as the liquid is progressively removed. When the lungs are fully loaded with PFC to 60 to 70% of total lung capacity, mechanical gas breaths must be very small in volume to prevent overpressure. When the lungs are fully unloaded of easily suctioned PFC, gas ventilation can occur at a maximally effective rate and volume needed for $CO_2$ removal. In MMLV, particularly during cooling,. $CO_2$ is removed by both PFC and gas ventilation. PFC infusion/suction cycle ratios may be adjusted, however, to increase $CO_2$ removal in situations where this is especially needed. Increasing the time during which the lung is unloaded of fluid allows for best time efficiency in $CO_2$ removal, at a given maximal airway pressure.

Heat transfer considerations suggest that most of a fresh load of PFC delivered to the lungs reaches the small airways after a few gas ventilations, since the rate at which this fraction of PFC reaches thermal equilibrium with previously infused PFC, and with blood flowing through the lungs, has been found to be very rapid, with the equilibration half-times being much less than 1 minute. Again, this is probably largely due to the assisted convective mixing of cold and warm fluid due to gas-induced stirring seen in MMLV. Rapid-phase heat equilibration is complete by the end of PFC loading at rates of loading up to 6 mL/kg/min, since the average temperature of the expired PFC after a loading cycle does not increase, whether zero dwell time is used or an additional dwell time of up to one minute after loading is allowed. At these rates, average temperature of a removed PFC load remains constant at about 3° C. below the animal's core temperature during short dwell times, because of the contribution of the dead space volume of cold liquid in the large airways, which liquid requires a much longer equilibration time to warm (see Example 2, FIG. 3 below).

At much faster PFC infusion rates, from 16 to 45 mL/kg/min (see FIG. 5 and FIG. 9), and loads of 23 mL/kg, the temperature difference between end-expiratory PFC and animal core temperature increases from approximately 5° C. to 7.5° C. This is presumably due to incomplete temperature equilibration within body thermal compartment system #1, which is composed of blood, lung tissue and PFC in the smaller airways (see explanation of thermal compartments below). However, this effect is small within this range of thermal load, and these figures indicate surprisingly small decreases in heat transfer efficiency (from PFC to subject, or vice versa) with increasing total rate of PFC "lavage." In this series, using MMLV, efficiency varies from 92% at 6 mL/kg/min, to 77% at 50 mL/kg/min (30 second infusions), to 57% at 50 mL/kg/min (10 second infusions).

A time of 30 seconds for infusion, and 15 to 20 seconds for liquid removal is typical for experiments at our fastest manually controlled liquid loading and unloading rates (see experiment 7 below). A typical algorithm for manually controlled MMLV for a medium-sized dog (20 kg) is to load PFC at 40 to 50 mL/kg/min and unload PFC at approximately 80 mL/kg/min. For faster loading and unloading rates, allowing lower pressures and more time for gas ventilation, machine control of PFC infusion and suction is required. FIG. 10*a* shows cooling rates for 3 animals cooled with machine infusions of 8 mL/kg (50 ml/kg for 10 seconds) followed by machine-controlled suction of the same PFC volume, for 4 to 7 seconds. These animals are compared in cooling rate with 5 animals cooled using the identical infusion rate (50 mL/kg/min), but with 30 second loads and comparable suction times. All of these animals received essentially the same amount of cold fluorocarbon during 18 minutes, but using infusions of FC of $\frac{1}{3}^{rd}$ the size resulted in about a 25% loss of efficiency in heat transfer. Some of this loss occurred in non-insulated liquid infusion lines, where heat leaks between infusions became important for short infusions, and induce a kind of "heat dead-space," akin to the ventilator gas line dead space which becomes important during small tidal volume ventilation.

Theoretically Expected Cooling Rates

The PFC employed for most of the experiments reported here is 3M Company's "FC-75," a proprietary mixture of fluorinated hydrocarbons reported to consist mostly of perfluoro-butyl-ietrahydrofuran (CF3-CF2-CF2-CF2-C4 F8O), and which has a volumetric specific heat capacity of 0.45 cal/mL/° C. A loading rate of 45 mL/kg/min (30 seconds) followed by an unloading rate of 80–90 mL/kg/min gives a recycled liquid minute volume of 22.5 mL/kg infused and removed, averaged out over 45 seconds (time for liquid entry and removal). This results in an average PFC recycling rate of 22.5 mL/kg÷(0.75 min)=30 mL/kg/min (we will detail a number of exmples below with comparable infusion and net recycling rates but differing infusion loads). Since cold PFC enters the animal at 3° C. and leaves at about 28–33° C. (as the subject cools from 38° C. to 33° C.), this represents heat removal at a rate of 30 mL/kg/min×0.45 cal/mL/° C.×27° C.=365 cal/kg/min=0.405 kcal/kg/min. For an animal with a mean body specific heat capacity of 0.70 kcal/kg/° C. this gives an expected cooling rate of (0.365 kcal/kg/min)÷(0.70 kcal/kg/° C.)=0.52° C./minute. In practice, maximal brain/tympanic cooling rates of up to 0.43 C/min have been achieved with this technique (Example 7, FIG. 10), and faster rates are in theory achievable with colder PFC and faster PFC infusion. In our studies we typically cool animals to an equilibrium temperature 5 to 10 C below initial body temperature (representing an initial drop in core temperature of 7 to 12 C). Rates of ~0.5° C./min represent about ½ of the cooling rates available on cardiopulmonary bypass (CPB), but are superior to cooling rates achieved with all other techniques, both invasive and non-invasive. They are also, as a matter of practicality, far superior also to "time from intent to treat" CPB rates, since times to achieve machine connection for the average patient must here be realistically added into the equation.

The fastest cooling rates reported here are 3 times the rate achieved by Shaffer's group in TLV cooling of cats (Shaffer TH et al., 1984). Note the fact that the fastest tested rates of cold PFC recycled with MMLV, as detailed below (30 mL/kg/min recycled) are less than ½ of those typically employed in TLV as applied by Shaffer et al. at their coldest liquid infusion temperatures of 10 C (minute volumes in Shaffer's study are ~56 mL/kg/min), and yet the cooling rate achieved with the MMLV technique is far greater. This is due to the relatively poor heat extraction and poor temperature equilibration of PFC in the lungs with TLV, especially at higher TLV rates, causing effective loss of cooling efficiency and power. This is suggested in Shaffer, et al. (1984) by the large 12° C. to 15° C. difference between their experimental animals' body temperatures and the temperature of their expired PFC. (Moreover, as previously noted, this difference should have been even greater, given the unexpectedly slow rate of body cooling reported).

At lower ventilation rates in TLV, cooling and heating efficiency improve somewhat, but now $CO_2$ removal becomes problematic. Heat removal never approaches maximum efficiency in TLV because the needed ventilation rate in TLV is apparently too high to allow good heat equilibration between the PFC already in the functional residual capacity of the lungs, and the cooled or warmed PFC delivered in a given tidal volume breath. The process of PFC heat equilibration and heat transfer in TLV is convective and by mechanical fluid transport (ie, circulation, bubble or vibration mixing) for fluids on larger scales (large airways) but increasingly by conduction at small-scales (small airways and alveoli). Convective heat transfer in small airways in TLV is impaired by laminar flows which inhibit the warmed or cooled PFC, which has been delivered into the large airways, from being mixed rapidly with the PFC already present in small airways. Mixing (and convective heat transfer at smaller scales) is greatly facilitated when micro-bubbles of gas (from a gas ventilatory breath) initiate small airway liquid turbulence. The solution to the problems of heat and gas exchange in liquid ventilation is therefore to introduce gas into liquid ventilation heat exchange systems (thereby creating micro-bubble small-scale non-thermal fluid mixing), and also to vary PFC and gas delivery independently to the lung, so that each can be used at their maximally efficient and least traumatic delivery and removal rates. This is novel. A description of this general method is described below with preferred embodiments.

Description of Practical Protocol for MMLV

Figure 6B:
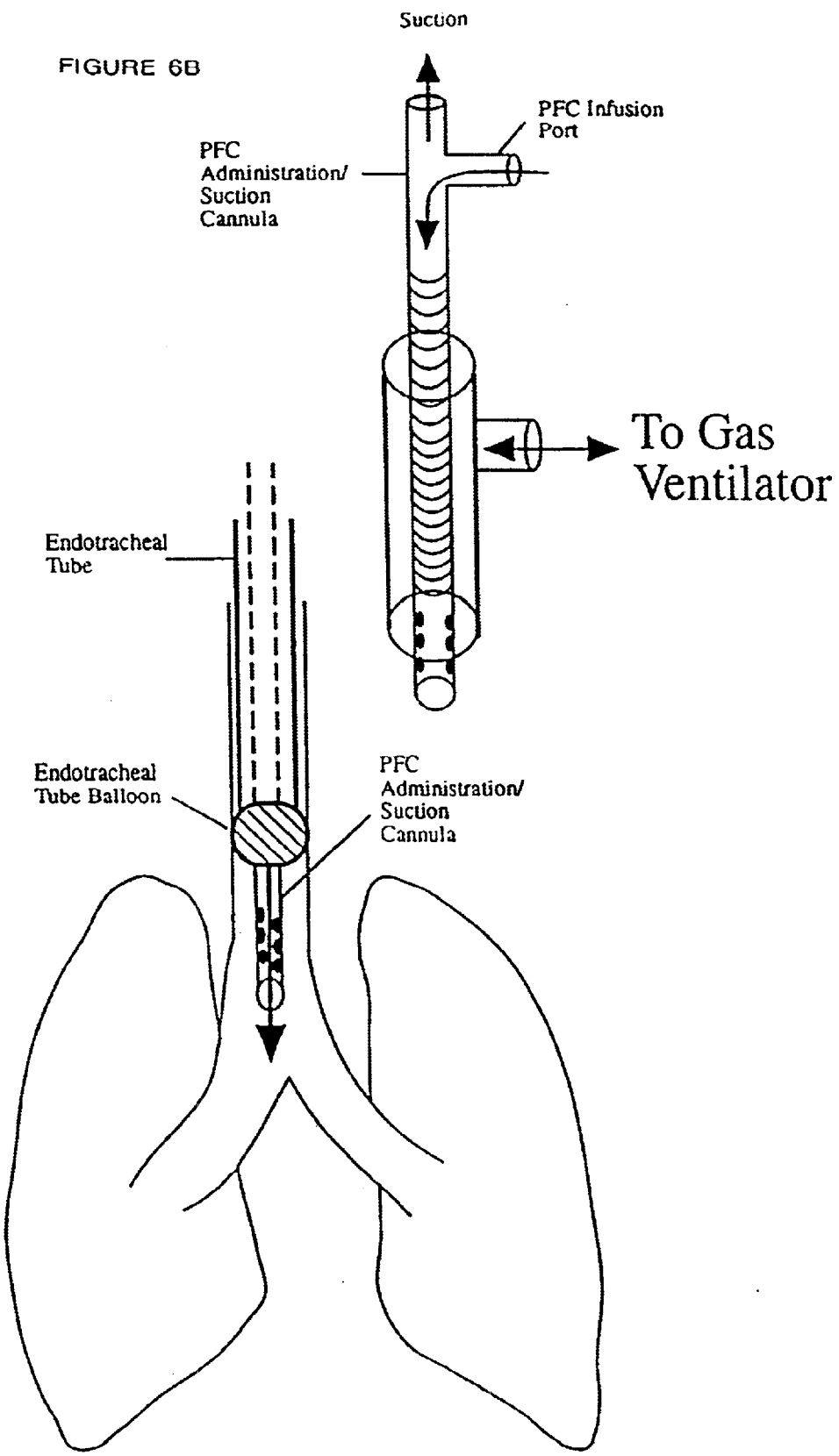
FIG. 6B is an illustration of how the device of FIG. 6A attaches to the lungs via the endotracheal tube.

In MMLV, the liquid loading sequence is typically achieved by pumping the PFC from a reservoir through a circuit consisting of a heat exchanger, a 20 micron-pre-filter followed by 0.2 micron absolute filter, and an oxygenator (FIG. 6A). For PFCs, the oxygenator, if used, must currently be a true membrane oxygenator, as the current generation of hollow fiber capillary oxygenators available in the U.S. are fenestrated at the micro-scale, and depend on the high H2O/gas surface tension to keep gas and liquid in the oxygenator separated, and do not work with the relatively low surface-tension PFCs. After passage through the oxygenator, the PFC liquid is then delivered to the subject through a tube which is passed through the suction port down the endotracheal tube, to the level of the carina (FIG. 6B). This single-lumen tube may be used to both deliver and suction liquid from the lungs. In the present implimentation, this tube is a specially constructed flat-wire-reinforced ultra-thin-wall tube with a fenestrated open-end, but many other designs are possible within the claimed type of device. Control of PFC infusion and removal may be done by a computer-controlled valve-driver and pressure-sensor device. Such a device, used for the series of illustrative examples herein, was designed by and built by Korr Biomedical Corporation, Salt Lake City, Utah, under direction of the patent claimants.

In MMLV, mechanical ventilation with gas proceeds in routine fashion with a pressure-limited or pressure-controlled mechanical gas volume-ventilator. This includes appropriate monitoring and control of peak inspiratory pressure, peak flow, tidal volume, minute volume, $FiO_2$ (inspired oxygen concentration), gas composition, and other relevant ventilatory parameters. The mechanical ventilator in the best implementation of the technique must -be able to sense and adjust these parameters appropriately as liquid is loaded and unloaded from the lungs. An additional relief valve must be included in the vacuum circuit also, in order to limit negative airway pressures which occur after liquid suction is completed during each cycle, and the suction circuit pump suddenly becomes exposed to airway gas.

The relationship between the volume of liquid in the lungs at any one time during mechanical gas ventilation, and the other variables of peak pressure, peak flow, tidal volume and ventilatory rate, is very important:

1) As a first approximation, peak positive airway pressure should not exceed 40 cm of water at the endotracheal tube external connector, and peak gas flow should decrease from a maximum of 60 L/min (LPM) to a minimum of 20 LPM or less, as the lungs are progressively loaded with PFC. Similarly, tidal volume of delivered gas will decrease to essentially zero whenever the lungs are loaded with PFC to 50–60% of TLC (ca. 50 mL/kg) and return to normal delivered tidal volumes of gas (i.e., 10 to 20 mL/kg/breath) when the lungs are unloaded of fluid to a volume approximately that of functional residual capacity (30 mL/kg). For mechanically-driven systems, rapid (4/minute) small infusions of fluid <10 mL/kg may be used to keep maximal airway pressures low.

2) The tidal volume of gas breaths will decrease to zero or near zero when the lungs are fully loaded with liquid, in order to avoid baro-trauma and volu-trauma. Generally, less than half, and as little as one-quarter, of total lung fluid load may be available for suction removal, before suction pressures become unacceptable due to loss of fluid return and exposure of the large airway gas to high negative pressures. In a fully flexible system, gas ventilatory frequency may also decrease during times of high lung liquid content, in order to minimize gas flow pressures. During liquid unloading, and for a pre-selected period afterward, gas ventilation rate and volume will increase in frequency as rapidly as the pre-selected limiting peak inspiratory pressure (or peak flow pressure) will allow, to a rate of 12 to 15 breaths per minute. This ventilatory rate has thus far been found to be effective for unloading of the lungs with PFC, via active suctioning. However, rates of up to 30 breaths/minute and more have been used, and in some circumstances are effective. High frequency ventilation may also be used. In this implementation, a catheter under the surface of PFC liquid collecting in the bronchi may be involved in liquid removal, and have little or no effect on gas ventilation given around the removal catheter, until the suction tip becomes exposed to gas.

The reason for observed gas-ventilation facilitation of liquid removal seems to be that gas ventilations cause liquid in small airways to be moved to large airways, where liquid can be removed by active suctioning at the bottom of a gravity drain. In a sense, MMLV allows PFC to be both pushed and pulled out of the lung, without chest compression. Briefly, PFC can be rapidly suctioned from the lungs when ventilator gas actively replaces it.

In TLV (prior art), the necessary ventilation frequency, which is in excess of 3 liquid breaths per minute, does not allow the bubble-free PFC fluid, with its limiting viscosity and flow, to become available for removal in this way, and consequently in TLV, tidal volumes and "minute liquid volumes" (dV/dt) must be severely limited at higher ventilatory rates. By contrast, in MMLV the much higher gas ventilation rate at which fluid removal rate limitations occur allows for considerably better $CO_2$ removal than occurs in total liquid ventilation. This is a novel feature of the invention.

Consideration of MMLV Circuit Mechanics

Following delivery of a PFC load to the lungs, the liquid must be removed and recycled through the heat exchanger/filter, and often oxygenator assembly. This assembly rids the liquid of $CO_2$, adds oxygen, removes mucus, bacteria and other airway debris, and appropriately heats or cools the fluid. Again, rapid but gentle removal of liquid from the lungs is best achieved by applying suction to the PFC delivery catheter (or alternatively the endotracheal tube) while imposing mechanical gas ventilation through a different concentric tube, per the algorithm described above.

External pressure (chest compressions) can also facilitate removal of PFC from the lungs, but under certain circumstances can also cause small tears or lacerations in heavier, liquid-loaded lungs. These tears are usually unimportant clinically unless they result in subsequent PFC in the pleural space ("perfluorothorax") in systems where the PFC used has a high vapor pressure (e.g., >40 mmHg at normal body temperature, e.g., 3M Company's "FC-84" mixture). This so-called "perfluorothorax," when it occurs, is clinically far less problematic with low vapor pressure (e.g., ~10 mmHg at body temp) PFCs, such as 3M Company's "FC-40" mixture, or the proprietary pharmaceutical perfluorooctylbromide, or perflubron (Liquivent™, Alliance Pharmaceuticals). Our invention of MMLV is suitable for use with all of these PFCs, and many others. However, for MMLV combined with manual or mechanical CPR, which greatly increases the risk of perfluorothorax, only low vapor pressures PFCs are suitable for use. Certain PFCs with undesirable low-temperature characteristics (eg, perflubron) such as high viscosity or freezing behavior near 0 C, cannot be used as cooling media in the most extreme cooling applications described herein. However, low liquid temperatures (near 0 C) per se do not seem to cause serious lung damage, and animals have survived 30 minutes of rapid cycling of PFC cooled to below 5 C, with core temperature drops of as much as −12 C. All animals allowed to survive the most rapid cold PFC cycling temperatures and rates described herein, returned to normal A-a gradients (a measure of, lung oxygenation function) within 48 hours after the procedure.

Appropriate ventilating gas composition is also very important for different clinical problems. In some situations, very high $FiO_2$ will be desirable, while in other situations some gas breaths may contain no oxygen for a short period. An example of the latter would be in cases of re-perfusion after cardiac arrest, where oxygen might be temporarily withheld for a few seconds in order to protect against exacerbation of re-perfusion injury by reintroduction of oxygen while free radical scavenging drugs are delivered to the tissues.

The addition of drugs to the ventilating gas to overcome vasoconstriction of the alveolar and other lung blood vessels and/or to correct V/Q (V/Q=dV/dt/dQ/dt) mismatch, is also a feature of this invention. In particular, the addition of nitric oxide (NO) to the ventilating gas, or to the PFC via the oxygenator, in concentrations ranging from 5 to 80 parts per million (or to effect) can overcome cold-induced vasoconstriction of the lung airways, and allow for improved rates of gas exchange.

The following are representative data from canine experiments done by the claimants and 21st Century Medicine (21CM), [Critical Care Research, Inc] which directly illustrate the performance as compared with other techniques which exist in the literature. Each experimental Example is a single exemplary animal, or a group of similarly treated animals, and will be used to illustrate one or more principles of the invention. They will also illustrate novel physiologic principles necessary to understand the mechanism of the invention. Although other materials and methods similar or equivalent to those described herein can be used in the practice or testing of the present invention, the preferred methods and materials are now described.

$21^{st}$ Century Medicine [now Critical Care Research] is an USDA licensed animal research facility. All animals used in the work described herein received humane care in compliance with the *Guide for the Care and Use of Laboratory Animals* published by the National Institutes of Health (NIH publication 85-23, revised 1996) and in accordance with all State and Federal laws regulating the use of animals in biomedical research. deliberate departure from SI nomenclature, heats are often given in this document in calories (1 cal=4.184 J) or kilocalories (1 kcal=4184 J). This is done because it greatly facilitates intuitive understanding of heat capacity relations in liquids and in watery solids, such as tissues.

Example 1 illustrates the rapid rate of heat transfer which typically occurs in Partial Liquid Ventilation (PLV) when a load of warm or cold fluid is infused as well as the three compartment heat reservoir model.

EXAMPLE 1

Analysis of Partial Liquid Ventilation

Illustrated in FIG. 1 is a canine model in which one load of non-isothermal PFC is given. In this experiment, one infusion of 1.65 L of cold, (4.4° C.) oxygenated PFC (here, the 3M Company PFC product "FC-84") is given rapidly (683 mL/min, over 145 seconds=31.3 mL/kg/min) by catheter passed below the lower tip of the endotracheal tube of a 21.8 kg dog. The volume infused (75.7 mL/kg) is chosen to be near 80% of the total lung capacity. Mechanical gas ventilation is continued through the entire procedure, resulting in very different thermal kinetics than in TLV (see discussion). For simplicity of interpretation, suctioning in this experiment is delayed until after a suitable dwell time (after complete temperature equilibrium had been reached).

Figure 1A:
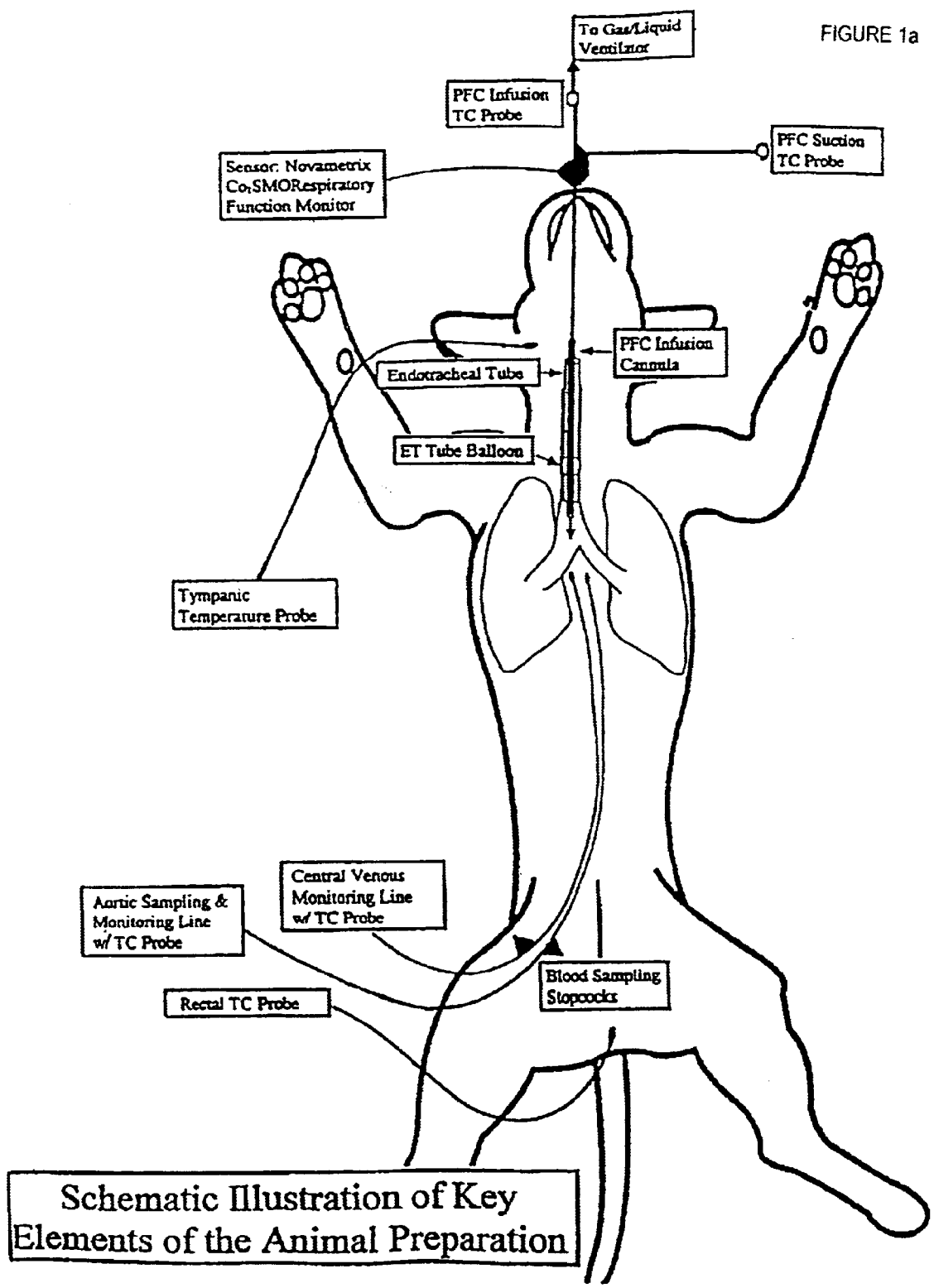
FIG. 1a shows a canine instrumented for measurement of temperatures as in Example 1. Indirect brain temperature is measured via a copper/Constantan thermocouple probe placed on the right tympanic membrane. Venous temperature was measured by a thermistor in a thermodilution catheter inserted via the femoral vein into the inferior vena cava. Arterial blood temperature was measured by a thermocouple probe inserted via the femoral artery into the descending aorta. Selected instrumentation modalities from Examples to follow are also illustrated.

FIG. 1 shows a graph of canine temperatures in experimental Example 1. The graph shows temperatures over time, as 75.7 mL/kg of PFC at 4.4° C. is loaded into the lungs over 145 seconds. Illustrated are animal esophageal temperature and indirect brain temperature as measured via a copper/Constantan thermocouple probe placed in the esophagus, and another on the right tympanic membrane. Also illustrated are venous and arterial blood temperature which were measured, respectively, by a thermistor in a thermodilution catheter inserted via the femoral vein into the inferior vena cava, and by a thermocouple probe inserted via femoral artery into the descending aorta. Instrumentation of the animal as described is illustrated in FIG. 1a.

The FIG. 1 temperature graph illustrates blood temperature (both venocaval and aortic) falling and then rising, as PFC is infused, then allowed to remain in the lungs. Esophageal temperature, which is a marker for the temperature of the relatively small amount of PFC in the trachea and large airways, does not come into equilibrium until about 450 seconds after infusion of cold PFC ceases, with a-half-time of about 120 seconds. Aortic blood temperature reaches a nadir at essentially the time infusion of cold PFC stops, then rises with a much faster half-time (about 80 seconds), with equilibrium complete at about 210 seconds after infusion ceases. Venous blood follows a similar pattern with a smaller deviation, with the venous temperature nadir offset from that of arterial blood by 30 seconds—roughly the mean blood circulation time of the animal.

The Three-compartment Heat Reservoir Model

In these experiments involving anesthetized and paralyzed dogs which do not shiver, the heat transfers are too rapid to show any effect from metabolism or surface cooling, and thus only temperature effects from the chilled PFC infused are seen. In Example 1, about ⅔rds of the brain/tympanic temperature change of the animal occurs during the "dwell-time" of the liquid (time between completion of liquid loading and liquid unloading). This indicates that heat is transferred between lungs and blood very rapidly on this time scale (i.e., this system of PFC, lung parenchyma, blood volume, and probably some heart/arterial intima and muscle, comprise a single thermal reservoir or compartment for purposes of analysis, at this time scale).

Figure 2:
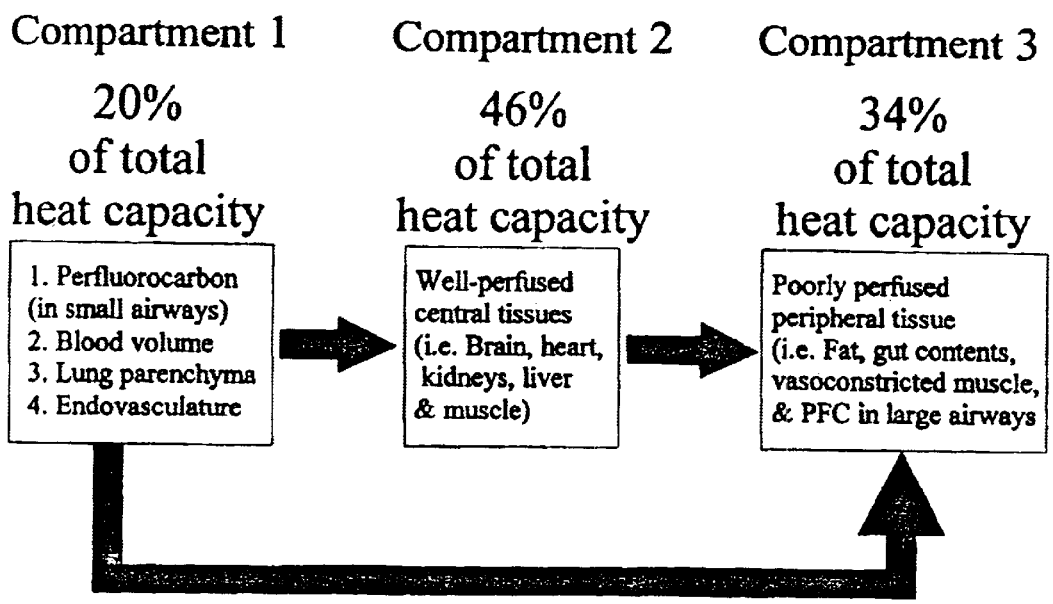
FIG. 2 illustrates the three major thermal kinetic compartments, and respective fractional heat capacities of such compartments, in an anesthetized canine with normal cardiac output, undergoing heat exchange through PFC lung lavage, as in Example #1. Existence and characteristics of such compartments may be inferred from measurements such as are graphed in FIG. 1, in studies such as Example #1, in the way that is hereafter detailed.

Heat is then transferred more slowly (i.e., slowly enough to easily see on this time scale), and in an approximately exponential fashion, from this first thermal compartment (PFC, lungs, blood volume, etc.), to the next 2 compartments, as illustrated in FIG. 2. Thermal equilibration with one of these compartments, comprising certain well-perfused tissues of the body, presumably the kidneys, heart, brain, liver and some muscle, is much more rapid, by a factor of about 6, than to the other compartment. These tissues therefore are taken to comprise one of two more thermal compartments (Compartments #2 and #3).

The fact that aortic blood temperature immediately (within lung-aorta circulation time of a few seconds) begins to rise after PFC infusion is stopped, indicates that even at these high loading rates of 31 mL/kg/min of PFC, there is no significant difference in the temperature of PFC residing in the small airways of the lungs, and the temperature of blood which has circulated through the lungs. (This fact is also indicated by the relative insensitivity of end-expiratory PFC temperatures to PFC loading and removal rates, in Examples to follow). A lag between the start of warming of aortic blood and the halting of cold PFC infusion, would indicate that a significant amount of infused PFC remained during this delay-time, which had not yet equilibrated with pulmonary circulation. Instead, at least up to the infusion rates of cold PFC tested here, a state of continuous near-thermal equilibrium between blood and most of the PFC in the lungs (excluding that PFC in large airways) is inferred. This is the rationale for including well-stirred small-airway PFC, and blood, in the same thermal compartment in this model "Compartment #1").

The final equilibrium change in body temperature of 1.6° C. suggests a total animal specific heat capacity of (75.7 mL/kg×0.45 cal/mL/° C.×31.2° C.)÷1.6° C.=0.66 kcal/kg/° C. This is a reasonable value. Values for lean tissue and blood are respectively 0.87 and 0.88 kcal/kg/° C. (Cooper and Trezeh, 1971), and a lower mean value for whole animals reflects the lower water content and specific heats of bone and fat.

Compartment One to Compartment Two Heat Transfer

The nadir of aortic blood temperature (occurring at the end of the PFC load) in this experiment is 5.5° C. below body temperature, and the temperature for venous blood at this time is 2.6° C. below initial body temperature. Tympanic temperature at this time has fallen 0.5° C. From these figures it is possible to make some simple quantitative estimates of heat transfer dynamics between heat compartments in this model, without the use of complex mathematics or computer modeling.

The 75.7 mL/kg of PFC given in this experiment represents a heat deficit of (37° C.−4.4° C.)×0.45 cal/mL/° C.×75.7 mL/kg=1110 cal/kg. Of this heat, at the time of the end of the PFC load, the arterial blood (assumed on the basis of average land mammalian body composition to be about 20 mL/kg) holds approximately 0.88 cal/mL/° C.×20 mL/kg×5.5° C.=~100 cal/kg heat deficit, and the venous blood, 40 mL/kg (by similar calculation) holds about the same. The remaining PFC in the lungs, which can be assumed to be mostly at the same temperature as the arterial blood (see argument above and experimental data below) still has a heat deficit of 75.7 mL/kg×0.45° C.×5.5° C.=~190 cal/kg. In ~150 seconds, the PFC load has transferred (1100−190)/1100=~83% of its heat deficit to Compartments #1 and 2.

At this time, body temperature has dropped by 0.5/1.8= 35.7% of its final amount, indicating that ~1100 cal/kg×(1− 28%)=~750 cal, is still to be accounted for at this point. As calculated, 390 of these "deficit calories" are in blood and PFC. The remaining ~360 cal/kg heat deficit must therefore at this point be distributed in internal viscera very well equilibrated with blood, probably primarily in lung parenchymal tissue and vascular tissue (including some of the endocardium). The mass of this immediate visceral heat sink, which is at arterial/PFC temperature of −5.5° C. below body temperature, and assumed to have a typical specific heat capacity of organs and lean tissue of 0.87 cal/kg/° C., can be estimated to have a mass of 360 cal/kg÷5.5° C.÷0.87 cal/g/° C.=75 g/kg, or 7.5% of body mass. This non-blood "rapid heat equilibrium" visceral mass is thus about the same mass as the blood volume (also usually 7–8% of body mass), and in a 21.8 kg dog would amount to 1.6 kg of tissue. Thus, the "rapid equilibrium compartment" or first thermal compartment of a dog receiving cold PFC lung lavage, is found to consist of about 50% of contribution from less than 2 kg of certain internal viscera (probably mostly lung, with some heart and vessel contribution), and 50% from infused PFC, plus total blood volume. This compartment, since it has twice the heat capacity of the visceral contribution just calculated, would comprise (2×0.075×0.87)/0.66=20% of the heat capacity of the animal, and a bit less than the same fraction of the animal's mass.

Third Compartment Equilibration (Core to Peripheral Tissue Heat Transfer)

An initial 1.8° C. brain/tympanic drop in one-load cooling (implying mean specific heat capacity of only 0.59 kcal/kg/° C.), is unreasonably high for a non-obese, young animal, and must reflect cooling of only part of the animal (i.e., the first two thermal compartments discussed above, plus only a fraction of Compartment #3) in such experiments. Final equilibration of the first two thermal compartments with the third takes place after blood and tympanic temperatures equilibrate (Compartment #1 and 2 equilibration) after about 4 minutes from the end of the PFC load (calculated half-time is 1.3 minutes). Tympanic cooling reaches a nadir of −1.8° C. below the starting body core temperature at this time, reflecting Compartment #1 and #2 equilibration, then slowly rises toward a point −1.6° C. below initial temperature, over an additional 10 minutes (calculated half-time is ~6 minutes).

The delayed rise in body temperature after central cooling (which may be thought of as "after-rise" by analogy to "after-drop" during peripheral re-warming) indicates thermal equilibrium of compartments #1 and #2 is being reached with the third thermal compartment, which is not as well perfused as the brain and central body organs. This third compartment is assumed to represent fatty tissue and some cold-vasoconstricted muscle and skin, and is sometimes referred to in the literature as the "peripheral tissues" (vs. the better-perfused "core tissues."). The third (or peripheral) compartment may also be expanded to include PFC in large airways (see the esophageal temperature curve in FIG. 1) which also warms with a similar, though slightly faster, half-time.

Estimation of the comparative size of the third thermal compartment (periphera 1 tissues) in the dog can be made from the "after-rise" in body temperature which occurs from the time the first two thermal compartments ("core tissues") reach equilibrium (about 7–10 minutes into the experiment), and the time the final "equilibrium" body temperature is reached at ~16 minutes. During this time the increase in body temperature from $1.8°$ C. to $1.6°$ C. below the initial temperature indicates that the heat capacity has increased by a fraction $1.8/1.6=1.12=12\%$. This increase is due to residual heat capacity of the third compartment being made available, even though because of its own cooling half-time, the fraction of its heat capacity left will by this time (7–10 minutes) be only about $\frac{1}{3}^{rd}$ of its original, since this time represents about 1.5 half-times for this process, meaning the $3^{rd}$ compartment is about 65% of the way to equilibrium with the lungs by the time it begins serving as the sole warm reservoir for rest of the body.

The 12% increase therefore represents about $12/.(1-0.65)=34\%$ of the initial heat capacity of the animal, as a crude and approximate estimate. This leaves the remaining 46% for compartment #2 (see FIG. 2). Note that ¼ of the 20% heat capacity in Compartment #1 is PFC, and for smaller loads on top of FRC PFC content, this number will tend to be closer to 17%.

Figure 5:
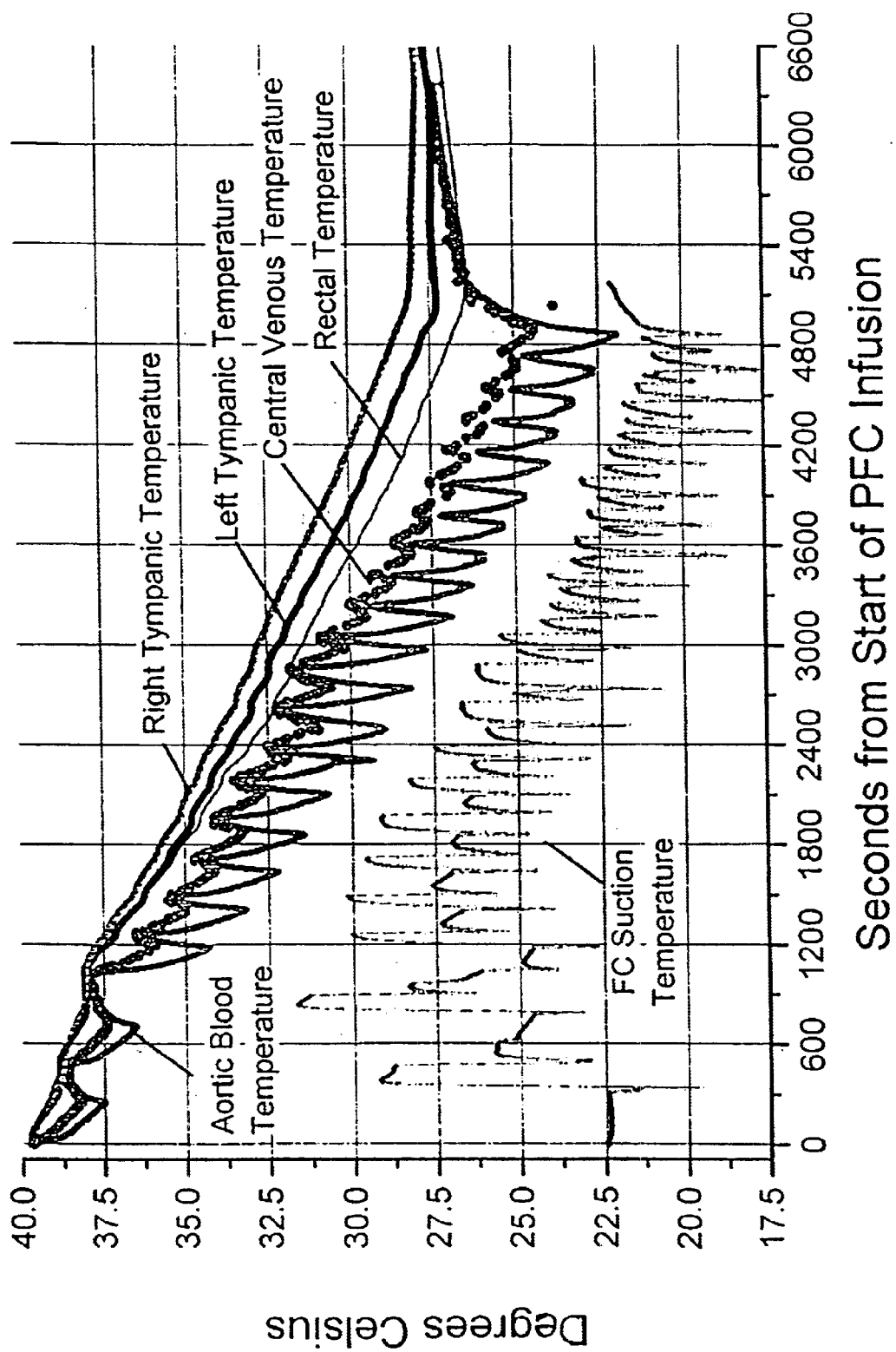
Figure 8:
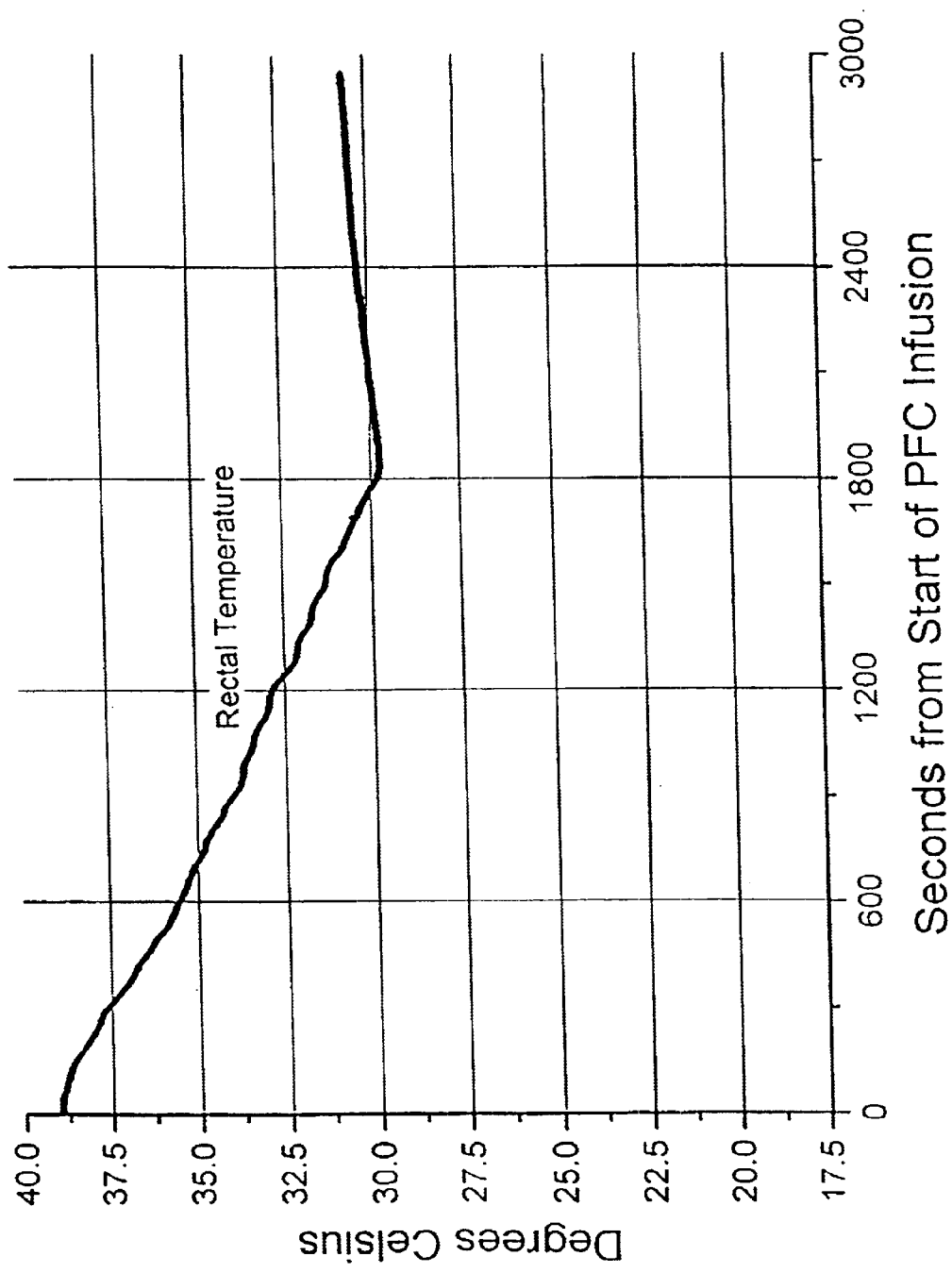
Figure 9:
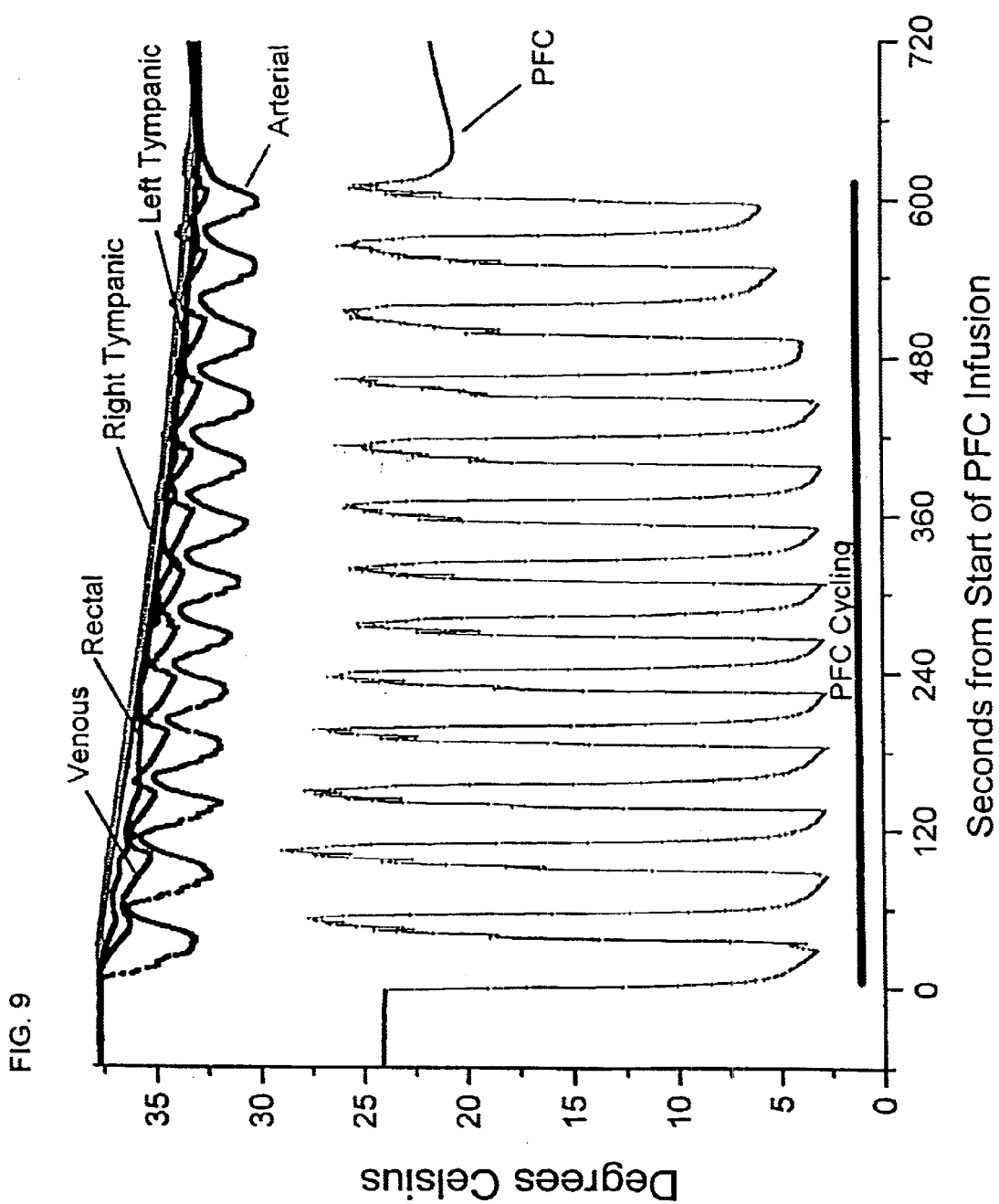
Figure 9A:
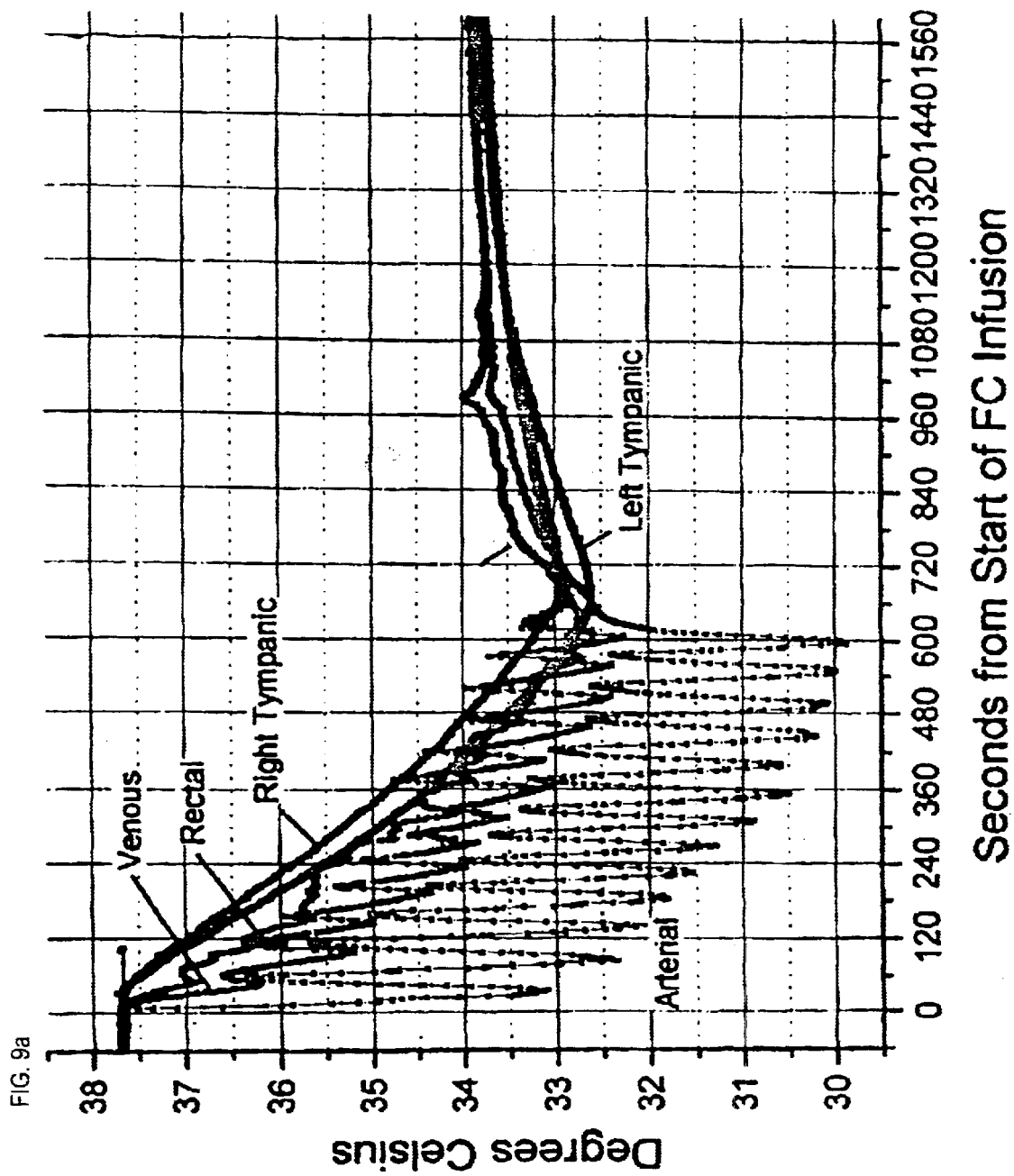
FIG. 9a shows the same experiment, but with temperatures graphed without PFC temperatures, for ease of interpretation.
Figure 10:
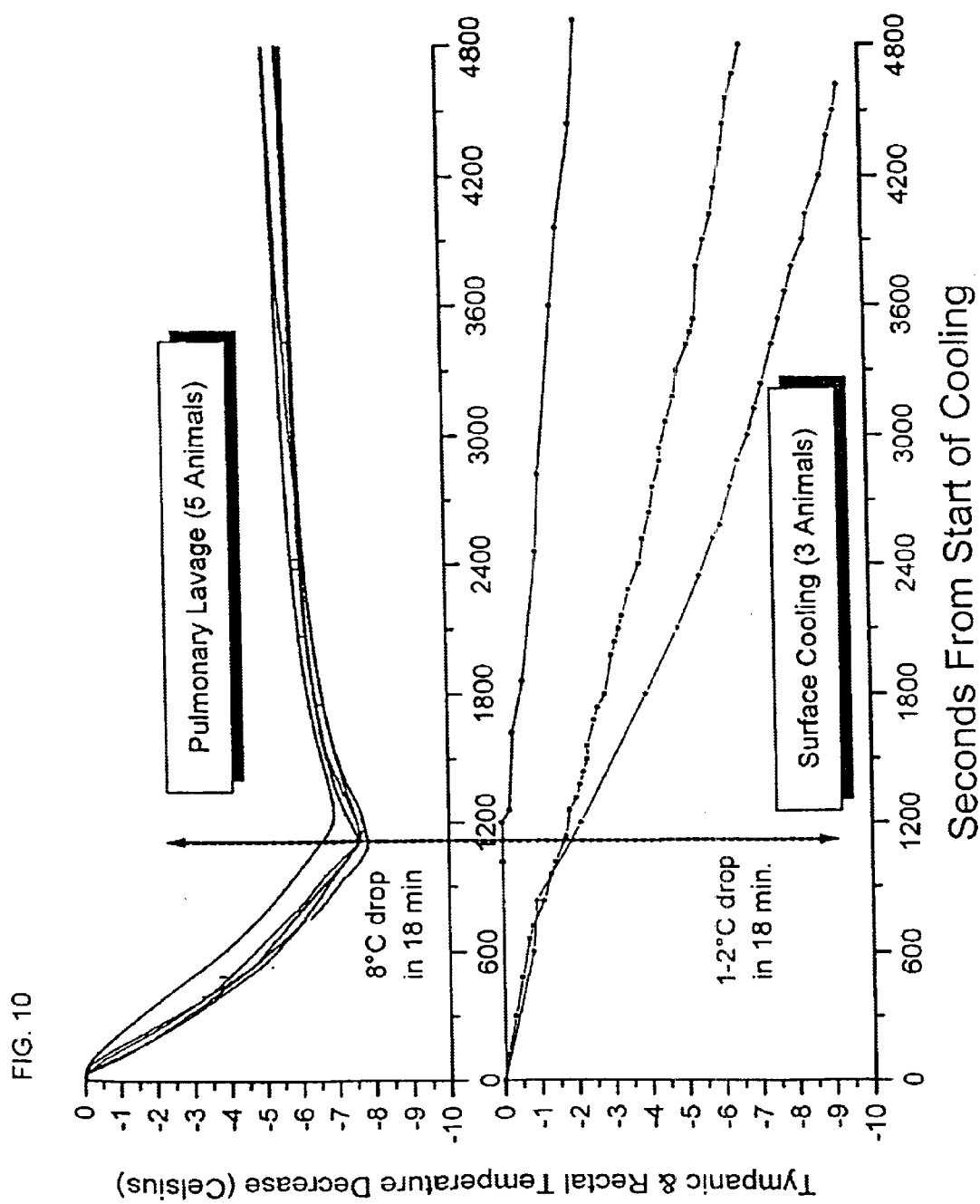
FIG. 10 Shows typmanic temperatures of 5 anmals cooled by rapid lavage with PFC by MMLV techniques, vs Surface cooling.
Figure 10A:
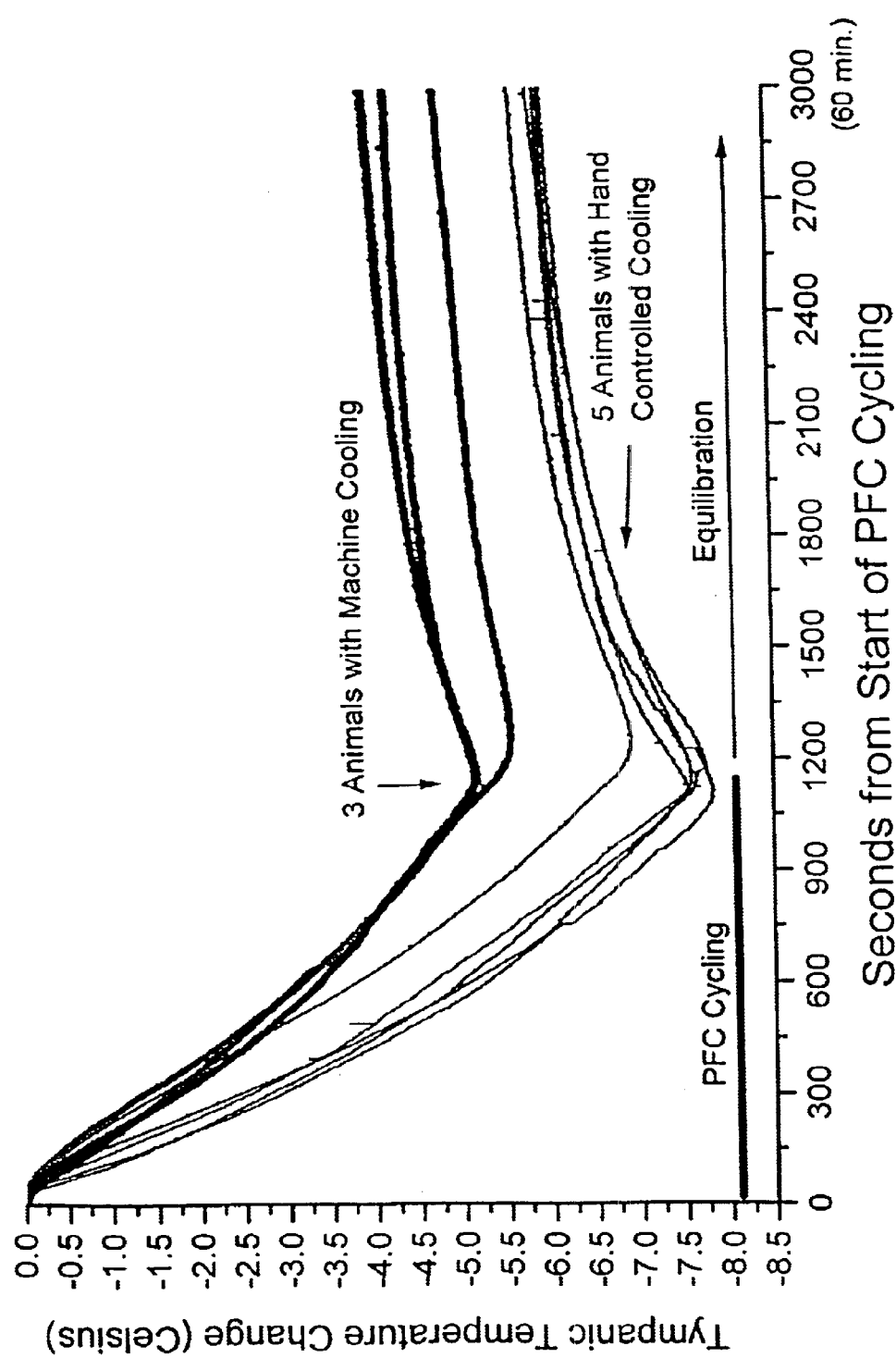
FIG. 10a shows tympanic temperatures of 5 animals cooled by rapid lavage (same group as above) vs cooling of dogs by machine cooling at 50% of the lavage load, but twice the lavage rate.

See also FIGS. 8, 9 and 10 for examples of this phenomenon of "after-rise." In summary, we find that this animal can be modeled as three thermal compartments, with heat or cold transferred from the first to the second rapidly (with a half-time of about 1.3 minutes) and then from both of these compartments to the third compartment at a slower rate. Half-time for this process is ~6 minutes in this illustration and also in Example 6, FIG. 9. It is ~6.5 minutes at the end of PFC infusion in Example 3, FIG. 5, illustrating equilibration with a colder animal. Note that in the literature, equilibration between core and peripheral compartments is quite dependent on absolute temperature, since it is greatly influenced by cold induced vasoconstriction and drop in total cardiac output. Because of low blood flow with severe vasoconstriction, movement of heat between core and periphery in deep hypothermia is slow enough to be mediated partly by direct thermal conduction through solid tissues, in addition to blood circulatory heat transport.

Estimate of the Quantitative Rate of Heat Transfer

In the above experiment (Example 1), the rate of heat transfer from Compartment #1 to Compartment #2 and #3 can be estimated by noting that the maximum rate of temperature increase in aortic (arterial) blood temperature is $1°$ C. in 0.5 minutes (2 C/min), suggesting a maximum heat removal rate for the arterial blood lung PFC, and most of Compartment #1, which are presumably at about this temperature also. If 15% of the heat capacity of the animal is in non-venous blood in compartment #1, then rate of heat transfer represented by 2 C/min is $2°$ C./min×0.15%×21.8 kg÷(0.64 kcal/kg)=5.1 kcal/min=356 watts. If the heat transfer by blood at this time is crudely estimated by the Fick principle (using thermodilution) from the estimated cardiac output (about 2.5 L/min for an animal this size) and temperature difference between venous and arterial blood ($3°$ C.), the maximal blood heat transfer power at this time is: 2.5 L/min×0.88 kcal/$°$ C./L×$3.0°$ C.=6.6 kcal/min=460 watts. These numbers suggest that blood heat transport alone is more than enough to account for heat transfer from Compartment #1 to Compartments #2 and #3 in this Example. Indeed, in later Examples (see FIG ) we find that the fastest PFC rates employed (infusion plus suction (30 mL/k/min) typically give PFC delta T's of 17 C, for calculated cooling powers of about 4.8 kcal/min=336 watts. These typically cool 20 kg dogs at an average net rate of 0.33 C/min, implying (assuming heat capacities of 0.7 kcal/kg), cooling powers of 20×0.7×0.33./88=4.6 kcal/min=322 watts. Arterial/venous temperature differences of 1 C going to 1.5 degrees over the cooling run are common (see FIG ) and imply cardiac outputs by thermodilution of 4 liters per minute, dropping to 3 L/min. Again, blood transport of heat seems entirely adequate to explain most features of heat transfer from lungs to body in this model.

Conclusions

There are several conclusions to be drawn from this example (Example 1), which are important:
1) If gas breaths are used, PFC reaches very rapid thermal equilibrium with blood, even at PFC infusion rates greater than 30 mL/kg/min.
2) If gas breaths are used, heat or "cold" from an infused PFC load is rapidly transferred to a larger mass of lung, vascular tissue, and blood, which acts as a short term storage "heat capacitor" which has an effective heat capacity 3–4 times that of a 60 mL/kg (⅔rds total lung capacity) load of PFC. This, combined with some heat transfer from blood to the peripheral tissues during even the fastest PFC lung loading, guarantees that at least 75% of heat or "cold" will be extracted from a significant fraction of a lung load of PFC at infusion rates of ~30 mL/kg/min, even with no deliberate "dwell time." For example, as seen in FIG. 1, this equilibrium is fast enough that when loading (to *.80% total lung capacity volume) with PFC is accomplished in 2.4 minutes, less than ⅕th of the total heat absorbing capacity of the PFC remains at the end of infusion.
3) Equilibrium cooling or warming of PFC in large airways (effective thermal "dead space") proceeds slowly, and the amount of heat-sink in this fluid is of interest, because it is lost during rapid ventilation. However, since it would take very slow ventilation (or infusion/suction) to equilibrate this fluid, an efficient protocol ignores it, and uses no dwell time. With gas ventilation augmenting mixing, the thermal load in PFC in smaller airways is very rapidly removed, and this (faster) transfer is too rapid to be limiting to heat transfer in the present model.

The slow esophageal re-warming in the previous experiment illustrates the relatively slower thermal equilibrium of chilled PFC in large airways, even though the gas for mixing and warming PFC in smaller airways, is blown through the cold PFC in larger airways. This PFC remains cold because it is only slightly affected by the small heat capacity of gas blown through it, and because it is physically too far from blood and other tissues to be warmed at the same rate as PFC in the lung periphery.

Experimental Example 2 (FIGS. 3, 4) illustrates heat transfer in a model with multiple cycles of PFC loading and unloading. In each cycle, cold PFC is loaded from FRC (functional residual capacity) to about twice this volume, accompanied by constant gas rate ventilation. This protocol does not represent Total Liquid Ventilation (TLV), because ventilation and $CO_2$ removal are accomplished mostly by gas breaths from a conventional gas ventilator (here at a constant rate of 12 breaths/min). However, gross heat transfer in this experiment is accomplished by unloading the PFC liquid soon (or immediately) after loading, and then repeating the procedure with multiple cycles of freshly chilled liquid. This is similar to a multiple lavage procedure with ice water in the stomach or peritoneum, but has not been described as a technique for PFC infused with air into the lungs or other body compartments, and is novel when used as such. Moreover, the use of gas ventilation mixing specifically and deliberately to assist with transfer of heat from PFC liquids to the lungs/blood, is novel.

The principles above may be used to design a maximally efficient protocol for cooling a subject with MMLV. Example 2 illustrates one possible protocol.

EXAMPLE 2

Illustration of Mixed-Mode Liquid Ventilation (MMLV)

Figure 3:
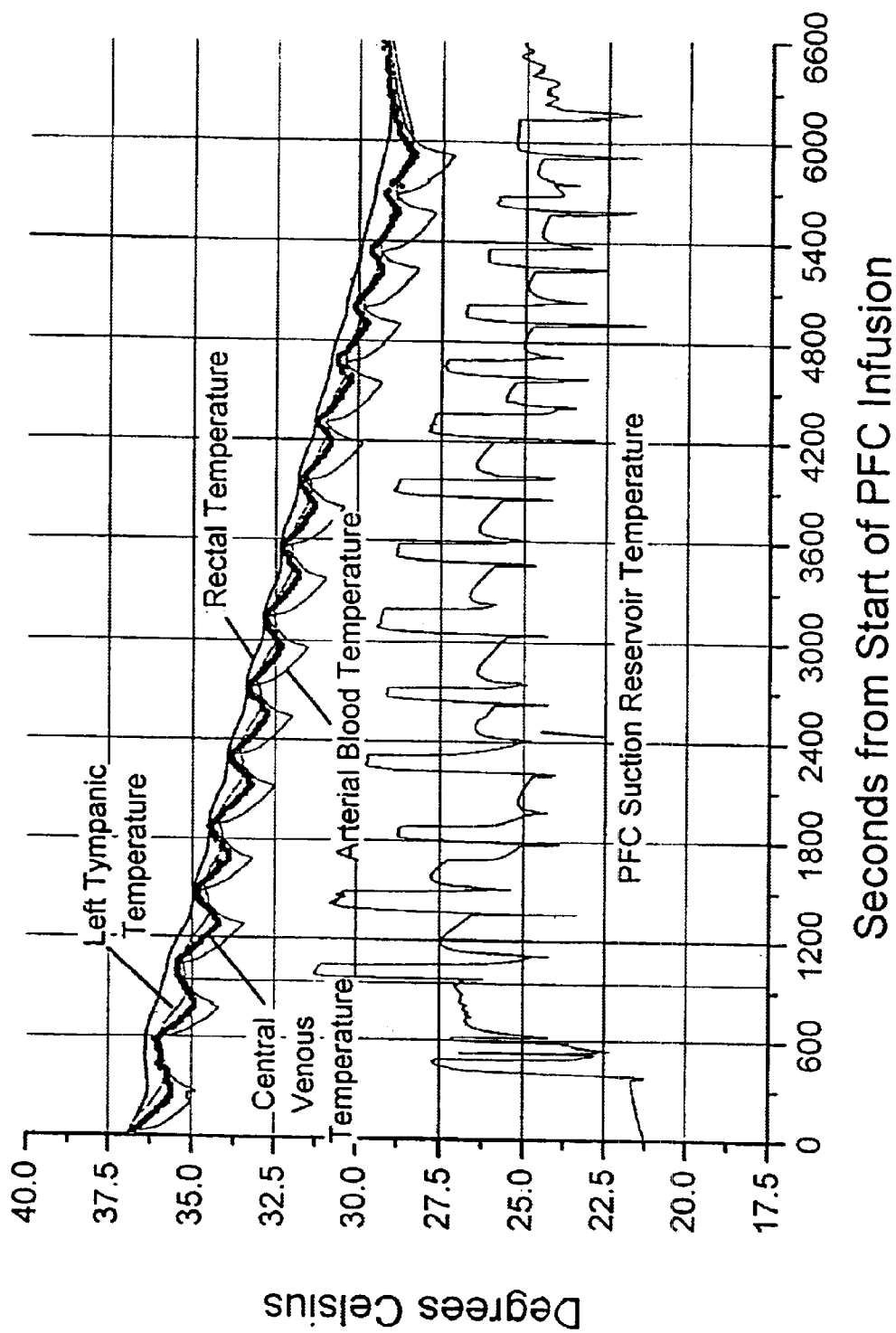

Illustration of the Concept:

In the following illustration (Example 2), a 25.7 kg anesthetized, intubated, and paralyzed dog was given chilled PFC (temperature −1° C.) rapidly into the endotracheal tube, followed by removal by vacuum suctioning. FIG. 3 shows tympanic, rectal, venous, and aortic blood temperatures as a function of time. Also illustrated on the same scale are temperatures of the removed PFC with each cycle, measured in the suction reservoir (which is emptied after each cycle).

This experiment illustrates use of multiple loads of chilled fluorocarbon liquid from FRC to 2×FRC, with varying dwell times after each liquid PFC load (here again the PFC is 3M Company's product "FC-75"). In this illustration, the rate of PFC liquid loading is 155 mL/min, or 6.0 mL/kg/min, to a total of 24 mL/kg for each 4 minute load, followed by suctioning over 2 minutes to remove fluid at a rate averaging approximately 12 mL/kg/min. The relatively smooth cooling temperature curves are for the entire animal (tympanic and rectal temperatures), whereas the larger, periodic temperature fluctuations (total of 15) are blood temperature swings (as measured with thermocouples in the aorta and inferior vena cava). Each temperature fluctuation represents a cold PFC load, and subsequent removal by endotracheal suctioning.

At 6 mL/kg/min average infusion rate, rather than 31.3 mL/kg/min, initial loading in this experiment was done much more slowly than in Experimental Example 1. After the first two loads to approximately 60 mL/kg (approximately 2/3 FRC), an additional dwell time (in which PFC is neither infused or removed) of 6 and 4 minutes respectively was allowed for blood temperature to equilibrate with tympanic temperature. During these times, blood temperatures changed by 4 to 5 times the rate of tympanic temperatures, indicating that by this time (17 minutes into cooling) the heat capacity of the compartment in rapid thermal equilibrium with the blood (i.e., lung tissue and peripheral PFC in the lungs) was again relatively small (on the order of 20%), compared with the heat capacity of the well-perfused, or core thermal compartment. At this time (17 min, at equilibrium after $2^{nd}$ loading cycle), tympanic temperatures had dropped by only 1.5° C. (0.09° C./min, or approximately 5° C./hr). In the following 13 cycles (15 cycles total), loading and unloading with infusions of 24 mL/kg was continued (both at previous rates and volumes, thus making 4 minute infusions), but dwell time was cut to 60 seconds, then 30 seconds, and finally to zero for the last 4 cycles. The effect of this change in dwell .time on core cooling is to smooth out changes in temperature, but not markedly change the temperature of removed PFC or change the rate of cooling, as shown in FIG. 3.

FIG. 3 shows that average temperature of extracted PFC is about 3° C. below venous temperature (venous temperature is assumed to be Compartment #1 temperature). Thus, heat exchange within compartment 1 is seen to be substantially complete. Heat exchange is not complete between compartment 1 and 2 (venous blood and soft tissues) when liquid begins to be removed in this model, and this is a typical feature of heat removal with more rapid rates in MMLV.

Heat Transfer Measurement and Calculation of Heat Capacity

The amount of heat removed from the animal by the PFC may be easily assessed by measuring the temperature of the PFC infused, and the temperature of the mixed load of removed PFC. In this example, mixing (30 seconds of mechanical stirring) was performed on the volume of suctioned PFC to alleviate temperature gradients in PFC as it is removed. Mixing allows for mass-averaged temperature and heat content to be assessed.

FIG. 4 (table of suction volumes and heat contents) shows temperatures of PFC inspired and removed in this example, their temperatures, and the heat removed with each load of PFC infused and removed. Because some PFC remains in the animal at the end of the experiment, and because suction volumes do not always match infusion volumes, heats can be calculated in two ways. In the first method, heat infused and removed is calculated for all volumes of PFC, and then a correction is. added for the volume difference between infused and removed PFC. This residual PFC is assumed to remain in the animal and to equilibrate with the animal's final body temperature. When this is done, total heat removed is found to be 125.9 kcal+10.9 kcal=136.8 kcal. Alternately, heat can be estimated by the difference in mean infusion and suction line temperatures during the middle of infusion and suction, and using infusion volumes only (on the assumption that suction volumes will be similar over the long run). This method, which does not rely on measuring suction volumes, is the only one which lends itself to heat measuring during rapid unloading experiments, in which suction volumes cannot be easily measured, but in which infusion volumes are easily estimated from infusion rates. Such a calculation for Example 2 yields an estimated heat removal of 130.8 kcal, in good agreement with the more difficult method. Specific heat capacity for this animal is then estimated to be 136.8 kcal/25.7 kg/7.5° C.=0.71 kcal/kg/° C. This is a reasonable number, and suggests that the method has no serious unaccounted-for heat losses at these low infusion rates.

Example 3, shows the results when infusion and suction rates are increased.

EXAMPLE 3

Effect of More Rapid PFC Cycling

This experiment is similar to the one previously described, but with an animal weight of 24.5 kg and infusion rates up to 410 mL/min=16.7 mL/kg/min, and increased suction rates.

In this experiment, the first two cycles were each loaded with 25 mL/kg PFC over 4 minutes (6 mL/kg/min), then allowed a dwell time of 1.5 minutes. To assess the effect of shorter cycle times and more rapid PFC turnaround, no dwell times were used in subsequent cycles, and infusions were shortened in cycles 3, 4, and 5, to 2.5 minutes (34 mL/kg load at a rate of 13.6 mL/kg/min) with 1 minute suction times. Finally, infusions were shortened to 2-minute loads at the fastest infusion rate of 16 mL/kg/min, for loads of 33.4 mL/kg. The effect on heat transfer is obvious from the increased rate in body temperature fall during cycles with faster infusion and zero dwell time. Rectal temperature fell a rate of 1.5° C./14 min=0.107° C./min=6.4° C./hr over the first two cycles. Subsequently, more than doubling infusion rate and eliminating dwell time increased effective infusion+removal rate to 16.7 mL/kg/min×2/3=11.1 mL/kg/min, and an increased rectal temperature drop rate to 0.15° C./min=9.0° C./hr.

At this liquid infusion rate (maximum 16 mL/kg/min= average of 11.1 mL/kg/min infused and removed), there is not enough time for blood temperatures to reach equilibrium with tympanic (brain) temperatures before liquid begins to be withdrawn, since half-time for this process is again 40 to 60 seconds. At the end of the experiment, this is seen in a steady divergence of venous blood and solid tissue temperatures. However, this heat transfer half-time provides more than enough time to transfer most of the heat out of the fraction of PFC in each infusion which reaches the lung periphery, as seen by the continuing small temperature gap between expired PFC and venous blood temperature. This gap is thought to represent mostly PFC in large airways, as discussed above.

Calculation of total heat removed in this experiment was made by summing the differences in suction and infusion temperature for each cycle, and multiplying by PFC specific heat capacity and the infused volume. The total heat removed was 218.2 kcal or 8.9 kcal/kg. This, with a total temperature drop of 11.7° C., implied a specific heat capacity of 8.9/11.7=0.16 kcal/kg/° C. Again, heat is accounted for.

In this example, total PFC volume infused and recycled was 16,469 mL over 85 min, for an average cycle rate of 7.9 mL/kg/min. In order to obtain faster temperature descents of 20° C./hr, the goal in this series, loading and unloading rates of 2.5 times this rate would in theory be required. Unloading at these rates would need to be facilitated by ventilations during unloading, according to a gas ventilation algorithm, such as that previously discussed.

Accordingly, the next experiment to be illustrated involves full Mixed-Mode Liquid Ventilation, using a gas and liquid infusion algorithm.

Example 4 is a similar experiment using a 17.3 kg dog and different infusion rates.

EXAMPLE 4

Full Mixed-Mode Liquid Ventilation With Very Rapid PFC Loading and Variation in Ventilatory Rate During Unloading This experiment (FIG. 6) using a 17.3 kg dog illustrates the result when infusion rates are increased by a factor of 2.6, from 16.7 to 44 mL/kg/min. At these rates, PFC liquid loading to 1.5×FRC is accomplished in approximately 60 seconds (to 44 mL/kg) for the first load, and 30–40 seconds per load, once an equilibrium. distribution of PFC in the lungs has been reached (beginning at cycle 4). This results in average infusion volumes of about 30 mL/kg, on top of FRC. Infusions were cut off when pressures reached 40 cm $H_2O$=29 mmHg.

These natural infusion and removal volumes at equilibrium cycling (30 mL/kg) are typical in MMLV experiments, though smaller infusion volumes (<20 mL/kg) have recently been found to provide much better control of peak large airway pressures. In order to remove liquid at rates comparable to infusion, it is necessary to use a high flow femoral cardiac bypass venous return canula (such as the 19 French diameter flat-wire Biomedicus venous return canula used in this experiment) to remove PFC with vacuum suction. In addition, it was necessary to control ventilation rates and pressures continuously during loading and unloading, both in order to avoid exceeding peak permitted airway pressures (40 cm of H2O) at the end of loading cycles, and also in order to facilitate liquid removal during unloading, as described in Section I. The result, in which gas ventilation and liquid ventilation proceed independently, constitutes the novel invention claimed (Mixed-Mode Liquid Ventilation, MMLV).

Figure 7:
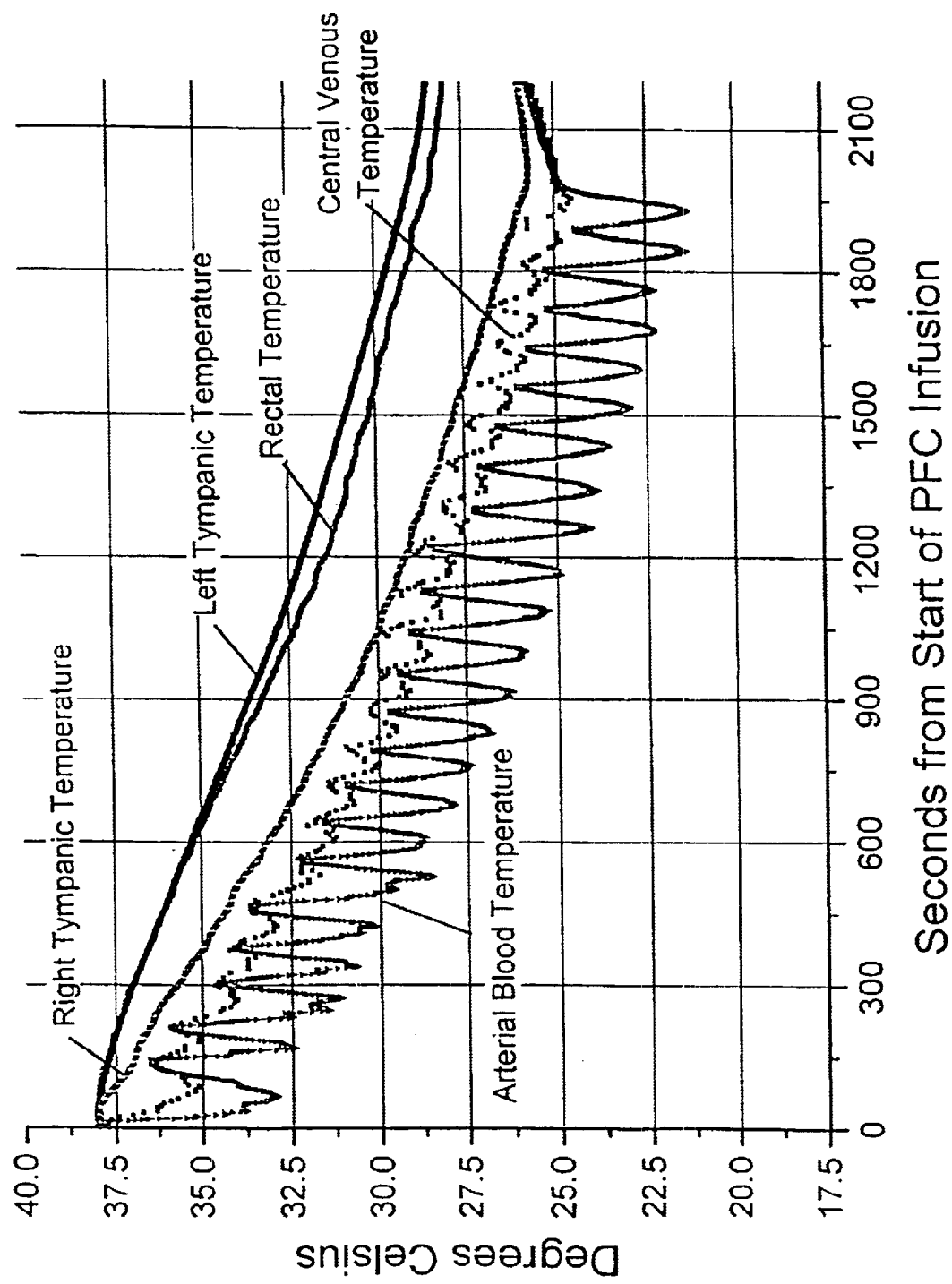

With MMLV, PFC removal rates in Example 4 averaged 1390 mL/min early in the experiment, and fell to 900 mL/min by the end of the experiment for the same volumes suctioned. These effects were attributed to increasing viscosity of the fluid, and/or differences in airway dynamics making less fluid available at lower body temperatures. The average time in which a 578 mL load of PFC could be both loaded and removed in this experiment, was 70 seconds at the beginning of the experiment, and 80 seconds at the end of the experiment. This resulted in an average PFC cycling rate of 578 mL/75 sec=7.7 mL/sec or 462 mL/min. For this 17.3 kg animal, maximum cycle PFC rate was thus 462 mL/min÷17.3 kg=26.7 mL/kg/min. This is 2.4 times the maximum infusion cycle rate (11.1 mL/kg/min) of Example 1. However, this did not reach the expected cooling rate of 21.6° C./hr (2.4×9° C./hr), primarily because the PFC was infused at a higher temperature in this experiment (3° C. to 4° C.). The actual cooling rate in this experiment, as seen in FIG. 7, was 17.6° C./hr (rectal) and 22.6° C./hr right tympanic (tympanic temperatures are reflective of brain cooling). In this example, rectal temperature was decreased 9° C. in 31 minutes. Tympanic and rectal temperature descent rates differed slightly due to non-equilibrium between the 2nd and 3rd heat compartments in the animal, as discussed above.

Estimation of heat removed in Example 4 was performed as in Example 5. Total heat removed was estimated to be 123.4 kcal, with a body temperature change of 9.5° C. Specific heat capacity was then 123.4 kcal/17.3 kg/9.5° C.=0.75 kcal/kg/° C.

EXAMPLE 5

Scale-up of MMLV

In a larger animal (30 kg) subjected to MMLV using the same technique, but scaling up liquid infusion flows, approximately the same cooling rate (20° C./min) was achieved by MMLV (FIG. 8). For this scale-up, liquid infusion was increased slightly more than linearly with animal mass (to 46 mL/kg/min), to make up for non-linear effects in PFC removal. However, at this rate we found that pressure-limited PFC volume loads were slightly less than in the smaller animal (Example 2) and averaged 740 mL (24 mL/kg) in the experiment, with good regulation of maximum peak pressure. It was found later in this experiment that when pressure constraints were relaxed and peak pressures were allowed to increase to 50–60 cm $H_2O$, 1360 mLs could be loaded (45 mL/kg). Suction rates in this experiment averaged only 840 to 900 mL/min (data not shown), mainly due to a poorer algorithm for managing ventilation. These results illustrate the sensitivity of MMLV to ventilatory algorithms and airway pressures (this animal suffered lung baro-trauma, but survived). PFC cycle time rate for this animal was only 11 mL/sec or 663 mL/min. For a 30 kg animal this calculates to 22 mL/kg/min. The cooling rate actually achieved of 20.3° C./hr tympanic, and 18.5° C./hr rectal, was similar to Example 4 (17.4 kg animal), despite only 83% of the PFC recycle rate/kg. This was partly due to a smaller lean body mass fraction in the 30 kg animal, with a reduction in specific heat capacity. Specific heat capacity for this animal was calculated, as above, at 0.70 kcal/kg/° C.

In MMLV, infusion rates generally will need to be increased at a more than linear rate per animal mass. This is because average PFC fluid removal rates do not scale well with animal size, due to a maximum removal rate set by the removal catheter and suction system. Larger animals are expected to show slightly faster gross PFC removal rates due to longer times in which pure PFC, rather than a mixture of PFC and gas, is available for removal during suctioning. However, these effects may be partly offset by better system design. For example, in the 17.3 kg animal infused at 45 mL/kg/sec, removal times were 55% to 78% of infusion time. For a 30 kg animal with comparable infusion rates and the same system, total liquid removal time had increased to 145% of infusion time. However, in Example 6, FIG. 9, a 19.8 kg animal infused at 46 mL/kg/min, improvements in the suction system allowed removal rates of 80 mL/kg/min (~1600 mL/min), and suction times had decreased again to less than 70% of infusion times.

Similar increases in the ratio of infusion to removal are expected for even larger animals, and in humans. Some of these effects are expected to be ameliorated by the use of larger diameter suction canulae in humans, and by improvements in the liquid circuit which minimize flow resistance. For a 70 kg human, even if no improvements over the presently demonstrated system are realized, an infusion rate of 50 mL/kg/min (easily achievable), and a removal rate of 1600 mL/min=23 mL/kg/min, will result in a PFC recycle rate of 50 mL/3.2 min=16 mL/kg/min, which should allow for cooling rates of more than 50% of the demonstrated 24° C./hr at 30 mL/kg/min (i.e., approximately 12° C./hr), depending on specific heat capacity of the subject. Even such lower rates are higher than previously reported for animals or humans using non-bypass cooling or any other method of external cooling likely attainable in the field. Moreover, they are still fast enough for neurological emergencies.

In Example 6, infusion volumes were cut down.

EXAMPLE 6

MMLV With Increased Suction Rates

In Example 6, FIG. 9, PFC infusion rate was maintained at 46 mL/kg/min (910 mL/min in a 19.8 kg animal), but infusion volumes were cut to 20 mL/kg (with an infusion time of 25 seconds). Suction rates were increased by engineering modifications which decreased resistance in the suction path. Effective PFC turnover in this model reached 27 mL/kg/min, and rates of cooling for the "core tissues" of the animals (Compartment #1 plus Compartment #2) reached 30° C./hr. This is the brain cooling rate. The animal was cooled only 5° C. before infusions were stopped, and the large 1.0° C. "after-rise" which then occurred (half-time 6 minutes) illustrates the difficulties of cooling an animal very quickly with any method which uses the circulation as the chief heat transfer medium, such as MMLV or cardiopulmonary bypass. Peripheral vasoconstriction in very rapid central cooling always makes "overcooling" necessary, in order to end at the desired core temperature after final equilibration. In this example, a cooling of 6.0° C. core/brain temperature would have taken about 12 minutes. This is the time required to remove enough heat to permanently cool the animal by 5° C. Uniform cooling of 5° C. over 12 minutes (⅕ hr) gives an effective cooling rate of 25° C./hr (5 C÷⅕ hr) over this range. Specific heat capacity calculated in this experiment by previously detailed methods gives a value of 0.79 kcal/kg/° C.

Efficiency

In FIGS. 3–6 it can be seen by examining venous and arterial temperature curves that at slower infusion rates the venous/arterial temperatre difference has a chance to go to zero, or nearly zero, before new PFC is infused, indicating an unused or inefficient length of time in which heat is still being transferred from blood to body, but no longer from lungs to blood. This happens even at the fastest inspiratory infusion rates of 50 mL/kg/min, if infusion cycles are too long due to overlong suction, or deliberate induction of dwell time (see temperature FIGS. 7 vs. 9 and 9a from Examples 4 vs. 6). Only with very short cycle algorithms does significant A-V temperature difference remain throughout the cycle. Shorter lavage cycle times then 15 seconds are expected to demonstrate a loss of efficacy, because if "residence" times for PFC in the lung are cut to the order of a few seconds, it is possible that any given infused volume of PFC can be removed from the lung before it has gone far enough toward reaching thermal equilibrium.

This maximum where area under the A-V temperature curve is largest represents the greatest heat transfer, and the best overall efficiency for this particular infusion rate. For all but the shortest loading times (<approximately 15 sec), the most successful algorithm (in terms of rate of heat transfer) is generally to unload gas-mixed PFC at the maximum possible rate, directly after an infusion ends. Typical infusion volumes load PFC to ⅓ to ⅔rds total lung capacity. In some examples to follow, the efficiency problems of very short cycles ans small lavage volumes will be illustrated.

EXAMPLE 7

Reliability of Cooling Rates in MMLV

FIG. 10 shows body temperatures of a group of 5 animals (mean wt 20.6 kg) subjected to MMLV with chilled PFC, under reasonably identical conditions. These conditions were chosen on the basis previous experiments to result in a rapid core .body temperature drop of about 7 C, resulting in a final equilibrium temperature drop of 5 C. This was chosen to be indicative of an emergency hyperthermia situation, in which emergent cooling by more than 5 C would not be expected to be necessary. In order to achieve cooling rates close to the maximally obtained previous rates, an infusion volume was set at 50 mL/kg/min for all animals for 20 seconds (16.6 mL/kg), with suctioning controlled by pressure, and averaging about 15–17 seconds (average cycle length was 37 seconds).

Animals began at normal body temperature, and were cooled with rapid cycling of PFC for exactly 18 minutes, with results shown. Average amount of PFC cycled was a total of 11.3 L per animal, or 550 mL/kg. Body core temperature dropped by 7.3+/−0.4 (S.D.) C over 20 minutes, with final equilibrium temperature reached, after thermal compartment equilibration, of −6.0+/−0.13 (S.D.) C. The animals lost 4.2 Kcal/kg, and the average temperature difference of fluid infused to fluid removed was 17 C., for an average heat transfer efficiency of 60+/−8%. This temperature drop for this heat gave calculated heat capacities for the group of 0.73+/−0.1 kcal/kg/C.

In FIG. 10 the curve of typanic temperatures over time for this group of animals is compared with anaesthetized controls cooled by packing them in ice. Cooling rates with MMLV were not only 4 to 8 times as fast, but were also uniform and predictable.

EXAMPLE 8

Computer Controlled MMLV

FIG. 6 is an illustration of a device for administration of Mixed-Mode Liquid Ventilation (MMLV). Such a device, designed in prototype by Korr Biomedical, Inc, Salt Lake City, Utah, was. built under direction of the authors, and used in the following illustrated examples. In this device, PFC is pumped and suctioned by the usual methods, but a computer actuates a set of valves which divert PFC from recirculation from a holding reservoir through a heat exchanger, into the animal instead. During suctioning of PFC, re-circulation of PFC continues through a bypass loop, so that the pump may run continuously.

The computer-controlled valve assembly allows infusions of cooled or warmed PFC into a catheter which is positioned in an endotracheal tube connected to a gas ventilator. PFC is also conditioned by being passed through a silicone membrane oxygenator and filters to remove respiratory tract secretions and bacteria. The computer monitors airway infusion, and has a cut off for high pressures on infusion and suction cycles. In the best implementation of the present invention, the ventilator is also controlled by the same computer, which monitors airway pressures and adjusts both PFC infusion and gas ventilation rate and tidal volume to insure that airway pressures do not exceed critical values. Pressure during suctioning is also monitored to insure that suctioning halts when liquid return slows, an event which is marked by peak inspiratory pressure reaching 2–5 Torr. In the most general implementation of the device, PFC infusion can be continuous, or it may be timed and pulsed with each inspiration. In the following examples, PFC is infused continuously.

FIG. 10a shows the result of using this method with 3 animals, as compared with the 5 in the FIG. 10 discussed above. Although the machine-cooled animals received very nearly the same amount of cold PFC (650 mL/kg), and even more heat extraction as calculated from maximum inspiratory and expiratory fluid temps (5.3 kcal/kg), they did not cool as fast, as seen in the FIG. 10a. (net cooling of only 4.5 C).=75% that of the hand controlled 20 sec infused group in FIG. 10. Unrealistic heat capacities calculated from these numbers (1.2 kcal/kg) makes it obvious that the problem is temperature data from the inpiration and expiration fluid which could not be fairly approximated by a rectangular integral. Assuming these animals had much the same heat capacity as the others, suggests that they were cooled only 75% as efficiently, for a total efficiency of 75%×60%=45%.

Analysis of Thermal Transfer Efficiency From Examples 7 and 8

Analysis of temperatures of mixed return lavages (suctioned PFC fluid) after dwell times of 2 to 7 minutes in the lungs of dogs (such as the dog in Example 3) has shown that at dwell times from 15 seconds to 2 minutes, temperature of the return liquid stabilizes, meaning that heat transfer from lavage fluid to dog has essentially stopped, at this time scale. However, the mixed lavage temperature is typically 5–7° C. lower than the temperature of the experimental animal, meaning that some cold lavage PFC remains in the animal's trachea, which does not equilibrate as rapidly as the remaining fluid, as discussed in Example 3. The rate at which fluid in the trachea equilibrates with the body can be estimated from the half-time of esophageal temperature rise in Example 1, which is in the range of 2 minutes, as discussed in Example 1. The equivalent VOLUME of fluid in each lavage which does not equilibrate rapidly (but instead with a half-time of 2 minutes), can be estimated from the thermal efficiency for each trial. The equivalent volume of cold PFC in a lavage which receives no heat during a lavage cycle, or "equivalent unequilibrated volume," may be calculated as the total lavage volume (V-LAV) multiplied by the quantity (1- thermal efficiency). In Example 7 (5 hand controlled lavage MMLV dogs) the equivalent unequilibrated volume is approximately 16 mL×(1−0.6)=6.4 mL. This unequilibrated volume is effectively a thermal "dead space" volume (VD-therm), and this terminology will be used for it. In Example 8, (3 machine-cooled dogs) the VD-therm volume is 8 mL×(1−0.45)=4.4 mL.

The thermal dead space volumes (VD-thern) calculated above (6.4 and 4.4 mL/kg) are comparable to the physiologic and anatomic dead space of dogs, which is approximately 6.5 mL/kg for animals of 18 kg size. The physiologic dead space is that space in which ventilatory gas-exchange does not occur, and therefore, in gas-exchange terminology, the fraction defined as [dead space volume/tidal breath volume] is termed the "wasted fraction" of the gas tidal volume. In ventilatory heat-exchange, by analogy, the fraction [VD-therm/V-LAV] is the thermal "wasted fraction" of each liquid lavage (considered here as a liquid tidal breath). Since VD-therm does not increase in Example 8 by comparison to Example 7 (the calculated value in Example 8 is actually lower), the lowered efficiency of Example 8 is not due to insufficient time for heat transfer to occur in the peripheral lungs. Therefore, this process must proceed very rapidly, in less than the 15 seconds available in Example 8. Instead, the decreased efficiency in Example 8 occurs because the lavage size in Example 8 is much closer to the anatomic dead space of dogs than the lavage volume in Example 7, and thus, more liquid ventilation is "wasted", from the thermal point of view, in Example 8.

Although the VD-therm volume calculated in Examples 7 and 8 is close to the anatomic dead space of dogs when lavage cycle times are from 15 seconds to about 40 seconds, this will not be true for all possible values of lavage cycle time. Thermal dead volume (VD-therm) will be expected to decrease to zero over very long dwell times >>2 minutes, since heat diffuses into the tracheal and large airway spaces. VD-therm will be expected to increase to a value larger than the anatomic dead space volume, when lavage cycle times fall substantially below 15 seconds (ie, more then 4 lavages/min). This is because, at some point, as lavage becomes more rapid, equilibration will fail to occur, even in PFC which is not in the thermal dead space volume (ie, in PFC in the peripheral lung). The limits to rapidity of lavage imposed by failure of non-VD-therm PFC to equilibrate, are unknown. However, they must occur at lavage frequencies greater than 4 lavages/min. We have demonstrated that at lavage times greater than 15 seconds, the best cooling efficiency allows no more PFC residence time in the lungs than is needed to add and remove PFC. Also, efficiency is improved if the "wasted fraction"=VD-therm/V-LAV of each lavage is kept low, which in practice means that efficient PFC lavage volumes must be at least several times the thermal dead space volume (VD-therm). During rapid lavage, this VD-therm volume -is expected to be about the same magnitude as the healthy physiologic gas-exchange dead space volume, which is similar to the anatomic dead space volume. In healthy humans, the anatomic and physiologic dead space volume are approximately 2.5 to 3 mL/kg, so that efficient PFC lavage size for humans (after subtraction of circuit dead space) will be expected to be greater than 3 times VD-therm, or at least 9 mL/kg. This would give a wasted fraction of 3/9=0.33, for each lavage (i.e., a net one third of each lavage will fail to transfer any of its thermal differential to the patient). At lavage volumes in this range, the increased thermal transfer efficiency causes cooling power to rise rapidly, as lavage size is increased, even at the same values for total amount of liquid infused and removed per minute (=liquid minute-volume). For example, in humans, a lavage volume of 12 mL/kg would be expected to have a wasted fraction of 3 mL/12 mL=0.25, and thus would be expected to be about 0.33/0.25=1.32=32% more efficient (in terms of cooling power per mL of cold PFC infused) than a lavage volume of 9 mL/kg (these expectation values are approximate, and are given to illustrate the general method only). Just as is the case in gas-exchange during mechanical ventilation, the existence of a relatively fixed thermal dead space volume at the lavage cycle times of interest, implies that larger tidal breaths (i.e., larger liquid lavage lung loads) are more efficient, per unit of minute-volume. Pressure constraints will probably limit lavage volume in humans to less than 20 mL/kg, However, such lavages can probably be given at rates of at least 4 lavages per minute without loss of any heat transfer efficiency due to failure of the PFC in the peripheral lung to equilibrate thermally with blood flowing through the lung.

EXAMPLE 9

Blood Gas Measurements May be Normal During MMLV, Even Without Cooling, and at the Fastest Liquid Infusion RateS In the experiments discussed herein, a variety of physiological parameters were monitored to establish the effects of MMLV on hemodynamics, gas exchange, and lung function both before (baseline/control conditions), during, and after the procedure. As previously noted, TLV, except under basal conditions, results in progressive hypercapnia with associated respiratory acidosis. Similarly, TLV is constrained as to the $VO_2$ that can be delivered to the animal in hypermetabolic states. The purpose of the sophisticated physiological monitoring discussed below is to assess the safety and efficacy of MMLV in inducing hypothermia. In addition to evaluating the animals' condition via discrete physiological measurements, the animals were allowed to survive for periods ranging from 24 hours to 2 weeks or more following the experiments in order to evaluate the effects of the procedure by clinical, laboratory, and histopathological criteria.

Animals subjected to MMLV were instrumented for mean arterial pressure (MAP), central venous pressure (CVP), mixed arterial oxygen saturation ($SpO_2$) and central venous oxygen saturation ($SVO_2$). Arterial pressure was monitored via a line inserted into the abdominal aorta via open cut-down of the femoral artery. CVP and $SVO_2$ were monitored via a fiber optic pulmonary artery (PA) catheter advanced via open cut-down of the femoral vein to the level of the right atrium.

Arterial and venous blood samples were drawn before, during, and after the procedure to assess the following parameters: pH, $pCO_2$, $pO_2$, sodium, potassium, chloride, ionized calcium, lactate, hemoglobin and hematocrit. For a number of experiments (FIGS. 11 and 11a) central venous and arterial blood gas samples were drawn every two minutes during the active cooling phase.

The following respiratory parameters (gas phase) were monitored and acquired in some animals using a Novametrix Medical System (Wallimgford, Conn.) $CO_2SMO$ Respiratory Profile Monitor inserted into the ventilator circuit above the endotracheal tube. These parameters were: respiratory rate (RR), end-tidal $PCO_2$ ($EtCO_2$), minute $CO_2$ production ($VCO_2$), mean airway. pressure ($MAP_a$), minute volume (MV), inspired tidal volume (VTi), expiratory volume (VTe), peak inspiratory pressure (PIP), positive end expiratory pressure (PEEP), and peak inspiratory flow rate (PIF).

Respiratory Mechanics and Gas Exchange Data From Example 6

FIG. 11a and 11b show representative paO2 data from the experiments in FIG. 10 and 10a, throughout a decrease in core body temperature of ~5° C., or when being given body temperature PFC. The paO2 at 100% O2 does not undergo significant fluctuations when cold PFC is given, but on room air, the A-a gradient typically falls by 20-Torr for a day after PFC has been used, then recovers over the next day. For warm PFC cycling, it is interesting that even with oxygenated PFC, paO2 dropped signifcantly while the dogs breathed normothermic PFC, indicating a signficant shunt and possibly V/Q mismatch. This, interestingly, was temperature dependent (the only variable). It was seen in automated and hand controlled trials. It remains unexplained, but perhaps represents a cold-prevented problem with vascular opening, which was not seen with body-temperature PFC given at the same rates and pressures. These data indicate that the volume of oxygen delivered to the tissues of the animal is adequate throughout the entire period of MMLV.

Figure 11D:
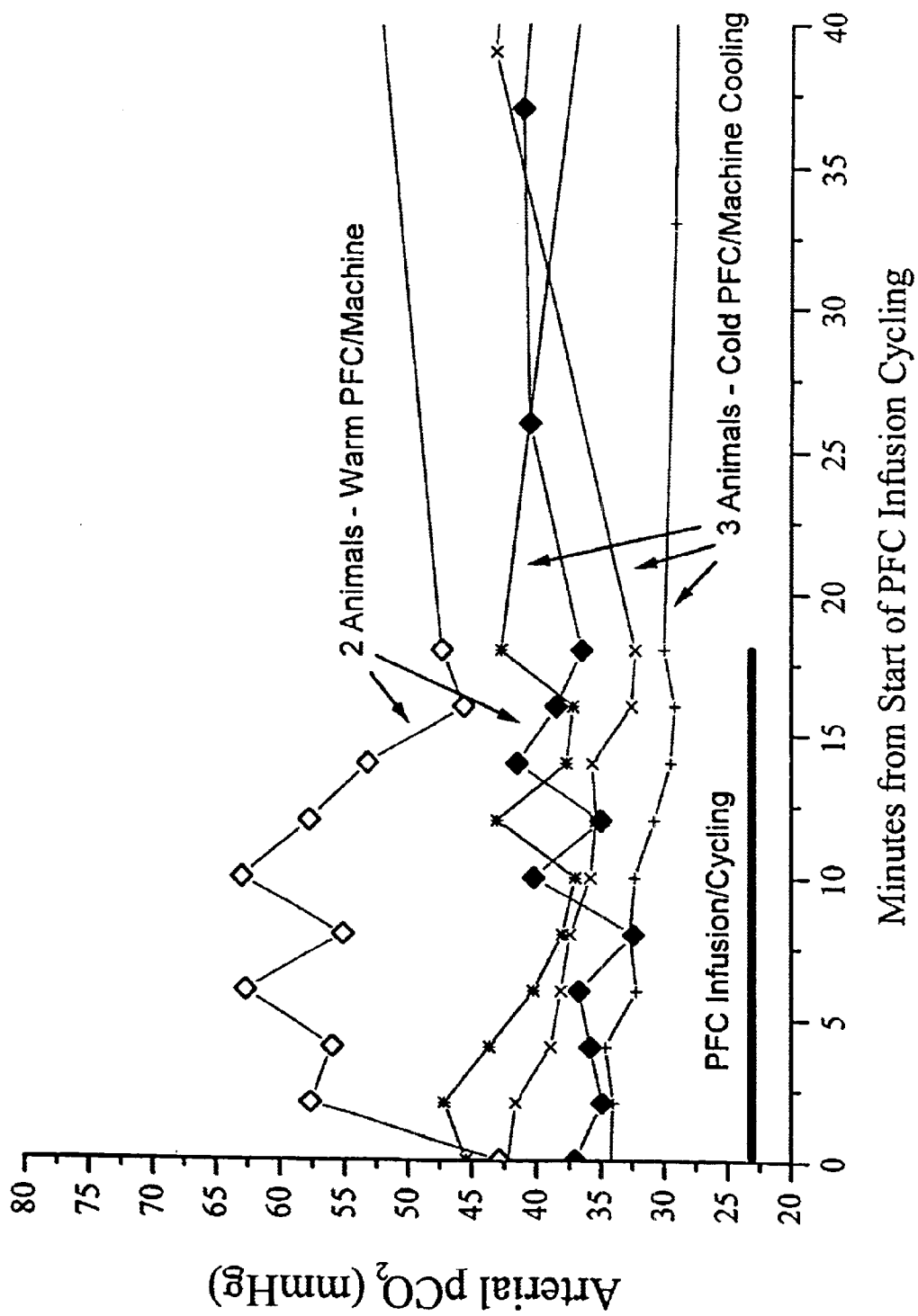

Control of $CO_2$ Removal May be Maintained Even at the Fastest Warm PFC Infusion Rates FIGS. 11c and 11d show pCO2 direct blood gas measurements (NovaStat II machine) during the active phase of cooling in the same groups. Here the same trend is evident, with cooled animals doing much better on gas exchange. Measurements of directly-obtained arterial paCO2 (femoral artery blood draws) show paCO2 to be well-maintained in cold PFC cycling in MMLV, but that many of these protocols were not sufficient to remove CO2 production when identical infusions of body-temperature PFC (38 C) was used as a control for the effects of chilled PFC. Again, animals had no difficulty with CO2 build-up in either manually controlled or machine controlled MMLV cooling, but a large difference was seen between dogs ventlated with body temperature liquid (no more than 0.5 C higher than their blood temperature—not high enough to increase metabolic rate significantly), vs identical liquid 0 to 5 C. This phenomenon also remains unexplained (some possible answers are considered below).

Of note is the last animal given machine ventilation (FIG. 11d) which also was given adequate gas ventilation, since the CO2 difficulty in warm MMLV was known. This animal had no CO2 buildup despite full rates of infusion (in fact, at rates slightly higher than standard—63 mL/kg/min). This data suggests that the CO2 problem can be solved, at least in the sort term, by increasing gas ventilation with MMLV—a luxury not available with TLV. Calculations of minute volumes using CO2SMO data suggest that these animals had been under ventilated with gas by at least 50% with MMLV, with no compensation, but had withstood this without problem in the cold. On analysis of data from these experiments, it was found that at these very fastest PFC infusion rates, pressure limitations were forcing a large decrease in volume of inspired gas breaths, and thus gas ventilation was not proceeding optimally. When the protocol was altered to allow small infusions (8 mL/kg/min) and slightly more time for normal gas ventilation (with 10 seconds given for infusion and 5 extra seconds for full gas ventilation allowed after each 5-second suction, for a 50% infusion duty cycle), CO2 was maintained at normal levels during lavage with 62.5 mL/kg/min body temperature PFC, over 18 minutes (see FIG. 11b). These are essentially identical total PFC total ventilation rates (62 mL/kg/min at 50% of time=31 mL/kg/min) rates as used for the other animals in this series. These data are evidence that MMLV is capable of achieving adequate $CO_2$ removal under many circumstances, in sharp contrast to the results obtained in TLV over comparable time courses.

A sharp decrease in gas-ventilation minute-volume observed at the same ventilator pressure parameters, when PFC infusion is warm rather than cold, implies that the compliance of the lung is much less when PFC lavage is warm, than when infusion is cold. This decreased lung compliance due specifically to warmed PFC may result in greatly decreased gas ventilation minute volume at the same pressure settings, and requires that gas ventilation parameters be reset. A preliminary hypothesis, not yet verified directly, is that under warm lavage, opening of some pulmonary arteriolar beds causes relative engorgement of the lungs with blood, producing the greater V/Q mismatch seen with warm MMLV, and also producing a greater loss of lung compliance.

Figure 12:
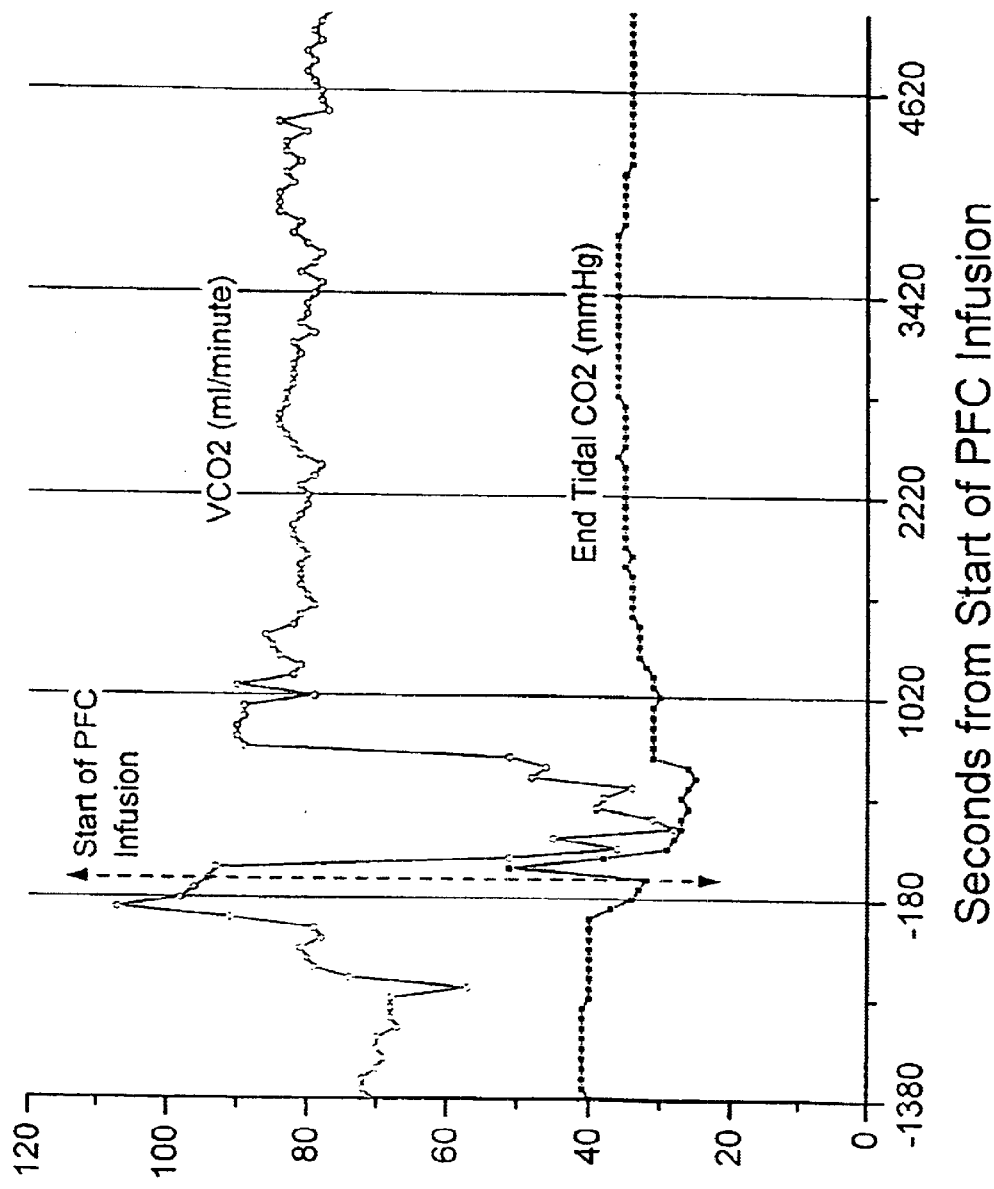
FIG. 12 shows end-tidal carbon dioxide concentration ($pCO_2$) and minute carbon dioxide production ($VCO_2 = dV/dt$) during a MMLV induced decrease in canine body temperature of 5° C. VCO2 was measured using a Novametrix Medical System $CO_2$SMO Respiratory Profile Monitor inserted into the ventilator circuit above the endotracheal tube.

Although the loss in gas minute-volume is less in cold MMLV than in warm MMLV at the same gas ventilator pressure and rate parameters, the technique of cold MMLV does produce some loss of gas minute ventilation. Liquid-loaded lungs, even when loaded with cold PFC, have less compliance for additional gas volume expansion, than do healthy, adult, surfactant-containing empty lungs containing no PFC liquid. In healthy lungs, this appears to be a simple effect of the extra volume of the PFC, contributing to total lung filling. FIG. 12 shows preliminary data suggesting how cold MMLV is able to automatically compensate, in terms of CO2 elimination, for the loss of gas minute-volume.

FIG. 12 shows combined $EtCO_2$ and $VCO_2$ data during cooling (Example 6) by 5° C. using MMLV. Preliminary examination of this data reveals a profound decrease in both $EtCO_2$ and $VCO_2$ which would seem to indicate decreased $CO_2$ elimination. However, these data are misleading since they reflect only the $CO_2$ which is present in the expired gas from mechanical ventilations. An additional amount of $CO_2$ is removed in the PFC which is loaded and unloaded from the lungs, and this volume of $CO_2$ is not measured by the capnograph in the gas path since it is dissolved in the PFC liquid and removed with it.

Evidence that the missing volume of $CO_2$ is not retained in the animal during MMLV is seen at the conclusion of the experiment where both $EtCO_2$ and $VCO_2$ return to near baseline levels and continue to remain at normal levels for over 1.5 hours without significant rebound. An arterial blood gas drawn 3 minutes after the procedure revealed a temperature-corrected $paO_2$ of 535.9 mmHg, a $paCO_2$ of 35.8 mmHg and a pH of 7.380 indicating an absence of hypercarbia and associated respiratory acidosis at the end of the experiment. This was true even though the $VCO_2$ had remained close to baseline. The temperature-corrected $paCO_2$ prior to the start of MMLV was 45.1 mmHg.

Quantitative Discussion of $CO_2$ Removal During Experiment Example 6

It is apparent from the data values for minute ventilation values using $CO_2SMO$ data, that that very significant amounts of gas are being delivered to the lungs throughout the liquid loading and unloading cycles: Indeed, for cold MMLV, Vti is 70% of baseline. This implies that significant gaseous alveolar ventilation is continuing throughout liquid loading and unloading cycles thus greatly facilitating gas exchange and allowing it to occur more or less independently of liquid "breaths."

Total minute gas ventilation as noted above is reduced to 70% of baseline and yet $CO_2$ removal in ventilatory gas falls to ~40% of baseline. Since $CO_2$ is not building up in the animal this implies that ~60% of $CO_2$ production is being removed in the suctioned PFC. Therefore a 30% reduction in gas ventilation is more than compensated for by PFC ventilation. These rates of $CO_2$ removal via PFC are considerably greater than have been previously reported in the literature for TLV at these minute volumes of PFC. The improvement of $CO_2$ removal via PFC ventilation in MMLV is thus most likely due to good $CO_2$ equilibration in most of the volume of infused liquid, with a consequently small effective dead space. This results from forced mixing of PFC by gas stirring, in MMLV.

A consequence of minimization of the effective dead space (diffusion dead space plus anatomical dead space) is that smaller minute volumes of PFC may be used in ventilation and heat exchange without the loss of efficiency which occurs as a result of dead space volumes which are large fractions of liquid minute volumes. For instance, in Example 6~60% of $CO_2$ removal is carried out via PFC ventilation. This is approximately 50% of the volume of PFC normally used in TLV in dogs. In TLV, minute volumes of liquid may not be arbitrarily decreased without loss of $CO_2$ removal efficiency. However, in MMLV there is little loss of efficiency when this is done.

As seen in FIG. 12, the average minute $CO_2$ production ($VCO_2$) in this animal with PEEP off, in the five minutes prior to beginning the experiment, was 97.2 mL/min at standard temperature and pressure (STP). (Note that the one minute averaging at the beginning and end of the experiment result in false values which have been dropped from calculations). During the experiment (see Example 6), average minute $CO_2$ production (as measured in expired gas) dropped to 38.3 mL/min (STP). After the end of the experiment, average minute $VCO_2$ increased again to 88 mL/min (STP) in the 7 minutes before PEEP was re-instituted (some of this decrease is due to lowered metabolic rate after cooling). An average $CO_2$ production of 93 mL/min before and after PFC cooling gives a deficit of 93−38≈55 mL $CO_2$ (STP)/min. In this 19.8 kg animal, this deficit amounts to 2.8 mL of $CO_2$ (STP)/kg/min, which is carried away dissolved in the PFC.

According to 3M Company literature (3M Product Information Notebook), the proprietary PFC used in this experiment (3M "FC-75"=prefluorobutyltetrahydrofuran) has a $CO_2$ carrying capacity of 2 mL $CO_2$ (STP) per mL of PFC at 760 Torr and 25° C. (~average PFC suction temp, see FIG. 9). At the arterial $pCO_2$ measured just after completion of the experiment ($PaCO_2$=35.8 Torr), carrying capacity of the PFC at the suction temperature would be estimated by Henry's law to be approximately 2.1 mL $CO_2$ (STP)/mL PFC×35.8÷760=0.098 mL $CO_2$ (STP)/mL PFC. At the average infusion-removal PFC cycle rates in this experiment (27 mL/kg/min), this would result in a theoretical $CO_2$ removal capacity of 27 mL PFC/kg/min×0.098 mL $CO_2$ (STP)/mL PFC=2.65 mL $CO_2$ (STP)/kg/min. This is very close to the amount of $CO_2$ deficit measured: 2.8 mL $CO_2$ (STP)/kg/min. At 0° C. the carrying capacity is calculated to increase by 6%, which is enough to raise the theoretical $CO_2$ carrying capacity of the. PFC in Example 6. to the measured 2.8 mL $CO_2$ (STP)/kg/min. Supersaturation of warm PFC with gas dissolved at colder temperatures may also be operating to raise carrying capacity. Another possibility is that a small amount (6%) of the $CO_2$ evolved which is not recorded by the capnograph, is not dissolved in PFC but is instead removed in the suctioned gas which cannot be evaluated by the capnograph. In any case, it is apparent from this example that MMLV results in very close to theoretical saturation of cold PFC infusions with $CO_2$—further indication that physiologic and diffusion dead space with MMLV have been greatly reduced when compared with TLV.

Figure 13:
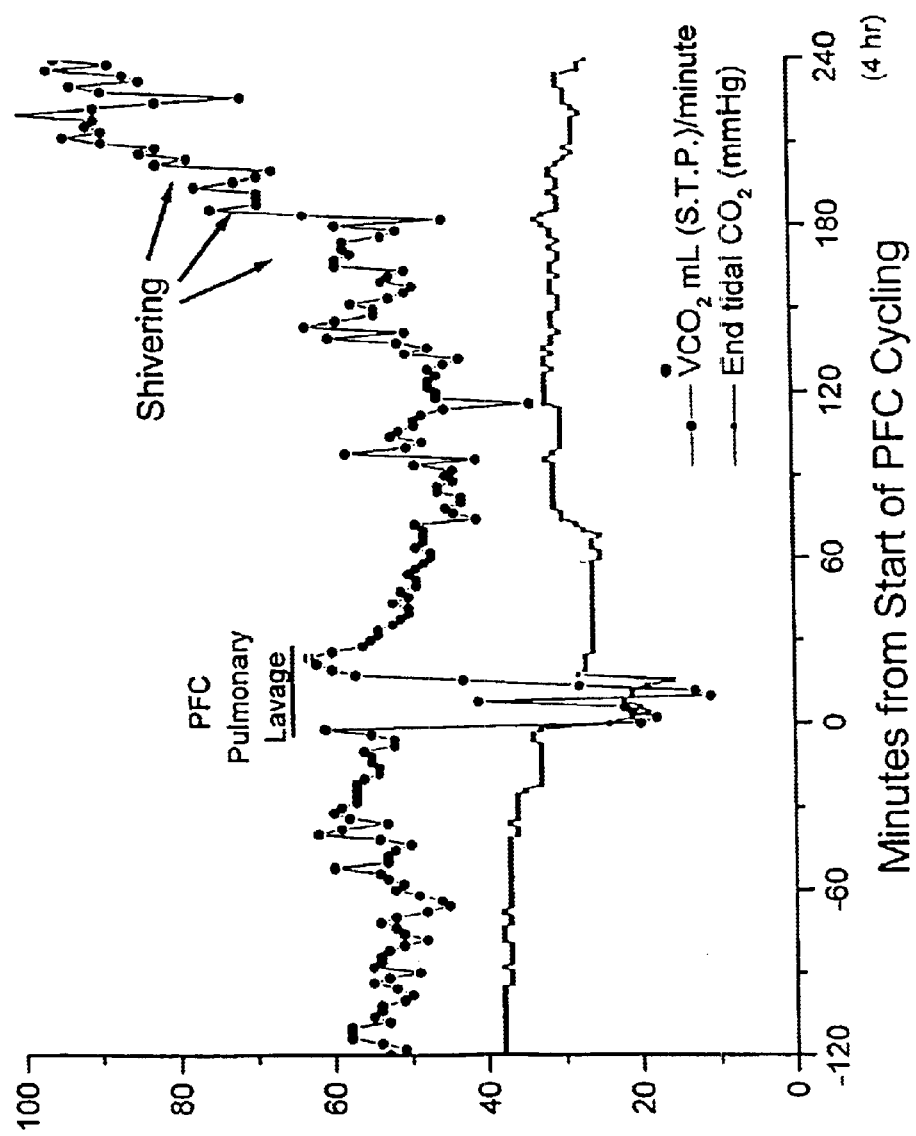
FIG. 13 Shows VCO2 measured by the above method in another dog during another rapid PFC manual MMLV lavage. This graph shows that VBO2 production is stable after PFC lavage stops, and does not rise until shivering begins. The slight increase immediately after lavage is known to be false spectrophotometric reading of PFC vapor.

FIG. 13 shows $VCO_2$ measurements of another animal given cold PFC, again with the suggestion that $CO_2$ production does not go up much (if at all) due to 18 minutes of cold lung lavage. The $VCO_2$ increase with shivering and bringing body temperature up after the procedure, however, may be clearly seen. This is an example of a hypermetabolic state which MMLV should be able to address in clinical situations.

Other Physiologic Parameters

Electrolytes and lactate levels remained unchanged prior to, during, and after the experiment in Example 6. Serum lactate was 2.0 mM prior to the start of MMLV, 1.6 mM 3 minutes after MMLV and 1.3 mM 3 hours following the procedure.

Figure 14:
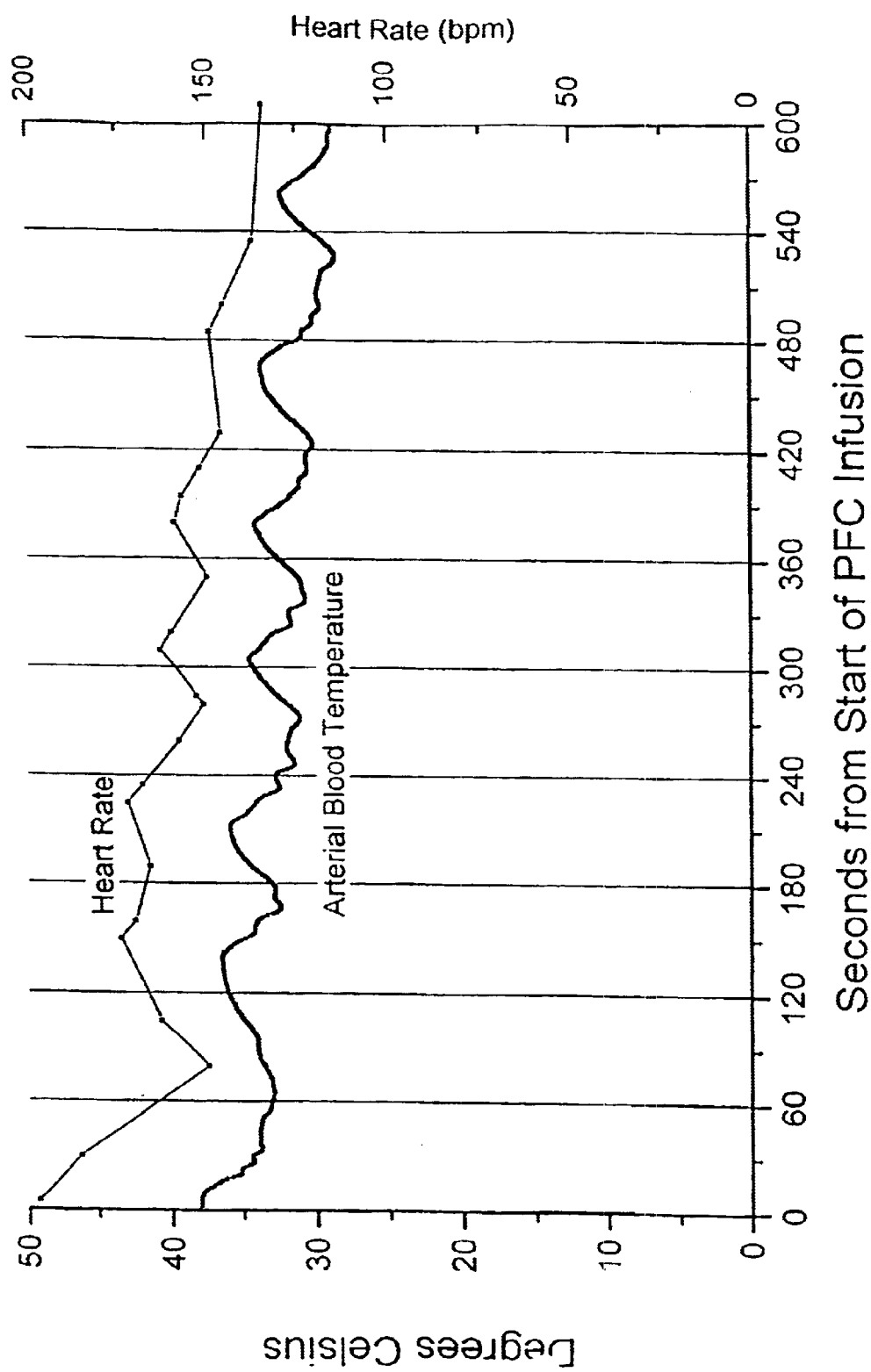
FIG. 14 shows the relationship between aortic temperature and heart rate during cold MMLV lavage in a canine. Temperatures were measured as in FIG. 1.

The hemodynamic effects of MMLV are illustrated for Example 6. FIG. 14 shows the relationship between aortic temperature and heart rate. The temperature wave form shown in this graph is a surrogate for the volume of liquid in the lung. It should be noted that of the 22 dogs subjected to ultra cold intrapulmonary cooling with PFC, no animal developed any arrhythmia other than bradycardia associated with cooling, and this was transient, even at core drops of −12° C.

Figure 15:
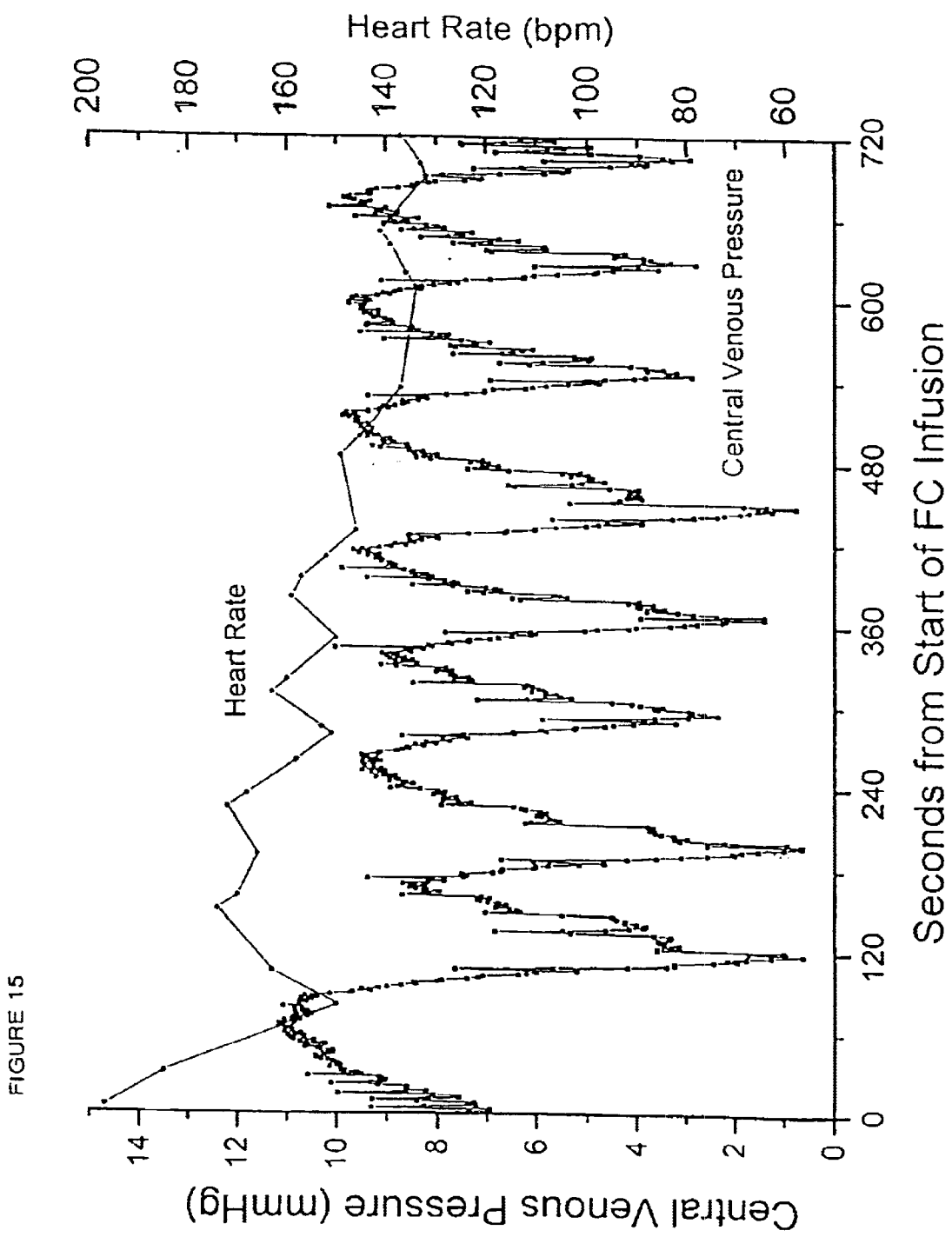
FIG. 15 shows the central venous pressure and heart rate during MMLV. Central venous pressure was monitored via a fiber optic pulmonary artery (PA) catheter advanced via open cut down of the femoral artery to the level of the right atrium.

In FIG. 14 the peaks in aortic blood temperature indicate the point where most of the liquid is unloaded from the lungs. Similarly, the nadirs in aortic blood temperature are indicative of the presence of the maximum volume of cold PFC in the lungs. As can be seen from this graph, maximal PFC loading (and the nadir of aortic blood temperature) are associated with a modest decrease in heart rate. Initially it was believed that this decrease in heart rate was due to coronary blood cooling resulting in a decrease in myocardial metabolism with a associated decline in heart rate. This may in fact explain some of the decrease in heart rate, however, as can be seen from FIG. 15, there exists a better correlation between decrease in heart rate is the increase in central venous pressure (and thus intra-thoracic pressure) associated with PFC loading.

The more probable mechanism of this decrease in heart rate is decreased preload as a result of reduced venous return secondary to increased intra-thoracic pressure peaking at the end of PFC infusion. Interestingly, heart rate rebounds above baseline when liquid is suctioned from the lungs and the venous return to the heart normalizes. This is analogous to the reflexive rebound in heart rate after the release of pressure in the Valsalva maneuver. This phenomenon occurs since intrapleural (intrathoracic) pressure has a profound effect on venous blood return to the heart and thus on preload.

Normal intra-thoracic pressure is −4 mmHg. An increase in intra-thoracic pressure to +2 mmHg requires a 6 mmHg increase in right atrial pressure (RAP). In the absence of compensatory circulatory reflexes, a rapid increase in RAP to 7 mmHg decreases venous blood return to zero. Even a modest rise in RAP as a result of PFC loading causes a drastic decrease in venous return because the systemic circulation is a very flexible compartment with the result that any increase in RAP causes blood to accumulate in this compartment and not return to the heart.

Figure 16:
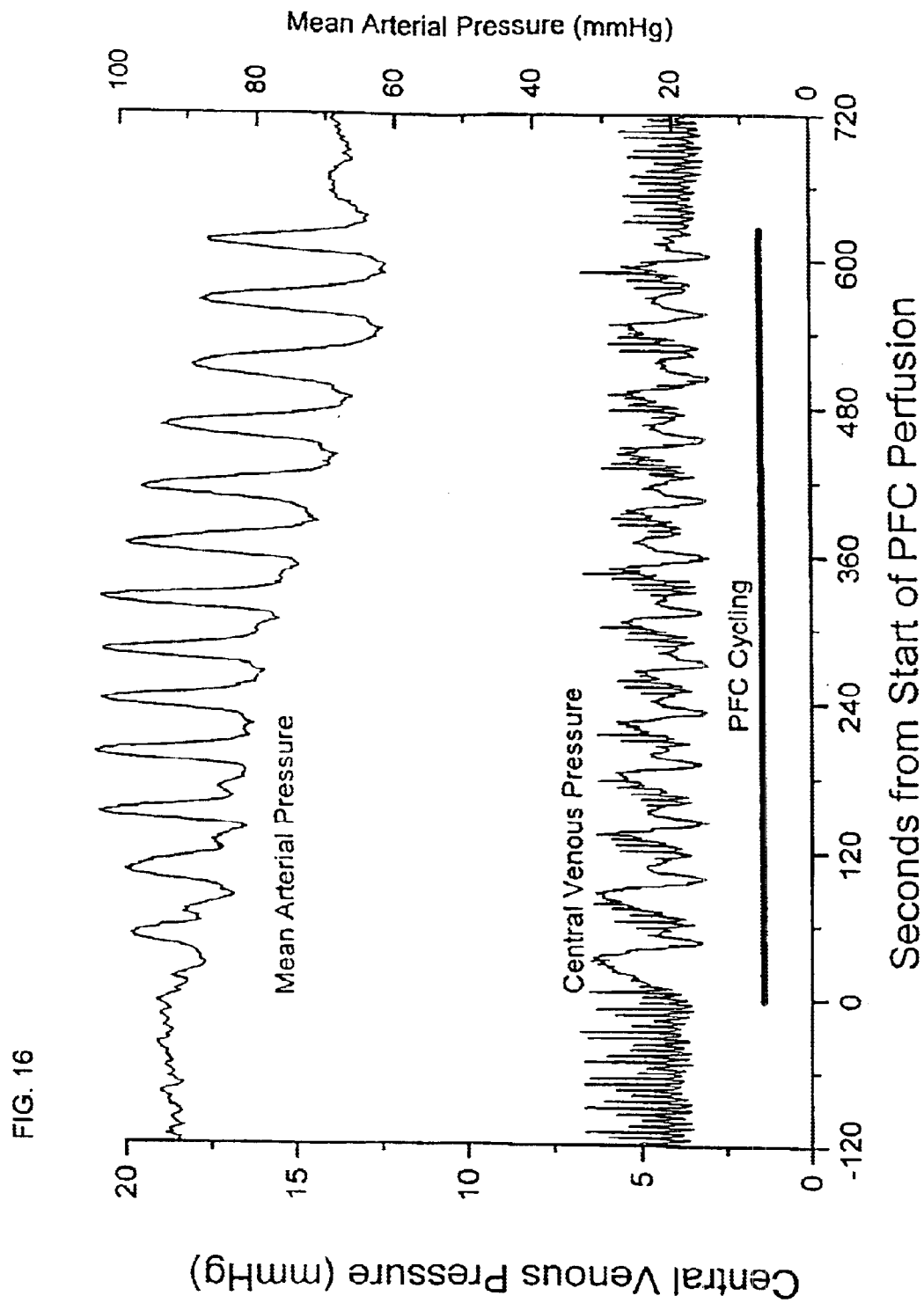
FIG. 16 shows the central venous pressure and mean arterial pressure during MMLV. Arterial pressure was monitored via a line inserted into the abdominal aorta via open cut-down of the femoral artery. Central vehous pressure was monitored as in FIG. 15.
Figure 17:
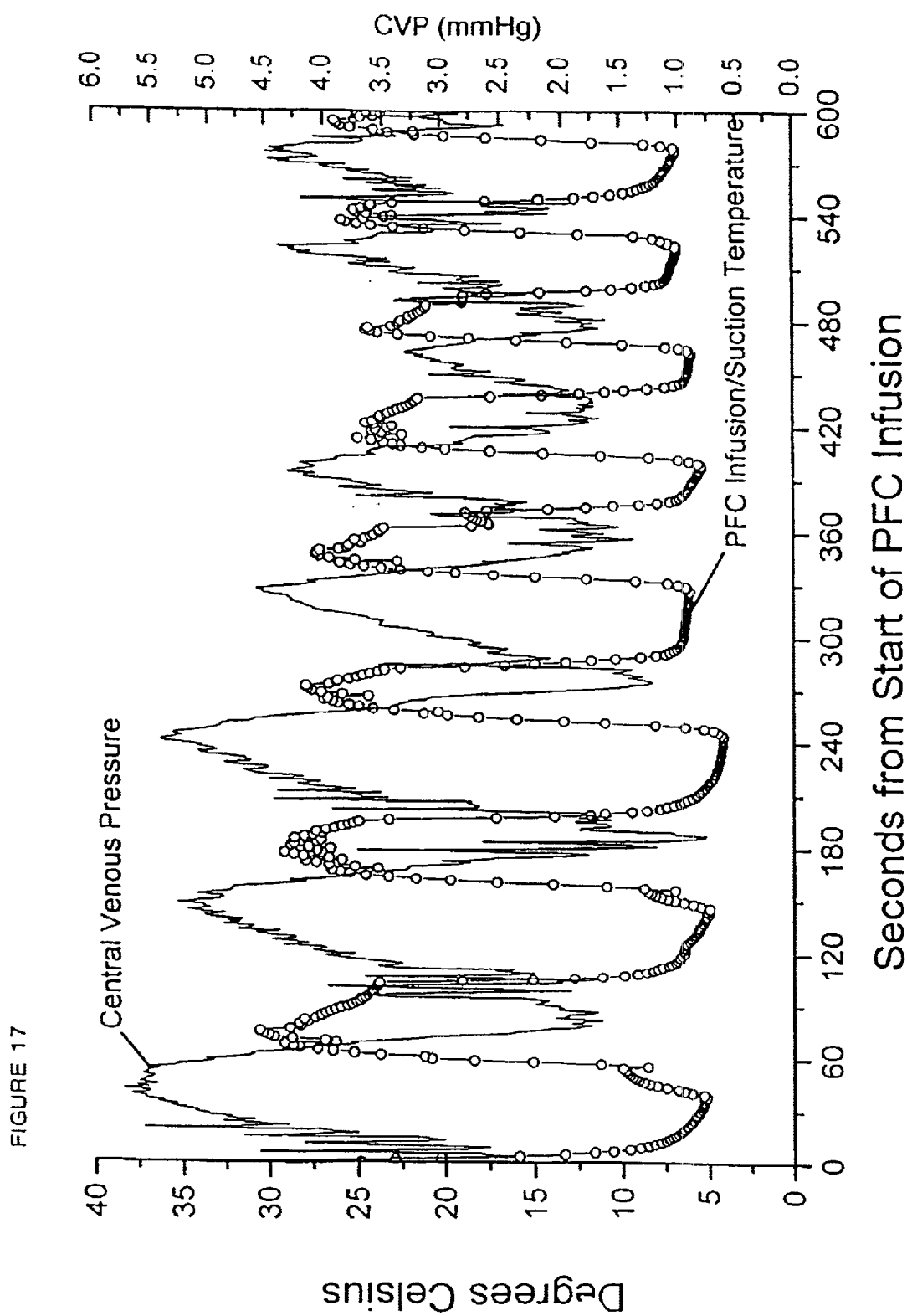
FIG. 17 shows the central venous pressure and PFC infusion/suction temperature during MMLV. This illustrates the relationship between infusion of cold PFC and venous pressure. Central venous pressure was monitored as in FIG. 15.

Lack of adequate preload (decrease in venous return to the heart) decreases cardiac output which in turn decreases arterial pressure. As can be seen from FIG. 16, the effect of increased CVP on mean arterial pressure (MAP) is even more profound than the effect of PFC loading on heart rate. Maximum intrapulmonary PFC load is associated with a temporary drop in MAP of 15 to 25 mmHg. This decrease in MAP is directly related to increased intra-thoracic CVP and thus intra-thoracic pressure. As shown in FIG. 17, CVP increases from an average of 2.0 mmHg to 3–3.5 mmHg at the maximum intrapulmonary PFC load of 50 ml/kg.

Figure 17A:
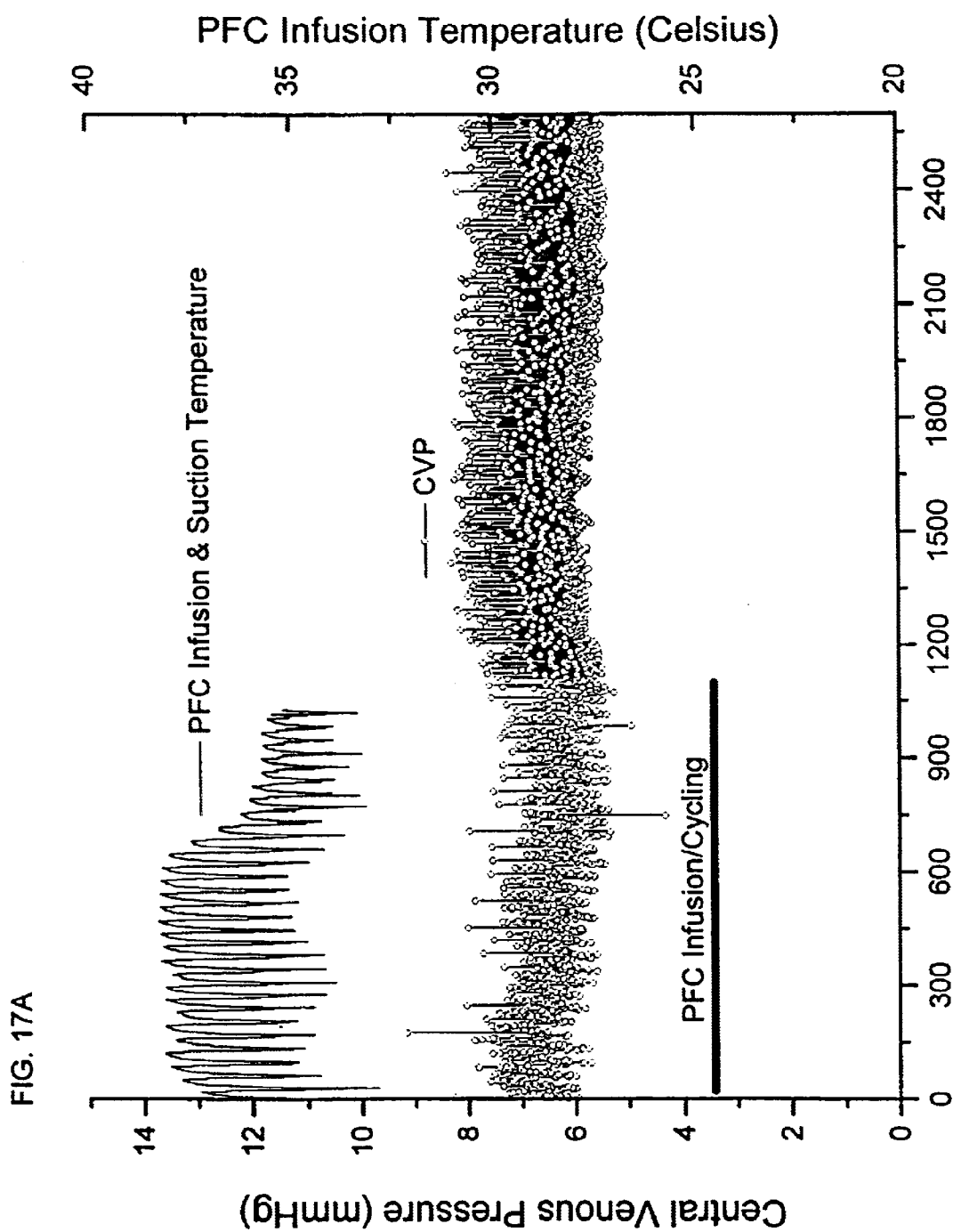
FIG. 17a shows the central venous pressure and PFC infusion/suction temperature during MMLV, as in FIG. 17, but using infused PFC at body temperature.

The relationships discussed above may also been seen in dogs loaded with body temperature PFC (FIGS. 16a and 17a), so there is no question that the bradycardia and acceleration associated with suction in these animals is an artifact primarily of thoracic pressure changes, not sudden blood hypothermia.

Figure 18:
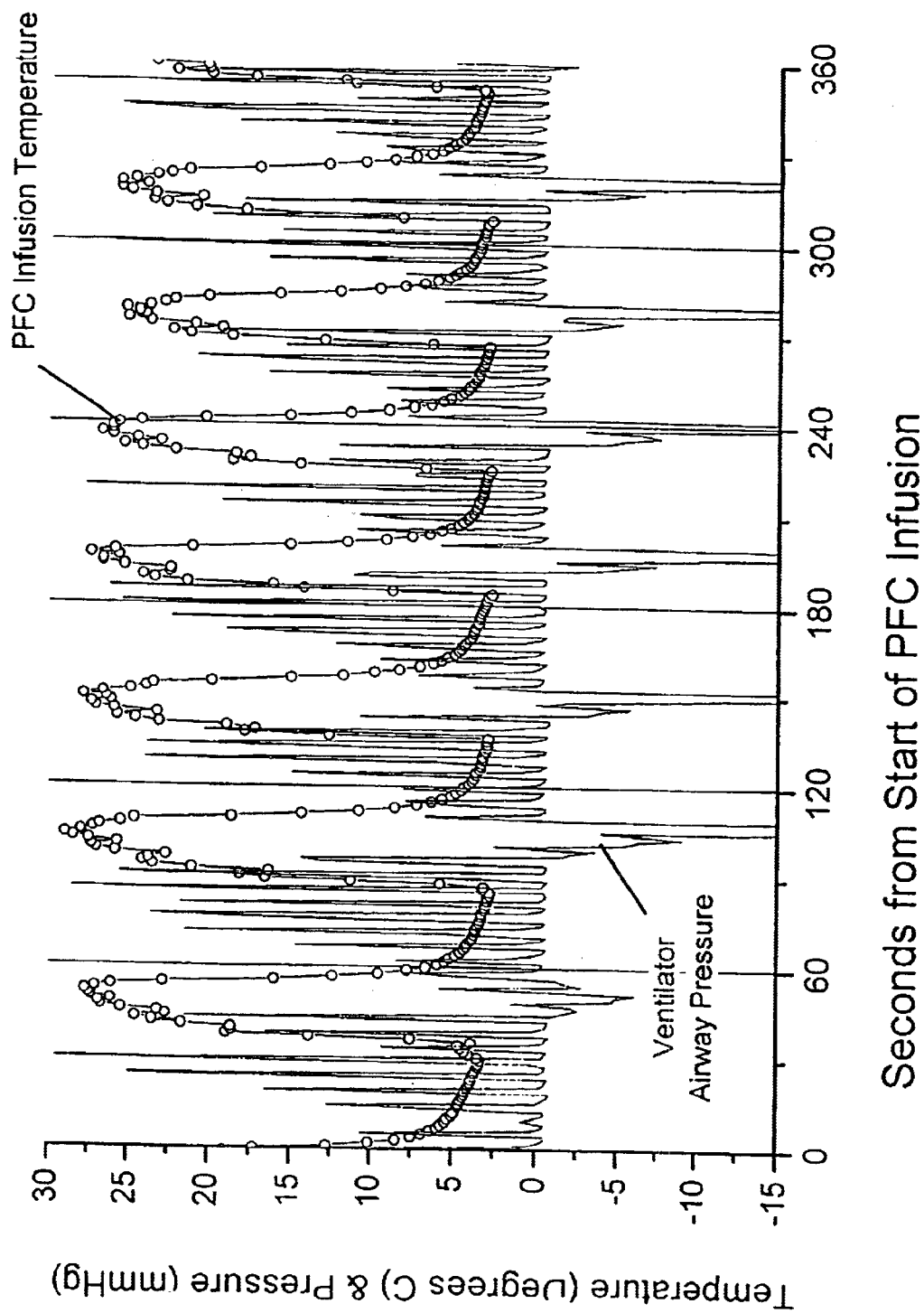
FIG. 18 shows the PFC infusion temperature and ventilator airway pressure during MMLV with cold PFC.

FIG. 18 shows the relationship between PFC load in the lungs (as indicated by PFC infusion/suction temperature curves) and ventilator gas pressure in Example 6. In this graph, PIP (peak inspiratory pressure as indicated by peaks in the ventilator pressure graph) and MAP rise steeply and nonlinearly as maximal PFC loading is achieved. In this experiment, PIPs are at 40 cm $H_2O$ by the time the last gas breath is delivered with the lungs maximally loaded with PFC. As can be seen from this data, the most effective gas breaths are being delivered at pressures of 25–27 cm $H_2O$ or less. PIPs of 40 cm $H_2O$ are associated with rapid development of baro- and volu-trauma in the dog lung. The development of a more sophisticated apparatus for delivering MMLV will allow for lower PIPs and mean airway pressures with consequent reduction in lung injury.

Effect of MMLV on Respiratory Parameters and Some Caveats About the $CO_2SMO$

Total alveolar minute ventilation decreases proportionally more than total gas minute volume, as computed by the CO2 SMO device, during MMLV. This occurs because the $CO_2SMO$ computes minute alveolar ventilation by using minute ventilation and $VCO_2$. Since 59% of the $VCO_2$ is-being removed in the form of gas bubbles in the PFC liquid, the sensor of the $CO_2SMO$ cannot detect this volume of $CO_2$ and thus the values for gaseous CO2 "alveolar minute volume" production (MV alv) total are artificially low. However, calculation of the theoretical maximum amount of $CO_2$ being removed via PFC suction shows close agreement with the estimated $VCO_2$ of the animal during MMLV. Other caveats that should be considered when using the $CO_2SMO$ in MMLV are:

a) The presence of PFC vapor in the respiratory gas being evaluated by the $CO_2SMO$ results in falsely high $VCO_2$ and $EtCO_2$ readings on the order to of 6 to 13% (ca. 2–5 ml/min or 2–5 mmHg). Similarly, flow readings are modestly effected (5 to 10%) by the increased density and viscosity of ventilating gas loaded with PFC vapor.

b) Positive VTi spontaneous values during MMLV do not reflect spontaneous respiration since the animal is anesthetized (Level III, Plane IV) and paralyzed throughout the experiment. The $CO_2SMO$ is designed to report negative pressure airflow down the ET tube as spontaneous inspiration. In fact, the large values for VTi are an artifact of suctioning PFC and gas from the lungs of the animal and the ventilator circuit at the completion of liquid unloading. Arguably, these values constitute some information about the total volume of gas/liquid removed from the animal and ventilator circuit during a liquid unloading cycle (since all liquid/gas suctioned from the lungs must be replaced by gas flowing through the $CO_2SMO$ over multiple cycles of suction) and thus may be of some use.

c) Wetting the capnographic window with PFC results in false high readings of both $EtCO_2$ and $VCO_2$ until the heater in the capnograph vaporizes the PFC. The dual beam infrared technology used in the capnographic sensor does not tolerate contamination with liquid, whether it is PFC or water.

d) Similarly, the $CO_2SMO$ is designed to measure respiratory parameters using only gas ventilation. The system operates by measuring $pCO_2$ and the absolute and differential pressures of the ventilating gas. Liquid contact, including PFC, renders the system inoperative.

The above caveats on the limitations of the $CO_2SMO$ data notwithstanding, it should be noted that following completion of the experiment and suctioning of PFC from the lungs to FRC, the total alveolar minute volume returns to baseline levels within 1–2 minutes where it remains for more than 2 hours until recovery from anesthesia and the start of weaning from conventional mechanical ventilation.

Further, despite limitations on its accuracy, the $CO_2SMO$ provides valuable data on the respiratory mechanics and physiology of MMLV. Recent changes to the $CO_2SMO$ software allow for continuous real-time acquisition of data, as opposed to 1-minute trends. Use of this enhanced capability should allow for considerable progress in optimizing the algorithms used for MMLV.

Progress in Preventing Baro-trauma

Figure 19:
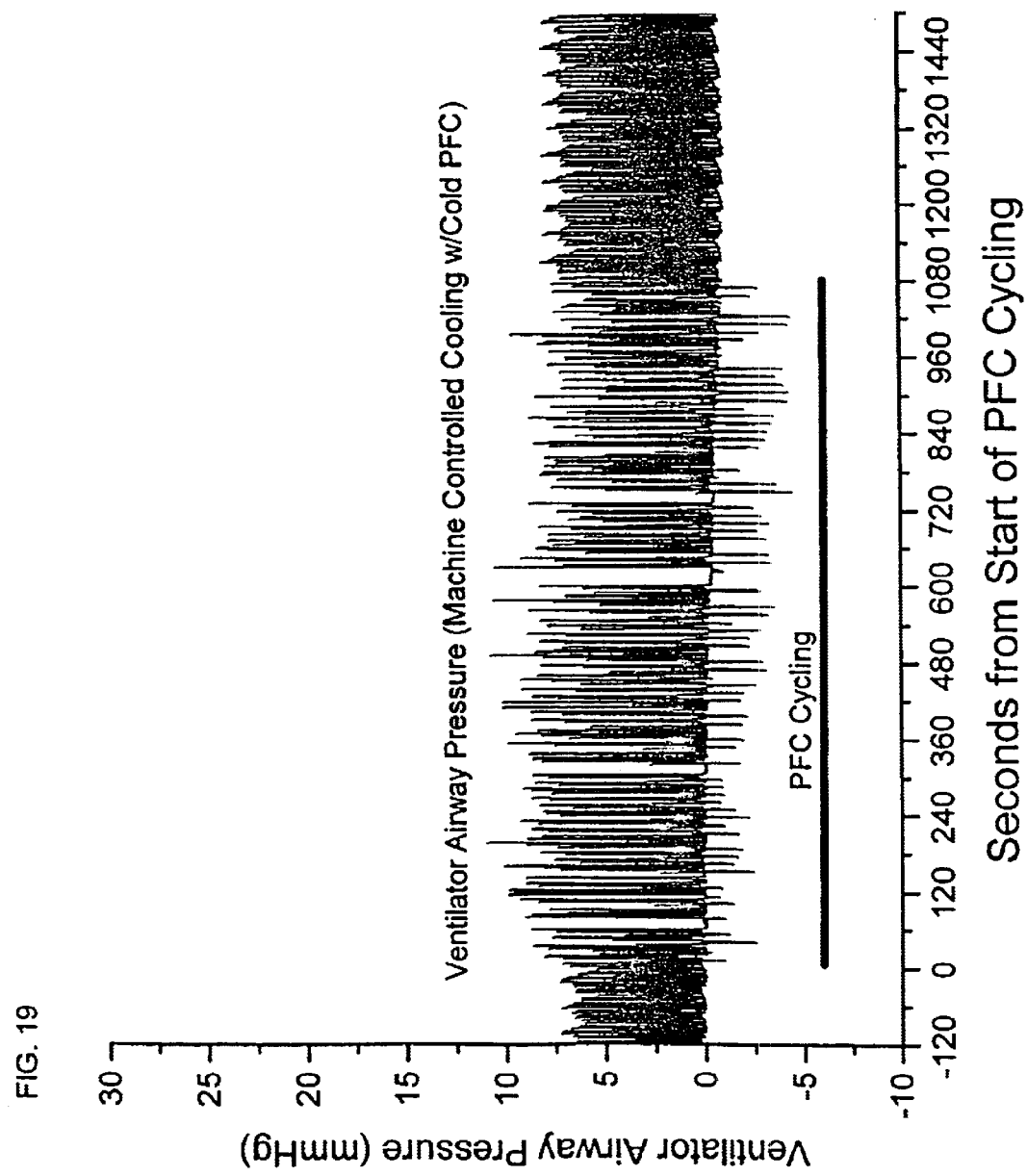
FIG. 19 shows airway pressure over time with cold machine controlled rapid PFC MMLV cycling, as in FIGS. 10a. Here, pressure control by machine is especially successful.
Figure 20:
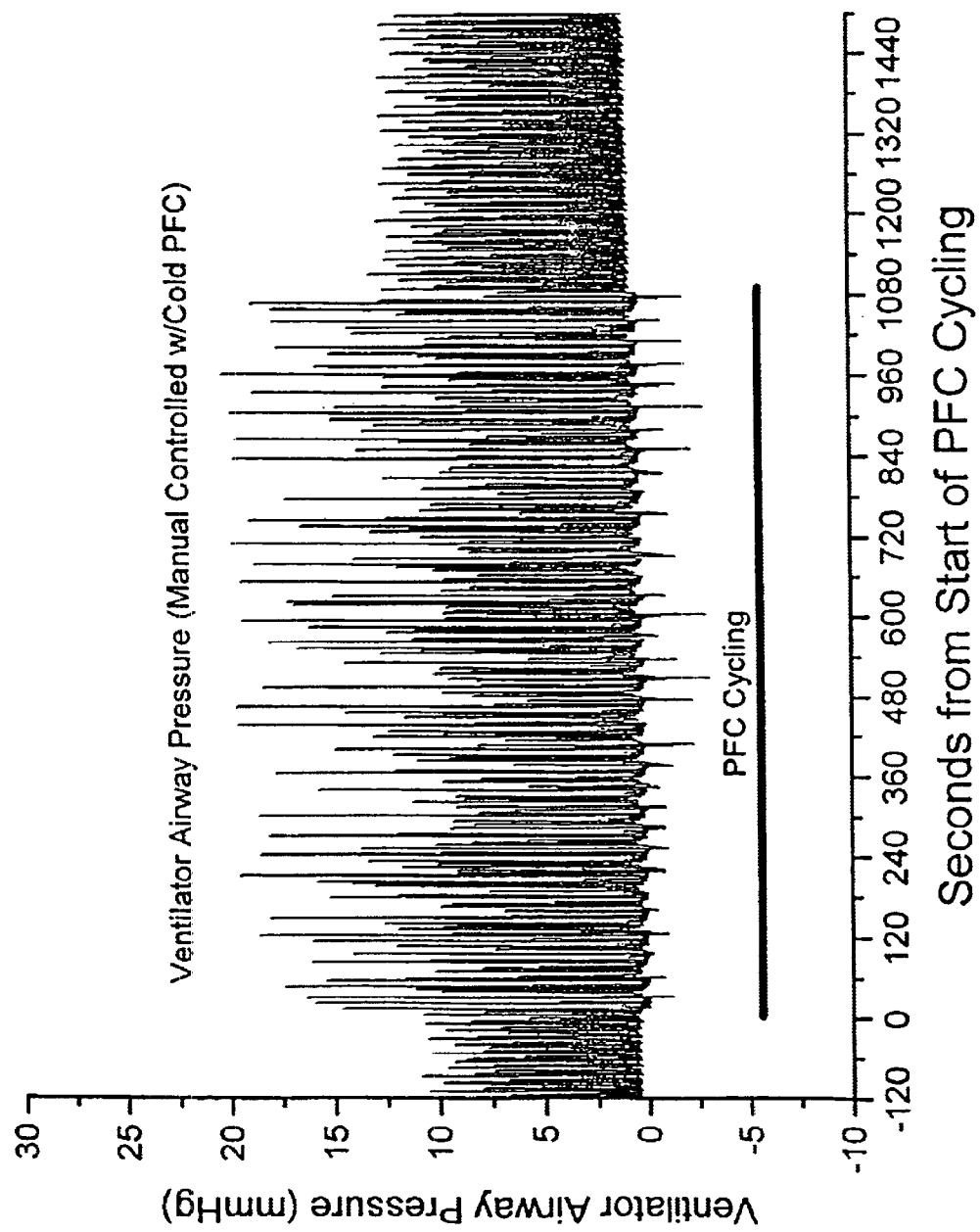
FIG. 20 shows airway pressure over time with cold manual PFC MMLV cycling, in a canine from FIG. 10. Here, pressure control by hand is especially good.

FIGS. 19 and 20 show 2 cold PFC lavage trials from 10 and 10a, in terms of maximal airway pressures, measured at the ET cuff. They differ essentially only by infusion volume (not rate) and machine control (machine control of valving, and a newer ventilator which is more sophisticated). While control of pressure is good with practice in hand-controlled mode, it is clear that the machine-controlled mode with infusions of 8 mL vs. 16 mL and better control over pressure parameters, did the best at controlling pressures in both suction and lavage.

Histopathological Evaluation

Blinded histopathological examination was performed by Ronald E. Gordon, Ph.D., Director of the Electron Microscopy Core Facility at Mt. Sinai School of Medicine, New York, N.Y. Tissues were evaluated grossly and by light microscopy using Hematoxylin and Eosin staining. All animals evaluated histopathologically were subjected to manual MMLV using the perfluorocarbon FC-75 per the protocols described herein. (No histopathology for machine controlled MMLV dogs is presently available, but these animals appear to do better clinically).

Example 2, FIGS. 3 and 4: The lungs appeared grossly normal. On light microscopy there were occasional small areas of focal edema and hyper-cellularity in the bronchioles. The heart was grossly and microscopically normal.

Full MMLV Examples:

MMLV1: The lungs looked good overall with normal gross and microscopic appearance. Large airways, smaller airways, bronchioles, alveolar ducts, alveoli and blood vessels appeared normal. The gross. and microscopic appearance of the heart was normal.

MMLV2: The lungs appeared grossly normal. The large and small airways were intact, however, the vessels appeared dilated. The bronchioles and gas exchange compartments exhibited some interstitial edema with some RBC extravasation. Vessels were apparently acutely disrupted. There was no evidence of inflammatory infiltrate. NOTE: it is the pathologist's impression that this is an acute injury probably secondary to excessive perfusion pressure during fixative perfusion due to the lack of inflammatory changes unless this animal was sacrificed acutely. (In fact this animal was clinically well with normal ABGs at the time of sacrifice which was 2 weeks post MMLV). The heart was normal on both gross and microscopic examination.

MMLV3: The lungs appeared normal in all respects except for a few scattered focal bronchiolar inflammatory infiltrates. The heart was normal both grossly and on microscopic examination.

MMLV4: The lungs and heart appeared completely normal.

As is evident from these histopathological findings, MMLV as practiced even in its currently suboptimum form results in only minor histological injury. As the preceding clinical and laboratory data make clear, MMLV is consistent with both good post-procedure gas exchange, ventilatory mechanics, and long term survival with no clinically apparent sequelae.

Optimization of the Current Protocol for MMLV

In much CO2 SMO data it can be seen that with hand-controlled relatively large lavage loads, 1–2 gas breaths that are delivered before PFC loading of the lung is at maximal levels, are too often delivered at a PIP of 40 cm $H_2O$ or greater. PIPs of 40 cm $H_2O$ in dogs are associated with baro- and volu-trauma as well as pulmonary edema due to increased microvascular permeability. As can be seen from measured airway pressures vs. PFC load in the lungs, as shown in FIG. 18, even in the worst of our manually controlled series, PIPs during MMLV averaged only 35 cm $H_2O$. Thus, no animals were permanently damaged by MMLV alone. Nevertheless it is still possible that damage was done which would not be acceptable clinically in certain situations. Thus,. optimization. of the protocol for certain clinical applications, can include one or more of the following:

a) Substitute a sophisticated (feedback responsive) pressure cycled ventilator for the volume cycled, pressure limited ventilator (Puritan Bennett MA-1) which was used to do much of the manual work and used for most of these experiments. FIG. 31 shows not only machine controlled ventilation, but the ventilator is a Servo-9000.

b) Limit PIP to no higher than 25 to 27 cm $H_2O$ and mean airway pressure to no greater than 10 cm $H_2O$.

c) Eliminate large negative intrapulmonary pressures during PFC suctioning and halt suctioning at a negative airway pressure of 2 to 4 cm $H_2O$. The rate of heat exchange might be further optimized by discontinuing suction at a PIP of +2 to +5 cm $H_2O$ at which time almost all of the available PFC would be unloaded from the lung. This would not only avoid any possibility of trauma from negative intrapulmonary pressures, but would optimize heat exchange by increasing the frequency of liquid loading/unloading cycles per unit of time.

CONCLUSION

This document enumerates multiple uses for gas/PFC-based liquid ventilation (MMLV) as a mode of efficient heat exchange due to the mixing effect of gas breaths on heat exchange medium in the small airways throughout the lung, including in the peripheral lung (gas bubble-induced small-scale PFC non-thermal forced-"convection"). This can be used in the entire range of possible liquid infusion temperatures (−10° C. to 43° C.), since prior art in PFC heat exchange relies on non augmented TLV with no gas bubbles present (Shaffer, 1994, U.S. Pat. No. 5,335,650, and Vaseen V A, 1980, U.S. Pat. No. 4,323,665).

There are other means of deliberately inducing small airway liquid mixing in PFC for purposes of heat exchange, as being essentially the same as the gas bubble method induced herein. These include but are not limited to:

A. The use of High Frequency [Oscillating] Ventilation (HFOV, or HFV) as a modality to induce small airway fluid mixing in PFC, for purposes of heat exchange. This will be true for HFOV when used with either TLV and MMLV (with and without gas, since HFOV is expected to cause nonthermal "convective" mixing and gas transport, even in TLV). HFOV has been used experimentally to obtain good $CO_2$ "dead space" diffusion with small tidal volumes (i.e., equal to the anatomical dead space) in PLV with PFCs. The suggestion and expectation that it may be used to augment heat exchange with PFC in both TLV and MMLV is novel.

B. The use of sweep-flow augmented PFC, introduced in prior art (Parker J C, U.S. Pat. No. 5,706,830, 1996) as a means of reducing $CO_2$ "diffusion dead space" by using jets of PFC delivered via two canulae directed down the main bronchi. These jets induce dead space fluid mixing, but are introduced in prior art only as aids to $CO_2$ removal in TLV. The heat exchanger in this patent serves only to buffer excess heat from the pumps, prevent hypothermia in the subject due to ventilation with room temperature liquid and prevent heat losses from the circuit tubing from inducing hypothermia. This technique is not used to deliberately to cool or warm the subject.

The proposal for the use of sweep-flow technique as an aid to heat transfer in TLV, PLV or MMLV, is novel and public disclosure of sweep-flow (increased ventilatory efficacy due to turbulent mixing of the anatomical dead space) independent of J. C. Parker, by one of us (M. Darwin) in April of 1996 predates the filing of J. C. Parker's U.S. Pat. No. 5,706,830. This patent proposes to use a Y-configuration endobronchial tube to facilitate elimination of physiologic dead space.

C. The use of deliberate combinations of HFOV, sweep-flow, and MMLV to induce small airway mixing of PFC based liquids or other suitable liquids, for purposes of heat exchange or gas exchange.

We have developed a device which uses gas ventilation specifically to facilitat e removal of PFC (or other liquid) liquid heat exchange. and gas exchange media and gas foam mixtures, from the lungs. These high rates of PFC or other liquid removal are necessary for the highest heat and gas exchange rates a non damaging pressures.

In addition, MMLV as a technique can include a novel device which controls gas and liquid ventilation separately, but in an interlocked way, in order to maximize $CO_2$ removal, heat removal and oxygen delivery.

These techniques have a number of uses, including but not limited to:

Delivering ultracold PFC infusion into the lungs, which we have found may be used safely, without cold induced lung injury. We find that it can be used safely in the temperature range below 20° C. (about −10° C. to +20° C.) for PFC infusion of any kind into the lungs. Prior art (Shaffer, 1994, U.S. Pat. No. 5,335,650) claimed the use of TLV for heat exchange only with fluids warmer than 20° C., but cooler than body temperature. We've introduced the novel idea of ultra low temperature (−10° C. to 20° C.) PFC infusion for heat exchange, as used in any kind of liquid ventilation or. liquid breathing.

These techniques are not limited to the exact techniques described. It will be noted that MMLV is susceptible to improvements in many ways by anyone skilled in the art, without departing from the spirit of the discovery that non-thermal "convective" mixing and mass transport assistance is necessary for efficient central cooling via PFC lung lavage. Cooling rates of 2°° C./hr are easily achieved by our methods, but we note that faster cooling rates are in principle easily achievable by maximizing performance of many features of our system of MMLV, and by use of features of systems which we have described above (HFOV, sweep-flow) when used in the novel way described (i.e., in conjunction with PFC for heat exchange and/or gas exchange).

Increasingly, we've found that MMLV facilitates gas exchange more efficiently for the treatment of adult and neonatal respiratory distress syndromes, pulmonary edema, and other pulmonary insults (i.e., alveolar proteinosis, chronic bronchiectasis, as well as chemical and thermal insults to the lung) which result in V/Q mismatch as a consequence of sequestration of alveoli from gas exchange by means other than either TLV, as taught by Shaffer, 1994, U.S. Pat. No. 5,335,650, and Vaseen V A, 1980, U.S. Pat. No. 4,323,665, or PLV as taught by Schutt, E G 1996 in U.S. Pat. No. 5,540,225. The use of normothermic MMLV in these conditions has the added advantage of acting to vigorously lavage the large and small airways—thus removing mucus, blood (secondary to hemoptysis or trauma), pulmonary transudate, and other harmful respiratory secretions—all far more efficiently than possible with either TLV or PLV.

MMLV can also be used for the therapeutic induction or reversal of hypothermia, including but not limited to: heatstroke, malignant hyperthermia, hyperpyrexia, stroke, head injury, post-ischemic insult, and febrile illnesses.

MMLV is useful for the companion animal and human cryopreservation patient (cryonic suspension) and for other postmortem cooling or warming of humans for the purposes of organ preservation, organ or tissue recovery, resuscitation, or facilitation of treatment of trauma patients, exsanguinating injuries, or cardiac arrest.

MMLV is a therapeutic modality to improve gas exchange, reverse or induce hypothermia, or maintain normothermia. This claim is understood to include but not be limited to shock as a result of sepsis, poisoning, chemical or thermal burns, and trauma.

MMLV can be used for the purpose of increasing the efficacy of closed chest CPR by the mechanism of raising intra-thoracic pressure during the down stroke of external cardiac compression by synchronizing liquid loading with chest compression. A corollary of increased thoracic pressure during the downstroke of CPR is increased cardiac output as a result of decreasing lung compliance (due to liquid loading) thus facilitating cardiac output in CPR via the thoracic pump mechanism. It may be quite dangerous to do CPR in lungs fully loaded with liquid, which they need to be in TLV. However, we have found that boluses of oxygenated PFC can allow metabolic supply of oxygen for many minutes without ventilation at all. It may be that coordinated use of small amounts of PFC in CPR will allow less ventilation when chest compression needs to be done, but still allow for less chest compressibility, by reason of displacement of relatively elastic gas in the lungs.

Nitric oxide and nitric oxide donors administered via the breathing liquid or the breathing gas, or both, can be used to overcome cold-induced pulmonary vasoconstriction and thus facilitate gas and heat exchange. It is possible that pulmonary vasoconstrictors (nitric oxide antatonists) will be able to reverse the apparent V/Q mismatch caused by rapidly cycled normothermic PFC-in normal lungs, without compromising system circulation.

All, or a large fraction of the oxygen or other breathing gases in the gas ventilation component of MMLV can be replaced with helium in order to reduce ventilating gas viscosity, thus allowing for lower peak airway pressures secondary to gas flow in gas ventilation. Helium is anticipated also to have unique properties in gas-liquid foams: it should form smaller gas bubbles, resulting in improved bubble-induced mixing. The use of helium will also facilitate nitrogen out-gassing from body water during re-warming from hypothermia. The use of 100% inspired helium gas is possible when used with fully oxygenated PFC delivered at appropriate infusion rates (>10 mL/kg/min).

What is claimed is:

1. A method of heat exchange within the lungs of a mammal, comprising:
   a. delivering a first volume of oxygenated liquid to the lungs in an amount approximately equal to the functional residual capacity of the lungs, said oxygenated liquid having a temperature below the temperature of the mammal;
   b. cycling a second volume of oxygenated liquid into and out of the lungs in an amount less than one third of total lung capacity and at a liquid cycle rate defined by delivering said second volume of oxygenated liquid at a rate of 6 mL/kg/min to 50 mL/kg/min, then removing said second volume of oxygenated liquid at a rate of 12 mL/kg/min to 80 mL/kg/min; and
   c. cycling a volume of breathing gas into and out of the lungs at a predetermined gas cycle rate which is independent of the liquid cycle rate.

2. The method of claim 1 in which the temperature of the oxygenated liquid is maintained between approximately −5° C. and 30° C.

3. The method of claim 1 in which the oxygenated liquid is a perfluorochemical.

4. A method of heat exchange within the lungs of a mammal, comprising:
   a. delivering a first volume of biocompatible liquid to the lungs in an amount approximately equal to the functional residual capacity of the lungs, said biocompatible liquid having a temperature below the temperature of the mammal;
   b. cycling a second volume of biocompatible liquid into and out of the lungs in an amount less than one third of total lung capacity and at a liquid cycle rate defined by delivering said second volume of biocompatible liquid at a rate of 6 mL/kg/min to 50 mL/kg/min, then removing said second volume of biocompatible liquid at a rate of 12 mL/kg/min to 80 mL/kg/min; and
   c. cycling a volume of breathing gas into and out of the lungs at a predetermined gas cycle rate which is independent of the liquid cycle rate.

5. The method of claim 4 in which the temperature of the biocompatible liquid is maintained between approximately −5° C. and 30° C.

6. The method of claim 4 in which the biocompatible liquid is a perfluorochemical.

7. A method of heat exchange within the lungs of a mammal, comprising:
   a. delivering a first volume of oxygenated liquid to the lungs in an amount approximately equal to the functional residual capacity of the lungs, said oxygenated liquid having a temperature above the temperature of the mammal;
   b. cycling a second volume of oxygenated liquid into and out of the lungs in an amount less than one third of total lung capacity and at a liquid cycle rate defined by delivering said second volume of oxygenated liquid at a rate of 6 mL/kg/min to 50 mL/kg/min, then removing said second volume of oxygenated liquid at a rate of 12 mL/kg/min to 80 mL/kg/min; and
   c. cycling a volume of breathing gas into and out of the lungs at a predetermined gas cycle rate which is independent of the liquid cycle rate.

8. The method of claim 7 in which the temperature of the oxygenated liquid is maintained between approximately 40° C. and 43° C.

9. The method of claim 7 in which the oxygenated liquid is a perfluorochemical.

10. The method of claim 7 in which the gas includes nitric oxide.

11. A method of heat exchange within the lungs of a mammal, comprising:
    a. delivering a first volume of biocompatible liquid to the lungs in an amount approximately equal to the functional residual capacity of the lungs, said biocompatible liquid having a temperature above the temperature of the mammal;
    b. cycling a second volume of biocompatible liquid into and out of the lungs in an amount less than one third of total lung capacity and at a liquid cycle rate defined by delivering said second volume of biocompatible liquid at a rate of 6 mL/kg/min to 50 mL/kg/min, then removing said second volume of biocompatible liquid at a rate of 12 mL/kg/min to 80 mL/kg/min; and
    c. cycling a volume of breathing gas into and out of the lungs at a predetermined gas cycle rate which is independent of the liquid cycle rate.

12. The method of claim 11 in which the temperature of the biocompatible liquid is maintained between approximately 40° C. and 43° C.

13. The method of claim 11 in which the biocompatible liquid is a perfluorochemical.

14. The method of claim 11 in which the gas contains nitric oxide.

* * * * *